(12) United States Patent
You

(10) Patent No.: US 9,184,390 B2
(45) Date of Patent: Nov. 10, 2015

(54) POLYMERS WITH TUNABLE BAND GAPS FOR PHOTONIC AND ELECTRONIC APPLICATIONS

(75) Inventor: Wei You, Durham, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 13/701,167

(22) PCT Filed: Jun. 8, 2011

(86) PCT No.: PCT/US2011/039610
§ 371 (c)(1),
(2), (4) Date: Jan. 7, 2013

(87) PCT Pub. No.: WO2011/156478
PCT Pub. Date: Dec. 15, 2011

(65) Prior Publication Data
US 2013/0092912 A1    Apr. 18, 2013

Related U.S. Application Data

(60) Provisional application No. 61/352,648, filed on Jun. 8, 2010.

(51) Int. Cl.
| C08G 75/00 | (2006.01) |
| H01L 51/00 | (2006.01) |
| C07D 285/14 | (2006.01) |
| C08G 75/32 | (2006.01) |
| C08G 61/12 | (2006.01) |

(52) U.S. Cl.
CPC .......... *H01L 51/0036* (2013.01); *C07D 285/14* (2013.01); *C08G 61/123* (2013.01); *C08G 61/126* (2013.01); *C08G 75/32* (2013.01); *C08G 2261/146* (2013.01); *C08G 2261/3223* (2013.01); *C08G 2261/3243* (2013.01); *C08G 2261/3246* (2013.01); *C08G 2261/414* (2013.01); *C08G 2261/91* (2013.01)

(58) Field of Classification Search
CPC ... H01L 51/0036; C08G 61/126; C08G 7/325
USPC .......................... 528/370, 380, 373, 377, 423
See application file for complete search history.

(56) References Cited

U.S. PATENT DOCUMENTS

| 2008/0283828 A1 | 11/2008 | Lee et al. | |
| 2010/0078074 A1 | 4/2010 | Yang et al. | |
| 2012/0083583 A1* | 4/2012 | Toppare et al. | 528/380 |
| 2012/0232237 A1* | 9/2012 | Li et al. | 526/257 |

OTHER PUBLICATIONS

Tanimoto et al. (Adv. Synth. Catal. 2004, 346, 1818-1823).*

(Continued)

*Primary Examiner* — Shane Fang
(74) *Attorney, Agent, or Firm* — Myers Bigel Sibley & Sajovec, P.A.

(57) ABSTRACT

The present invention provides, among other things, a copolymer comprising at least one donor monomer and at least one acceptor monomer. The polymer may optionally further comprise at least one additional comonomer. The polymers are useful as a charge-transport, semiconducting, electrochemical conducting, photoconducting, or light emitting material. Microelectronic devices comprising such polymers (e.g., as a heterojunction therein) are also described.

4 Claims, 12 Drawing Sheets

(56) References Cited

OTHER PUBLICATIONS

International Search Report and Written Opinion, PCT/US2011/039610, mailed Nov. 30, 2011.
Li W et al. Mobility-controlled performance of thick solar cells based on fluorinated copolymers. J Am Chem Soc. Oct. 7, 2014; 136: 15566-15576.
Tumbleston Jr et al. Fluorinated polymer yeilds high organic solar cell performance for a wide range of morphologies. Adv Funct Mater. 2013; 23: 3463-3470.
Tumbleston Jr et al. The influence of molecular orientation on organic bulk heterojunction solar cells. Nature Photonics. May 2014; 8: 385-391.
Uy RL et al. Tuning fluorinated benzotriazole polymers through aklylthio substitution and selenophene incorporation for bulk heterojunction solar cells. Macromolecules. 2014; 47: 2289-2295.
Yang L et al. Parallel-like bulk heterojunction polymer solar cells. J Am Chem Soc. 2012; 134: 5432-5435.

* cited by examiner

POLYMERS WITH TUNABLE BAND GAPS FOR PHOTONIC AND ELECTRONIC APPLICATIONS

RELATED APPLICATIONS

This application is a 35 U.S.C. §371 national phase entry of PCT Application PCT/US2011/039610, filed Jun. 8, 2011, and published in English on Dec. 15, 2011, as International Publication No. WO 2011/156478, and which claims the benefit under 35 U.S.C. §119(e) of U.S. Provisional Patent Application Ser. No. 61/352,648, filed Jun. 8, 2010, the disclosure of each of which is incorporated herein by reference in its entirety.

STATEMENT OF GOVERNMENT SUPPORT

This invention was made with Government Support from the Office of Naval Research (contract number N00014-09-1-1016) and the National Science Foundation (contract number DMR-0954280). The US Government has certain rights to this invention.

FIELD OF THE INVENTION

The present invention concerns monomers, polymers, and semiconductor devices comprising such polymers.

BACKGROUND OF THE INVENTION

Tremendous research efforts have been devoted to the development of polymer-based organic photovoltaic (OPV) cells during the last two decades due to projected advantages of these solar cells over their inorganic counterparts, including flexibility, facile processing and manipulation, low weight and low cost. The mechanism by which light is converted into electricity in these OPV devices consists of the following fundamental steps: light absorption, exciton generation, exciton migration, exciton dissociation and charge transport. The bulk heterojunction (BHJ) of regioregular poly (3-hexylthiophene) (RR-P3HT) and [6,6]-phenyl $C_{61}$-butyric acid methyl ester (PCBM) represents one of the most successful systems with reproducible efficiencies approaching 5% after careful optimization. Ma et al., *Adv. Funct. Mater.* 2005, 15, 1617-1622; Li et al., *Nature Mater.* 2005, 4, 864-868.

To further improve the performance of polymer-based BHJs, one has to carefully address the following issues. First, the HOMO and LUMO energy levels of the donor and acceptor components need to have optimal offset to maximize the attainable open circuit voltage ($V_{oc}$). Secondly, the active layer should have compatible absorption with respect to the solar spectrum to maximize the efficiencies of exciton generation, which sets the upper limit for the short circuit current $J_{sc}$. Finally, the morphology of the active layer, which governs the physical interaction between the donor and the acceptor, should be optimized to promote charge separation and favorable transport of photogenerated charges and to maximize the attainable $J_{sc}$ and fill factor (FF). Thompson et al., *Angew. Chem. Int. Ed.* 2008, 47, 58-77; Scharber et al., *Adv. Mater.* 2006, 18, 789-794.

Fulfilling these requirements presents serious challenges in the design of new semiconductive conjugated polymers to be employed as active donors in polymer-based BHJ photovoltaic devices. For example, a number of low band gap polymers have been developed in recent years in the attempt to increase the device efficiency by improving light harvesting. Brabec et al., *Adv. Funct. Mater.* 2002, 12, 709-712; Muhlbacher et al., *Adv. Mater.* 2006, 18, 2884-2889; Peet et al., *Nature Mater.* 2007, 6, 497-500; Zhang et al., *Adv. Funct. Mater.* 2006, 16, 667-674; Andersson et al., *Appl. Phys. Lett.* 2007, 91, 071108/1-071108/3; Slooff et al., *Appl. Phys. Lett.* 2007, 90, 143506/1-143506/3; Wienk et al., *Appl. Phys. Lett.* 2006, 88, 153511/1-153511/3; Yao et al., *Appl. Phys. Lett.* 2006, 89, 153507/1-153507/3; Ashraf et al., *Macromol. Rapid Commun.* 2006, 27, 1454-1459; Blouin et al., *Adv. Mater.* 2007, 19, 2295-2300; Blouin et al., *J. Am. Chem. Soc.* 2008, 130, 732-742.

However, none of them can outperform P3HT in terms of energy conversion efficiency, mainly due to high lying HOMO energy level with regard to the LUMO of the acceptor (usually PCBM), which reduces the $V_{oc}$, or ill-defined morphology of the active blend, which reduces the $J_{sc}$ and FF (or both). In our search for new donor materials, polycyclic aromatic moieties drew our attention. Their rigidly enforced planarity would benefit more effective π electron delocalization when incorporated into the conjugated polymer backbone, which would lead to decreased optical band gaps while providing π-π interactions between polymer chains in thin solid films, thereby improving charge carrier mobility in devices. Roncali, *J. Chem. Rev.* 1997, 97, 173-205; Tovar et al., *J. Am. Chem. Soc.* 2002, 124, 7762-7769; Tovar et al., *Adv. Mater.* 2001, 13, 1775-1780; Polycyclic hydrocarbons I and II; Clar, E. Ed. Academic Press: London 1964; Watson et al., *Chem. Rev.* 2001, 101, 1267-1300; Shklyarevskiy et al., *J. Am. Chem. Soc.* 2005, 127, 16233-16237.

SUMMARY OF THE INVENTION

A first aspect of the present invention is a copolymer comprising, consisting of or consisting essentially of at least one (e.g., 1, 2, 3, 4) donor monomer and at least one (e.g., 1, 2, 3, 4) acceptor monomer. The polymer may optionally further comprise, consist or consist essentially of at least one (e.g., 1, 2, 3, 4) additional comonomer. Various donor monomers, acceptor monomers and additional comonomers are described below.

A further aspect of the invention is a polymer comprising, consisting of or consisting essentially of at least one (e.g., 1, 2, 3, 4) acceptor monomer selected from a subset of the donor monomers described below. Such polymers may be homopolymers or copolymers.

A further aspect of the invention is an acceptor monomer as described herein.

A further aspect of the present invention is the use of a polymer as described herein as a charge-transport, semiconducting, electrochemical conducting, photoconducting, or light emitting material.

A further aspect of the present invention is a microelectronic device comprising a polymer as described herein (e.g., as said heterojunction therein).

A father aspect of the present invention is a method of synthesis as described herein for synthesis of the monomers and polymers as described herein.

The present invention is explained in greater detail in the drawings herein and the specification set forth below. The disclosures of all United States patent references cited herein are incorporated by reference herein in their entirety.

DETAILED DESCRIPTION OF THE EMBODIMENTS

Figure 1:
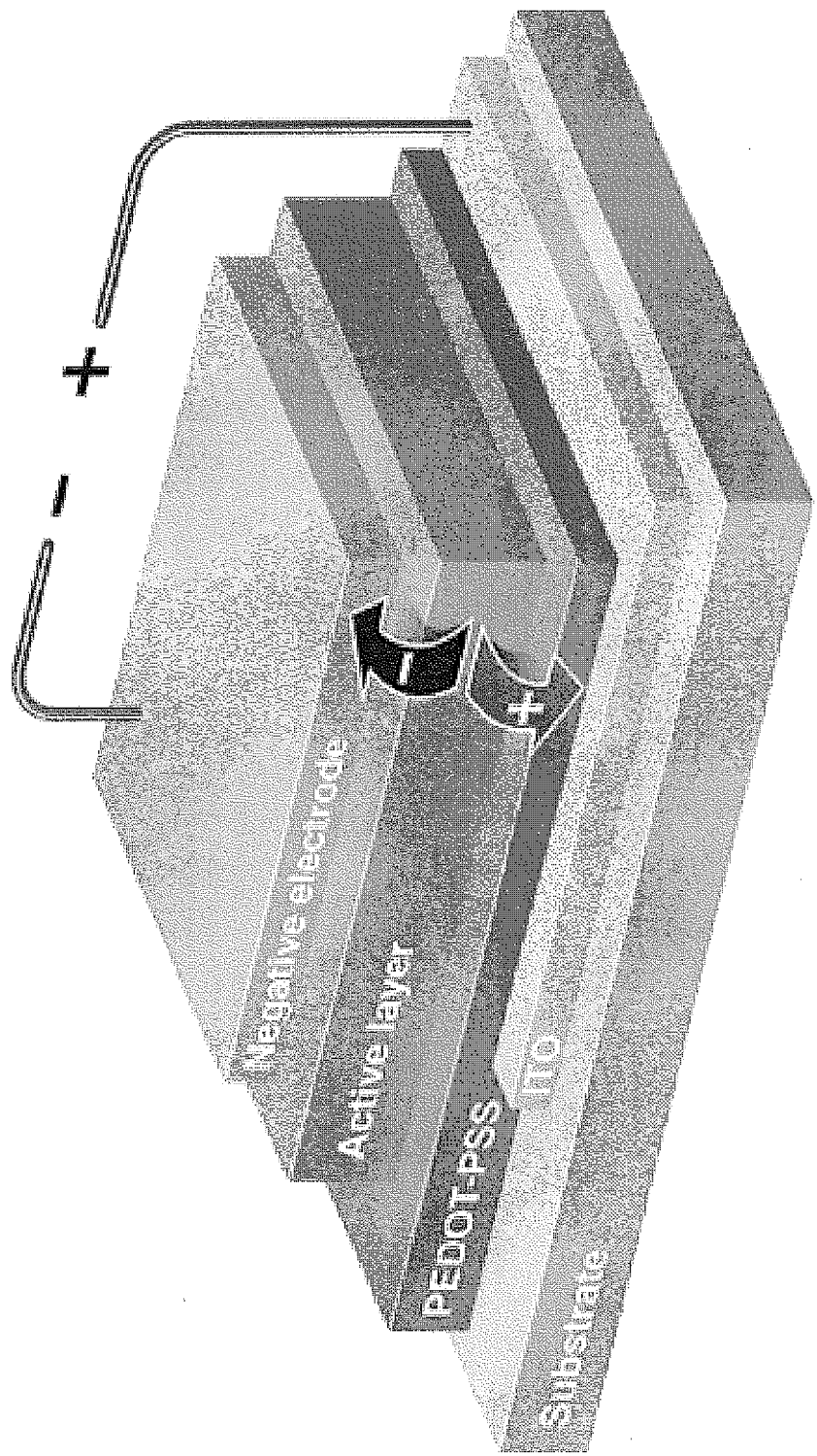
FIG. 1. Schematic illustration of one embodiment of a photocell of the invention.

"Alkyl" as used herein alone or as part of another group, refers to a straight or branched chain hydrocarbon containing from 1 to 20 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like.

"Fluoroalkyl" as used herein refers to an alkyl group as described above, substituted one or more times (e.g., 1, 2, 3, 4, 6, 8, etc.) with a fluoro group.

"Alkoxy" as used herein alone or as part of another group, refers to an alkyl or loweralkyl group, as defined herein (and thus including substituted versions such as fluorolyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Reactive functional group" as used herein includes any suitable reactive group. Examples include, but are not limited to, reactive halide functional groups (e.g., fluoro, chloro, bromo, iodo), reactive boron functional groups (e.g., boronic acids, boronic esters, boranes), and reactive tin functional groups (e.g., trialkyl tin). Such reactive functional groups are known. See, e.g., U.S. Pat. Nos. 7,534,503; 7,348,428; and 5,777,070.

As noted above, the present invention provides a copolymer comprising, consisting of or consisting essentially of at least one (e.g., 1, 2, 3, 4) donor monomer and at least one (e.g., 1, 2, 3, 4) acceptor monomer. The donor monomer can be selected from the group consisting of:

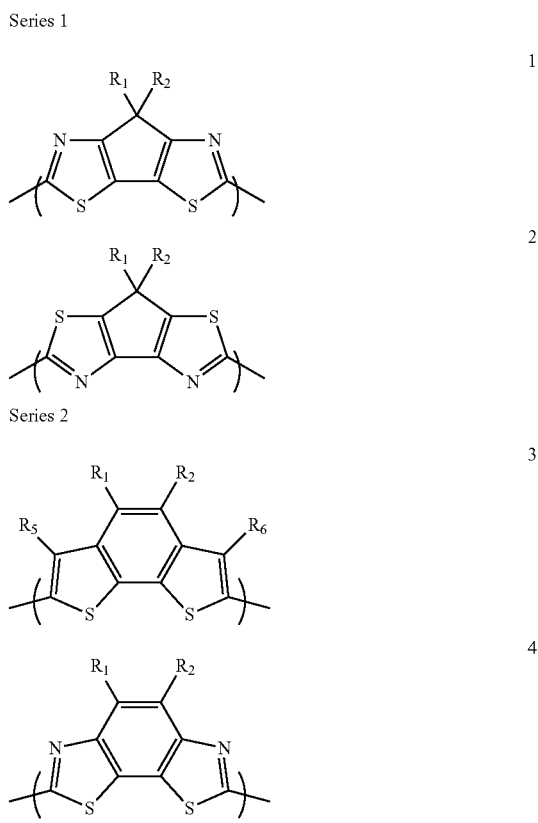

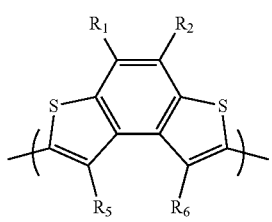
5
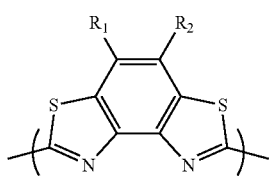
6
Series 3
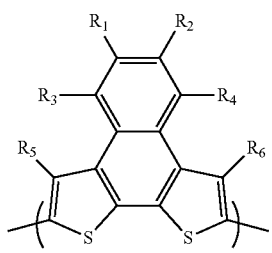
7
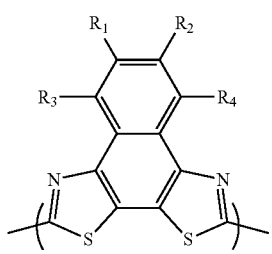
8
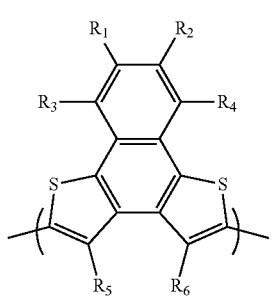
9
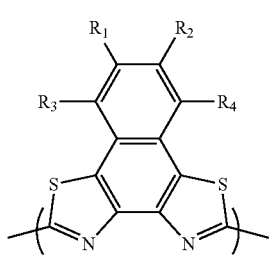
10
Series 4
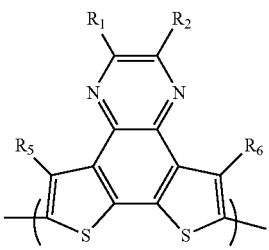
11
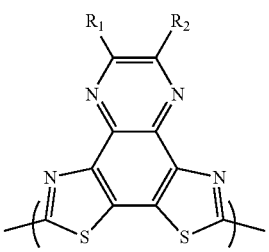
12
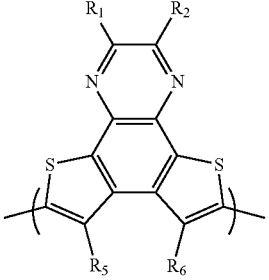
13
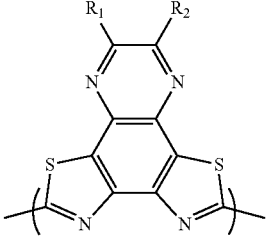
14
Series 5
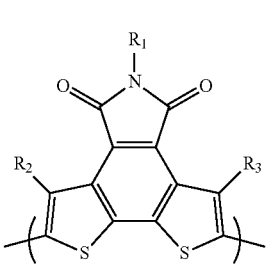
15
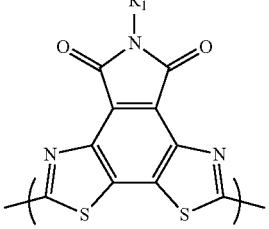
16

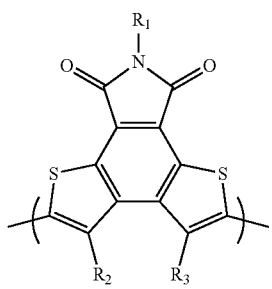
17
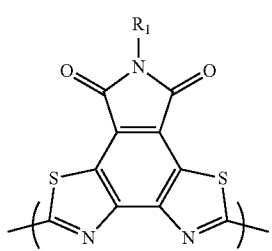
18
Series 6
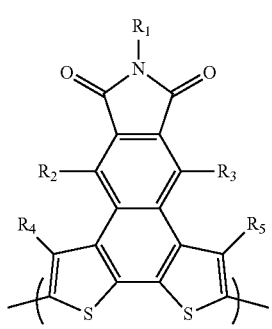
19
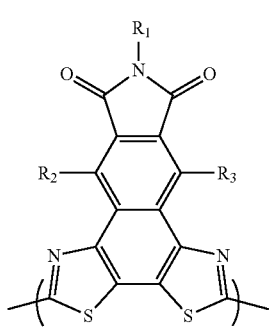
20
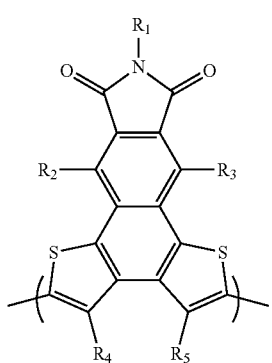
21
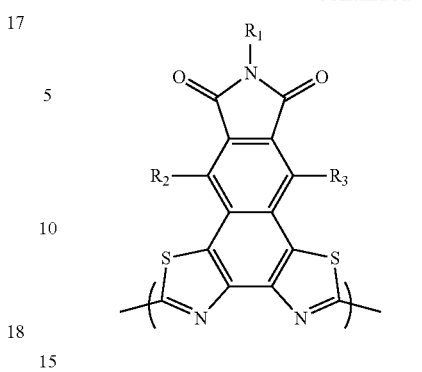
22
Series 7
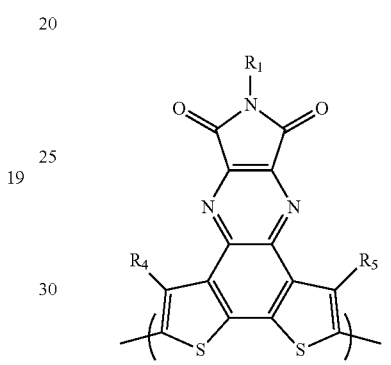
23
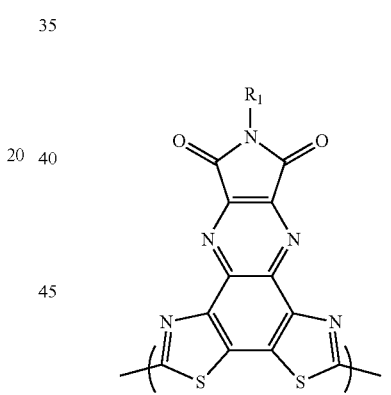
24
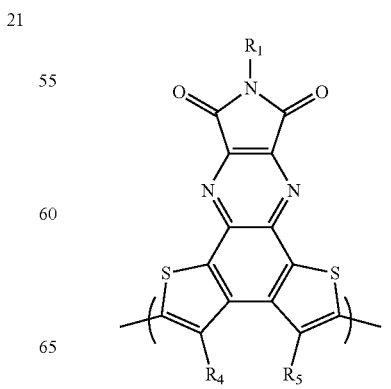
25

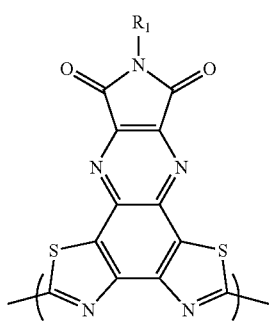
Series 8
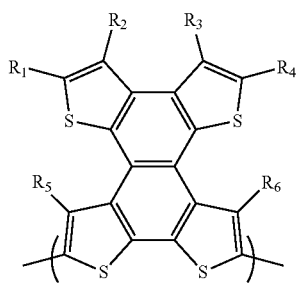
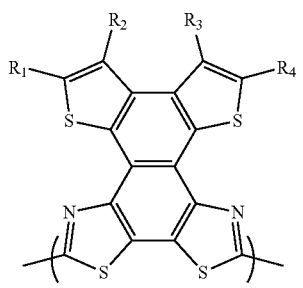
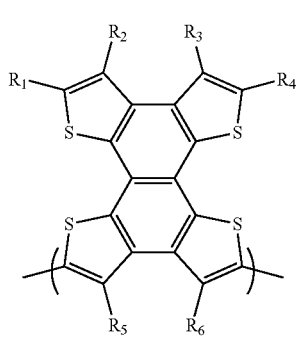
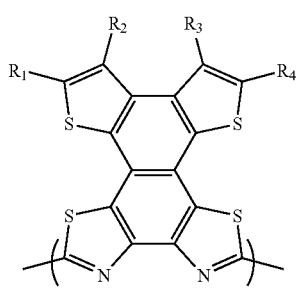
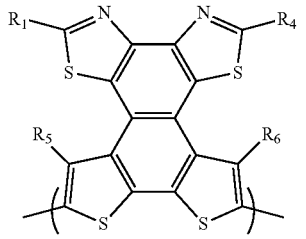
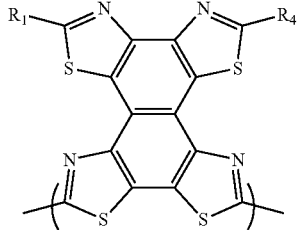
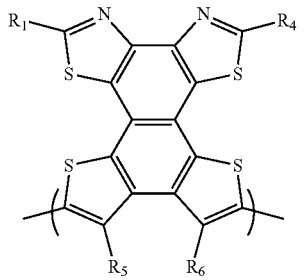
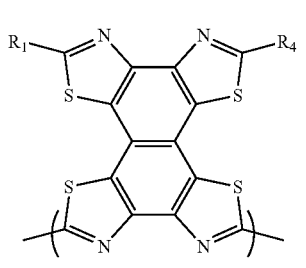
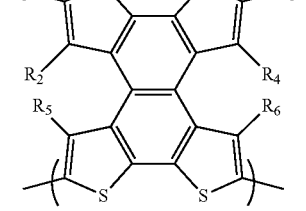
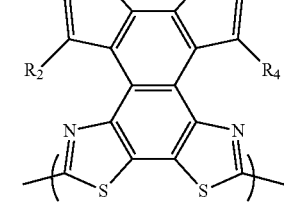

37
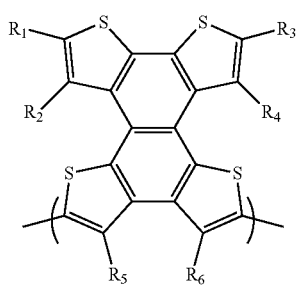
38
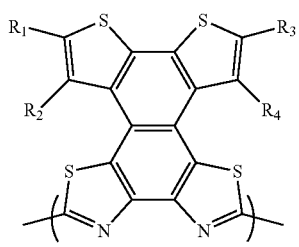
39
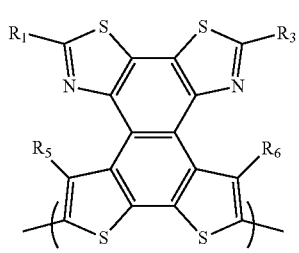
40
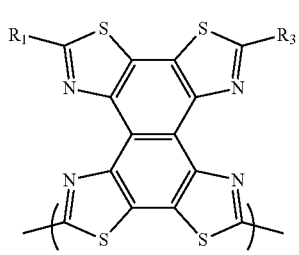
41
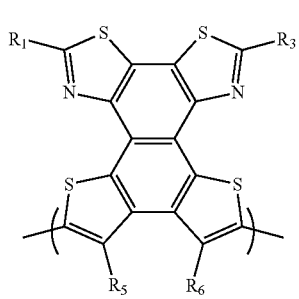
42
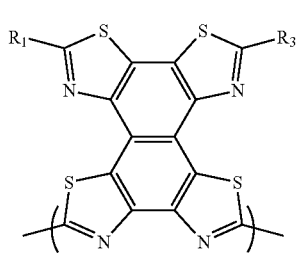
Series 9
43
44
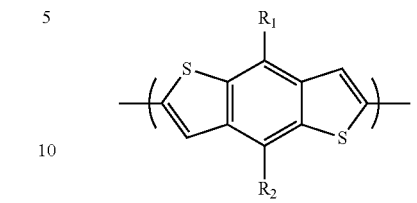
45
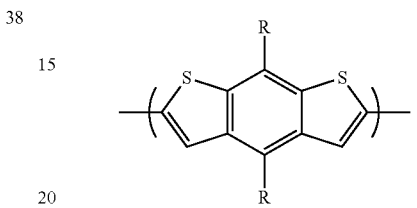
46
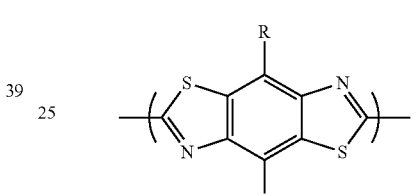
47
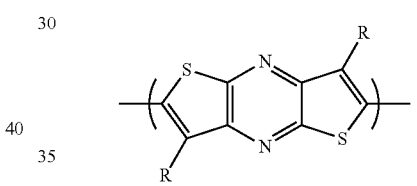
48
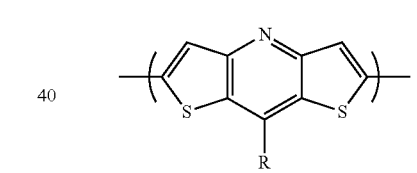
and the acceptor monomer can be selected from the group consisting of:
Series A2
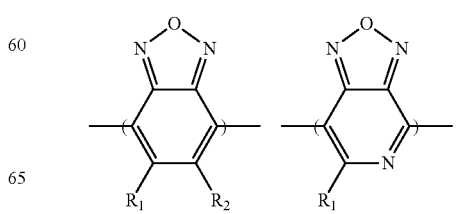

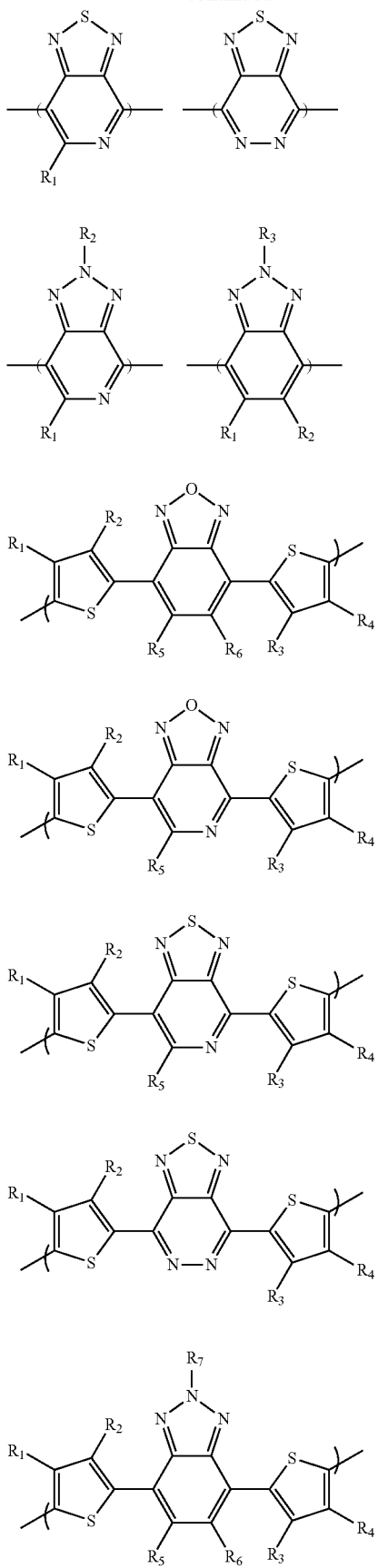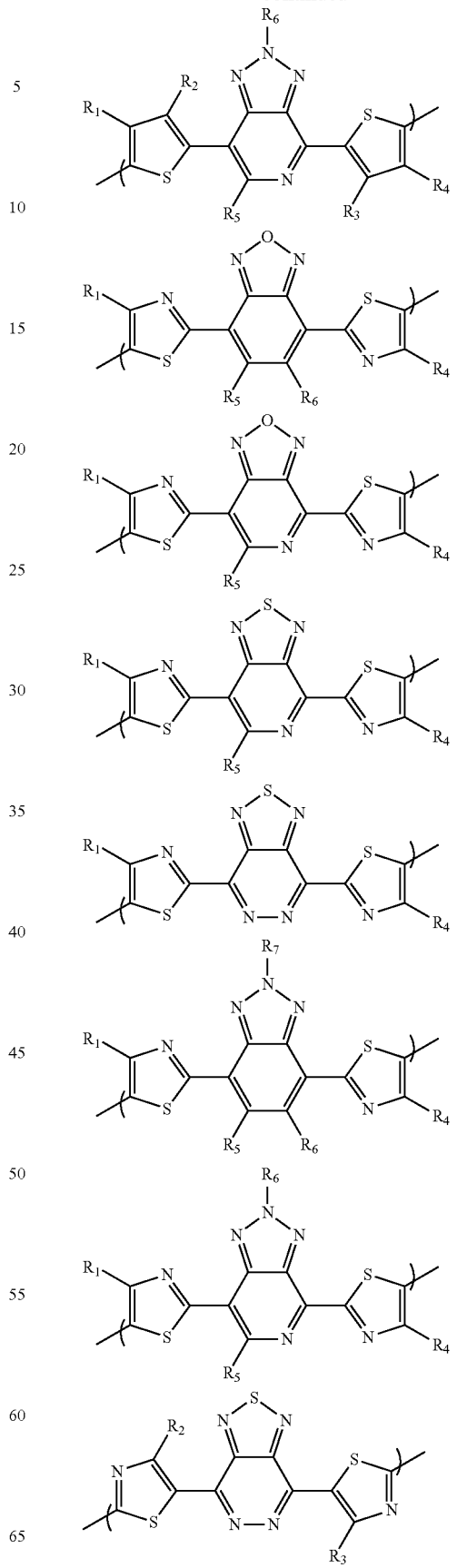

-continued
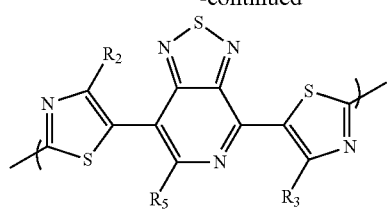
Series A3
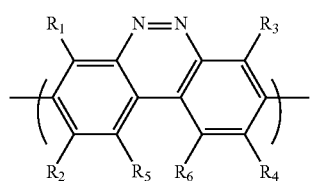
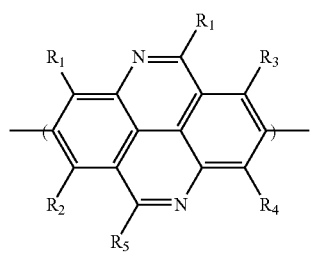
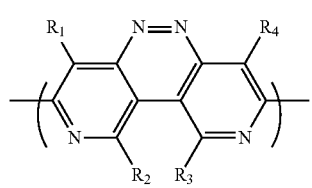
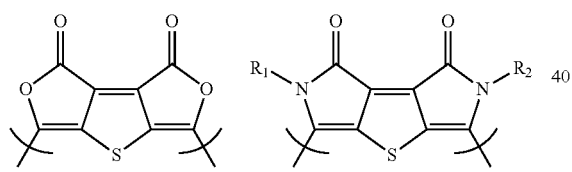
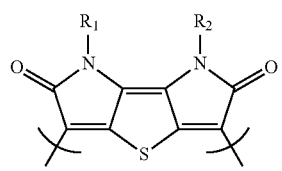
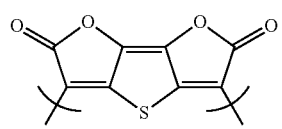
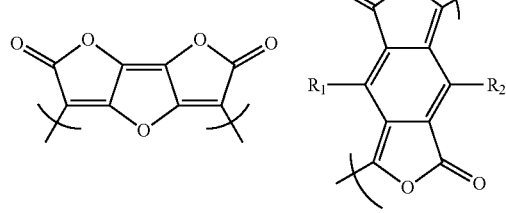
-continued
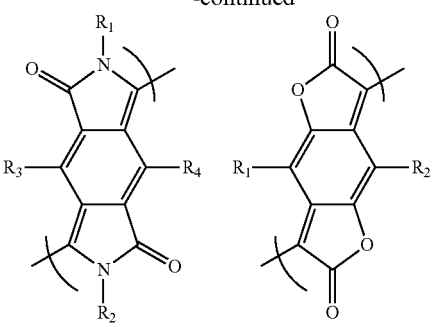
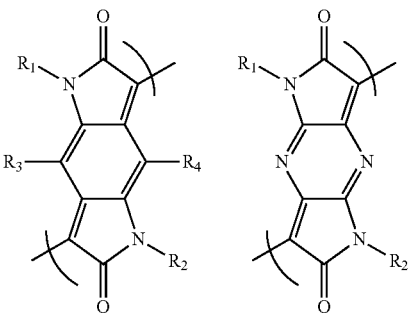
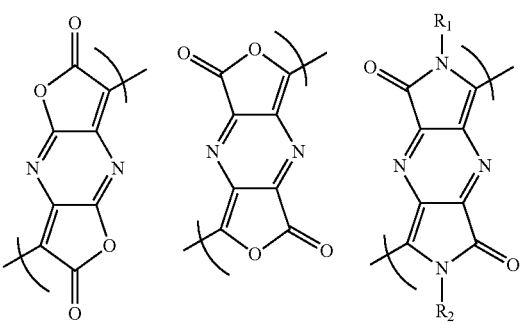
Series A4
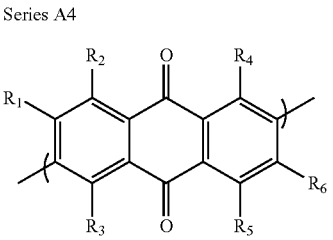
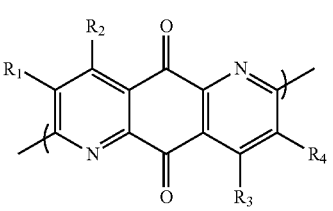
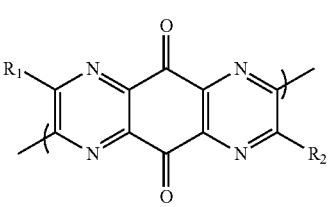

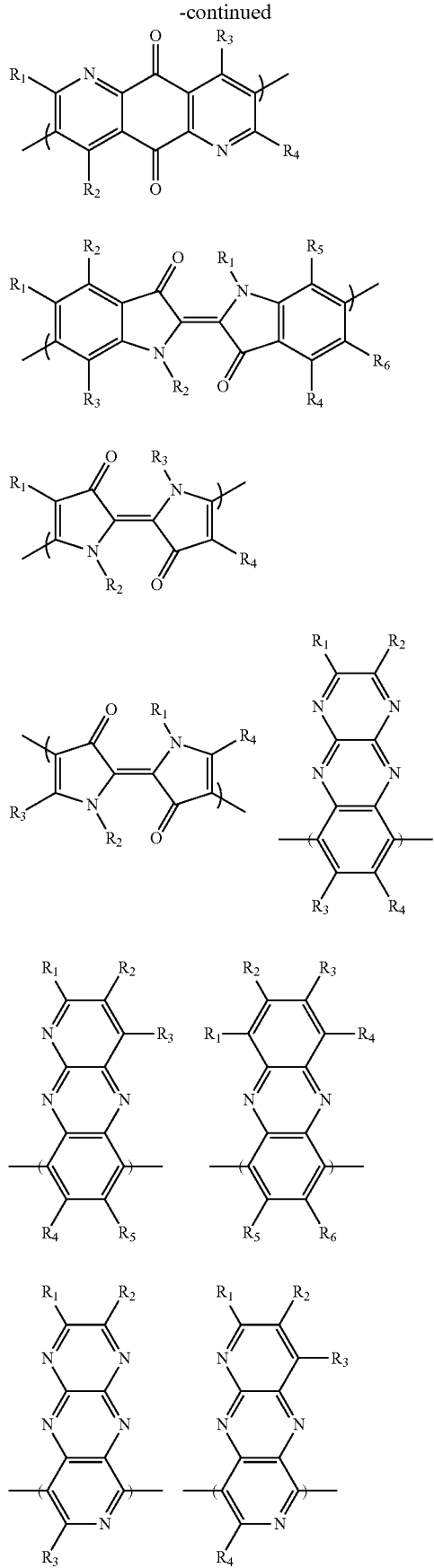
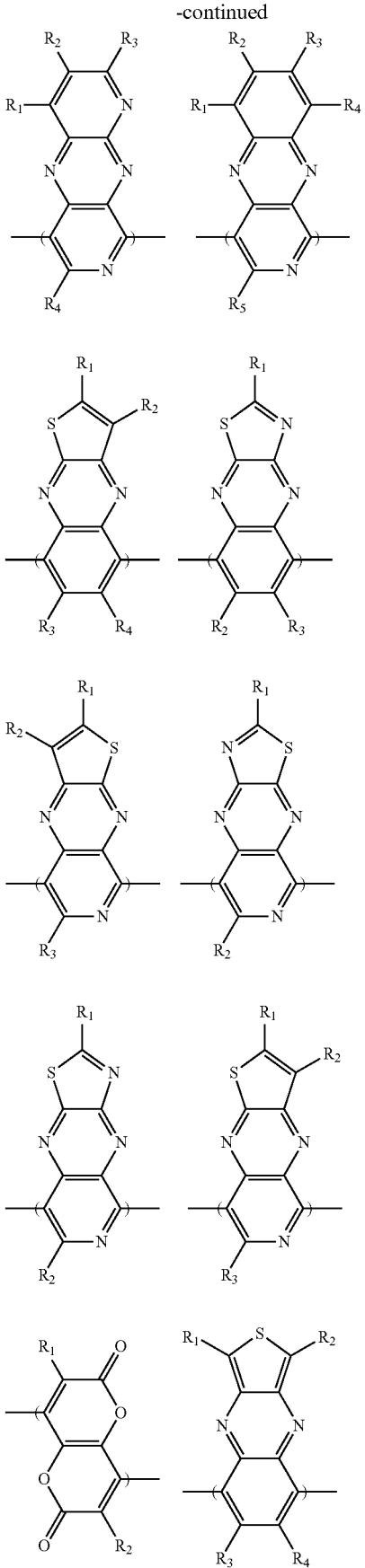

-continued
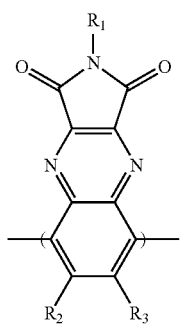
Series A5
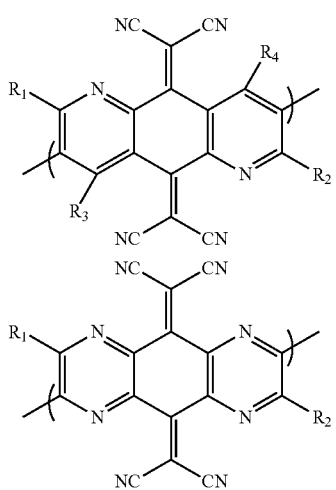
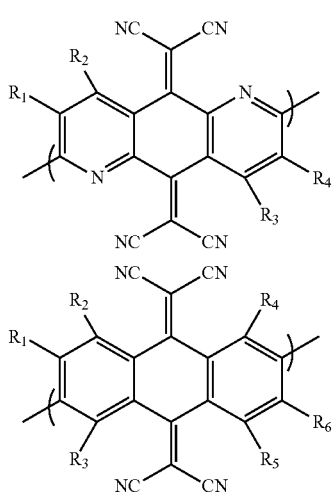
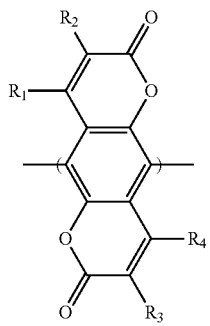
-continued
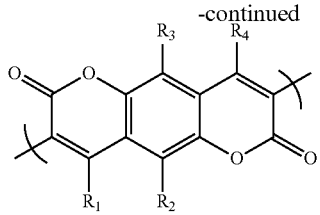
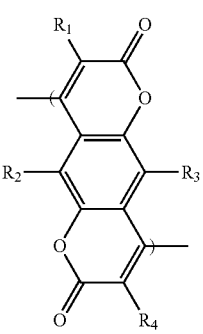 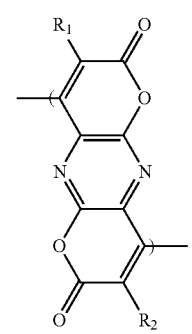
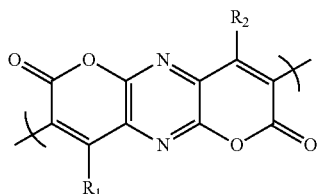
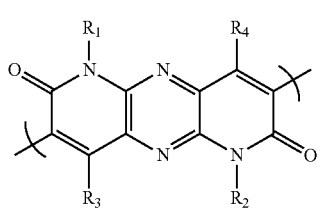
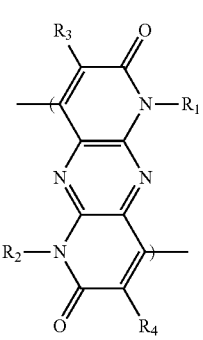
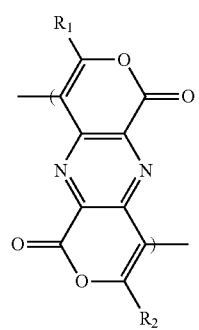

-continued

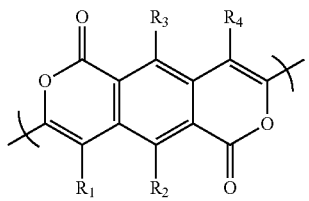 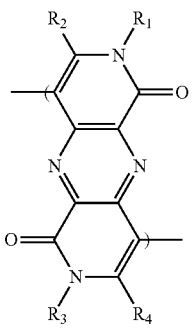

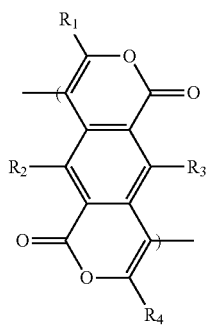

wherein each $R_1$, $R_2$, $R_3$, $R_4$, $R_5$, $R_6$, and $R_7$ is independently selected from the group consisting of H, C1-C20 alkyl, C1-C20 fluoroalkyl, C1-C20 alkoxy, C1-C20 fluoroalkoxy, halo, aryl, CN and $NO_2$.

An acceptor molecule may also be a monomer:

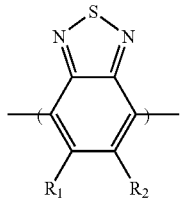

A1 wherein each of $R_1$ and $R_2$ of A1 is halo (e.g., fluoro).

The polymer may optionally further comprise, consist or consist essentially of at least one (e.g., 1, 2, 3, 4) additional comonomer, such as a:

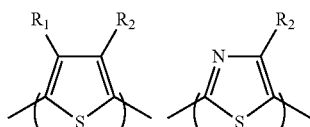 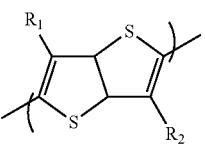

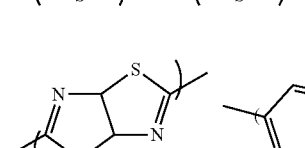

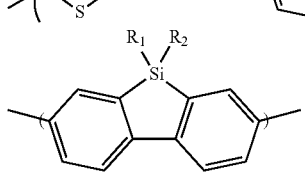

-continued

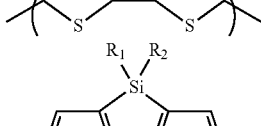

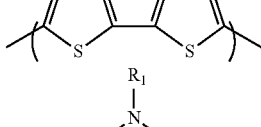

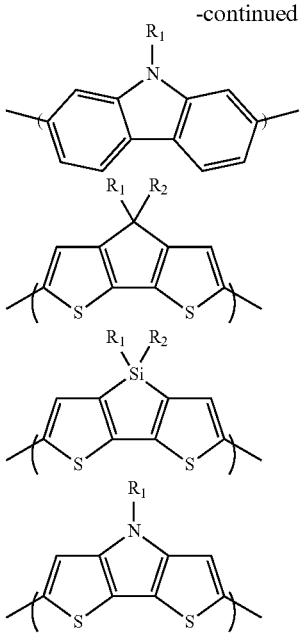

or combinations thereof, wherein $R_1$ and $R_2$ are as given above.

In some embodiments, the polymer has the formula:

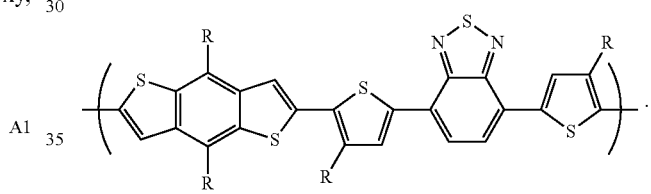

wherein each R is independently as given above.

In some embodiments, the polymer has the formula:

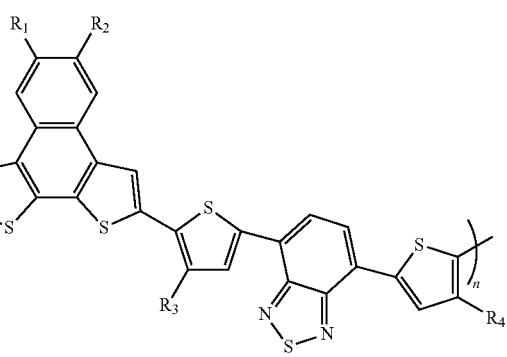

PBDT

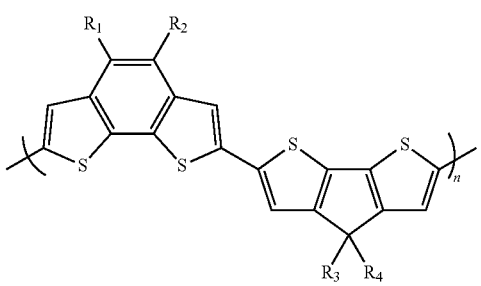

-continued

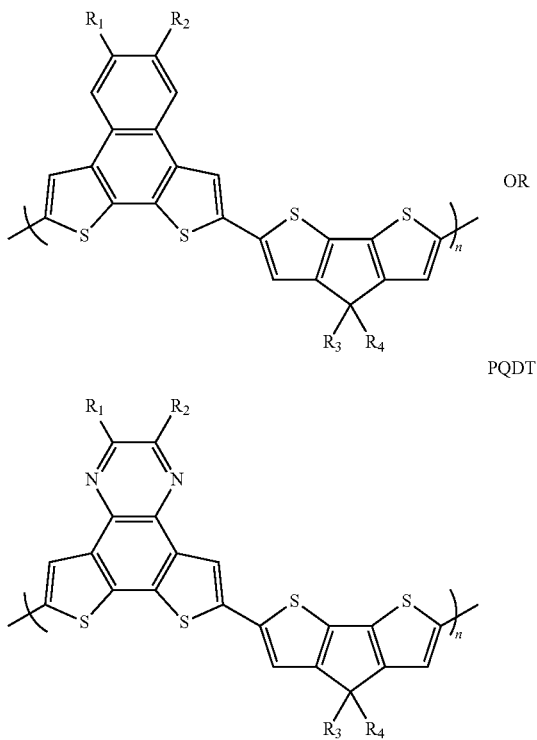

PNDT

OR

PQDT wherein each $R_1$, $R_2$, $R_3$ and $R_4$ is independently as given above.

In some embodiments, the polymer has the formula:

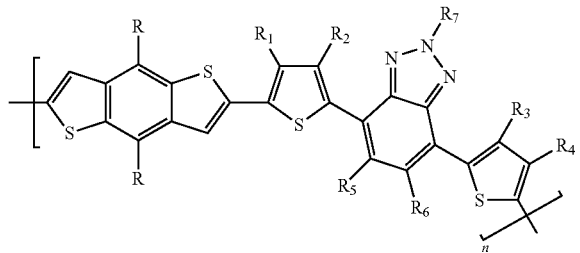

wherein each R, $R_1$, $R_2$, $R_3$, $R_4$, $R_5$, $R_6$ and $R_7$ is independently as given above.

In some embodiments of all of the foregoing, $R_5$ and $R_6$ are both halo, particularly fluoro.

In some embodiments of all of the foregoing, R is alkyl.
In some embodiments of all of the foregoing, R is alkyl.
In some embodiments of all of the foregoing, $R_1$ is H.
In some embodiments of all of the foregoing, $R_2$ is H.
In some embodiments of all of the foregoing, $R_3$ is H.
In some embodiments of all of the foregoing, $R_4$ is H.

A further aspect of the invention is a polymer comprising, consisting of or consisting essentially of at least one (e.g., 1, 2, 3, 4) acceptor monomer as given above. Such polymers may be homopolymers or copolymers with at least one (e.g., 1, 2, 3, 4) additional monomer. When a copolymer, the copolymer may comprise a donor monomer such as described above, or an additional comonomer such as described above.

In some embodiments, the polymers described above and herein have a number average molecular weight of from 500 or 1,000 grams per mole up to 1,000,000 or 5,000,000 grams per mole, or more. The term "polymer" is intended to include oligomers, or lower molecular weight polymers. Where formulas herein include n, it will be understood that n is not critical and can be removed (and, the polymer molecular weight can be as given above). Alternatively, in some embodiments n may represent any suitable integer, e.g., 1, 2, 3, 4, 10, or 20 or more, up to 10,000, 100,000, 1,000,000, 5,000,000 or more. Terminal groups on the polymer are not critical and depend upon the particular terminal groups or reactive functional groups present on the monomers (to which they may correspond), polymerization reaction, subsequent reactions, etc. Thus terminal groups may be any suitable inert terminal group or reactive functional groups, including but not limited to those described as reactive functional groups above, and the terminal groups described in U.S. Pat. Nos. 7,943,751 and 7,943,696.

Monomers illustrated above are shown with open bonds. It will be understood that open bonds can be replaced with a suitable substituent (e.g., X and Y respectively) when the monomer is expressed as a compound per se. See also U.S. patent application Ser. No. 12/726,896 (You et al.), which is incorporated by reference herein in its entirety. In these embodiments, X and Y are each independently selected from the group consisting of H and reactive functional groups such as described above.

In some embodiments, at least one of X and Y is a halide functional group.

In some embodiments, at least one of X and Y is either a boron functional group or a reactive tin functional group.

In some embodiments, one of X and Y is a halide functional group, and the other is either a boron functional group or a reactive tin functional group.

In some embodiments, both X and Y are halo.
In some embodiments, both X and Y are a trialkyltin.

Monomers and polymers of the present invention can be made in accordance with the techniques described herein, or variations thereof that will be apparent to those skilled in the art based upon the present disclosure.

The polymers are useful for the production of microelectronic devices such as optoelectronic devices in accordance with known techniques or variations thereof that will be apparent to those skilled in the art. See, e.g., U.S. Pat. Nos. 7,534,503; and 7,348,428; US Patent Application Publication No. US 2007/0017571; PCT Patent Application No. WO 2008/000664; see also U.S. Pat. Nos. 7,547,926; 7,407,831; 5,454,880; and 5,331,183. In some embodiments, the polymer comprises a heterojunction in the device. In some embodiments, the device comprises a first electrode, a second electrode, and a photoactive material disposed between the first and second electrode, with photoactive material comprising, consisting of, or consisting essentially of a polymer as described herein. Illustrative devices include, but are not limited to, photovoltaic cells, field effect transistors, light emitting diodes, photodectectors, photovoltaic detectors, imaging devices, lasing devices, storage elements, amplifiers, emitters, and electrochromic displays. In some embodiments of the foregoing, one or more additional layers of conductors, semiconductors, polymers, substrates/supports, and combinations thereof, along with any desired patterns, features, vias and the like, may be included as is known in the art, or as will be apparent to those skilled in the art based on the present disclosure. In some embodiments, the polymers of the invention may be mixed or blended with additional ingredients or additional polymers such as fullerenes, as is known in the art, or as will be apparent to those skilled in the art based on the present disclosure. A particular example of a photovoltaic cell is schematically illustrated in FIG. 1, where "PEDOT-PSS" refers to the conductive polymer Poly(3,4-ethylenedioxythiophene)-Polystyrene Sulfonate, "ITO" refers to the transparent conducting oxide indium tin oxide, the active layer comprises a polymer of the present invention (optionally blended with other materials such as fullerenes), the negative electrode is, for example, Ca/Al, and the substrate may be any suitable material (preferably optically transparent) organic polymeric or inorganic material such as silicate glass, fused quartz, borosilicate glass, etc. For example, the active layer may comprise a polymer of the invention mixed with an n-type organic semiconductor material (e.g., fullerene) in an appropriate ratio (e.g. a 1:1 weight ratio) in the solvent, spin coated on its immediately adjacent underlying layer, and dried to provide a random mixture of the two on the immediately adjacent underlying layer.

The present invention is explained in greater detail in the following non-limiting examples.

EXAMPLE 1

Figure 2:
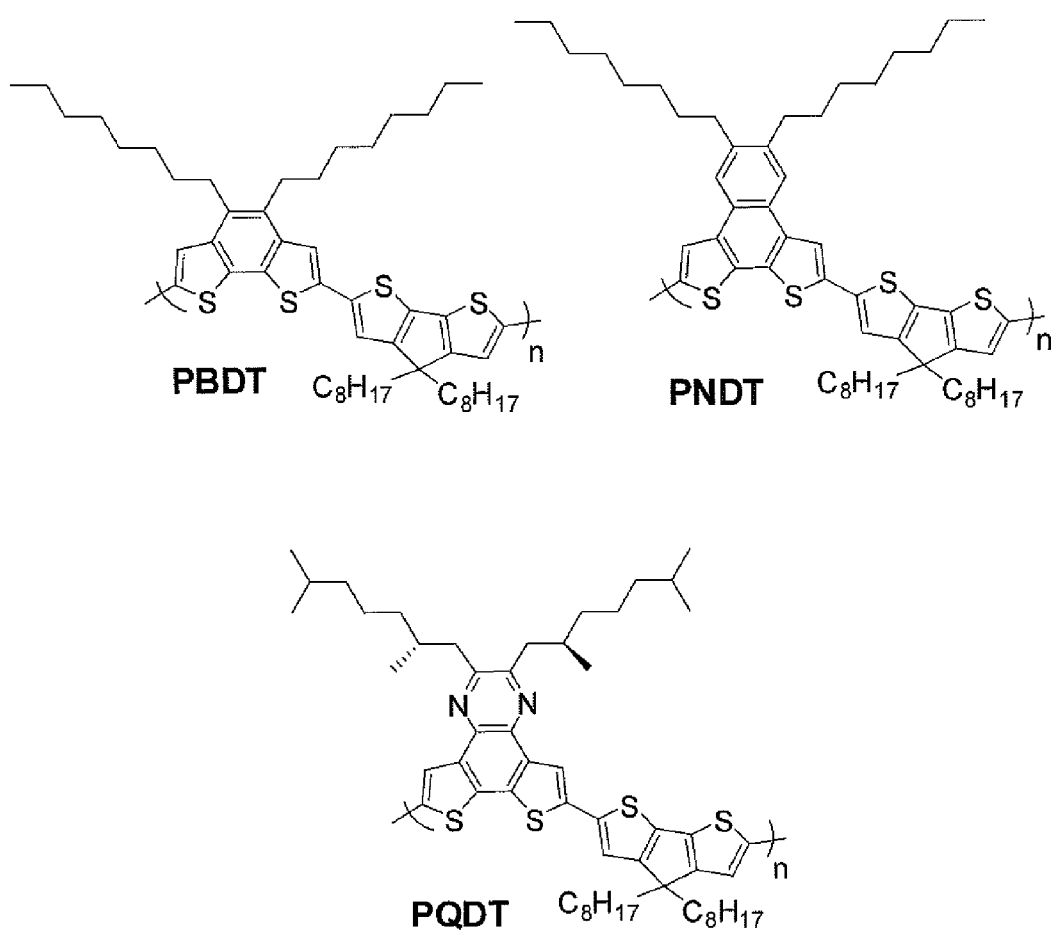
FIG. 2. The structure of three alternating copolymers PBDT, PNDT, PQDT.

To exemplify the application of the unique features associated with these polycyclic aromatic moieties for polymer-based photovoltaics, we synthesized a family of three structurally related conjugated alternating copolymers, namely poly[2,6-(4,4-dioctyl-4H-cyclopenta[2,1-b:3,4-b']dithiophene)-alt-2,7-(4,5-dioctylbenzo[2,1-b:3,4-b']dithiophene)] (PBDT), poly[2,6-(4,4-dioctyl-4H-cyclopenta[2,1-b:3,4-b']dithiophene)-alt-2,9-(5,6-dioctylnaphtho[2,1-b:3,4-b']dithiophene)] (PNDT) and poly[2,6-(4,4-dioctyl-4H-cyclopenta[2,1-b:3,4-b']dithiophene)-alt-6,9-(2,3-bis((S)-2,6-dimethylheptyl)dithieno[3,2-f:2',3'-h]quinoxaline] (PQDT) (FIG. 2). The repeating units of these three copolymers consist of two modified bithiophene units with one of them planarized by bridging benzo, naphtho and quinoxalino segment, respectively. The known 2,6-(4,4-dioctyl-4H-cyclopenta)[2,1-b;3,4-b']dithiophene moieties were introduced as the other bithiophene unit to improve the solubility of resultant copolymers, facilitating polymer characterization and photovoltaic devices fabrications. The intrinsic electronic properties of these planarized bithiophene moieties offered moderate flexibility in fine-tuning electronic properties of the corresponding copolymers. Presented below are the synthesis, the physical properties and the preliminary photovoltaic performances of these structurally related copolymers. The elucidated structure/property relationships will assist the intelligent exploration of future design of materials for OPV applications.

Results and Discussion

Monomer Synthesis.

To obtain benzo[2,1-b:3,4-b']dithiophene, naphtho[2,1-b:3,4-b']dithiophene and quinoxalino[2,1-b:3,4-b']dithiophene moieties for the preparation of polymers PBDT, PNDT and PQDT, different synthetic strategies were applied to bridge various π systems to the bithiophene unit. Side alkyl chains were incorporated to improve solubility of resulting polymers. The synthetic route for the preparation of di-brominated monomer quinoxalino[2,1-b:3,4-b']dithiophene 7 for PQDT is shown in Scheme 1. Quinoxalino[2,1-b:3,4-b']dithiophene was achieved via the condensation reaction of an alkylated vicinal diamine 4 with 1,2-diketone of benzo[2,1-b:3,4-b']bithiophene-4,5-quinone (5). 1,2-diamine 4 was obtained through multi-step synthesis from commercially available aldehyde 1. The classical acyloin condensation of aldehyde 1 followed by PCC oxidation gave alkylated 1,2-diketone 2, which was converted to 1,2-dioxime 3 and followed by Pt catalyzed hydrogenation to give the hydrogen chloride salt of 1,2-diamine in almost quantitative yield. The condensation of 1,2-diamine 4 with 1,2-diketone benzo[2,1-b:3,4-b']bithiophene-4,5-quinone 5 under aerobic conditions directly afforded the dehydrogenated product of quinoxalino[2,1-b:3,4-b']dithiophene 6. Di-bromination of 6 was accomplished using N-bromosuccinimide (NBS) to provide final co-monomer 7. The other co-monomer 8 was prepared by dilithiation of 4,4-dioctyl-4H-cyclopenta[2,1-b:3,4-b']dithiophene using t-BuLi followed by quenching the intermediate with 2-isopropoxy-4,4,5,5-tetramethyl[1,3,2]dioxaborolane.

The preparation of 2,7-dibromo-4,5-dioctylbenzo[2,1-b:3,4-b']dithiophene is depicted in Scheme 2. The synthesis was completed by a palladium catalyzed coupling reaction between 3,3'-diiodo-2,2'-bithiophene and 9-octadecyne[22,23] followed by NBS bromination in a mixed solvent of chloroform/acetic acid.

Scheme 1. Synthesis of copolymer PQDT[a]

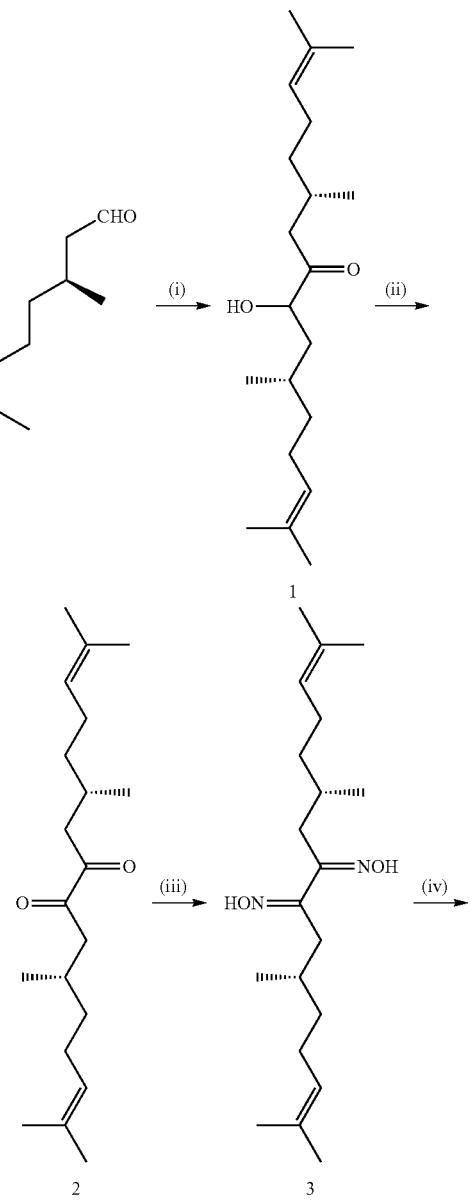

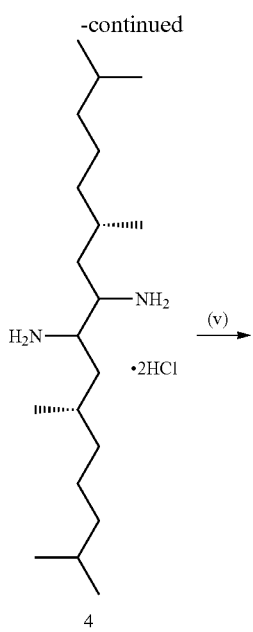

4

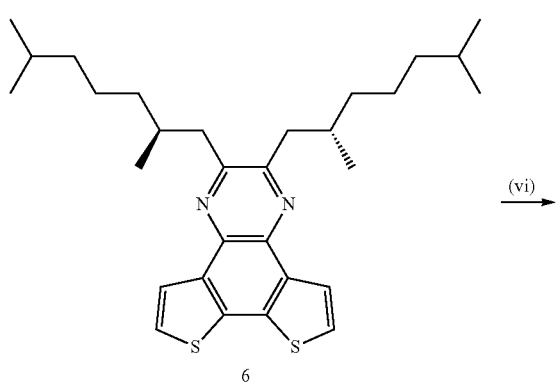

6

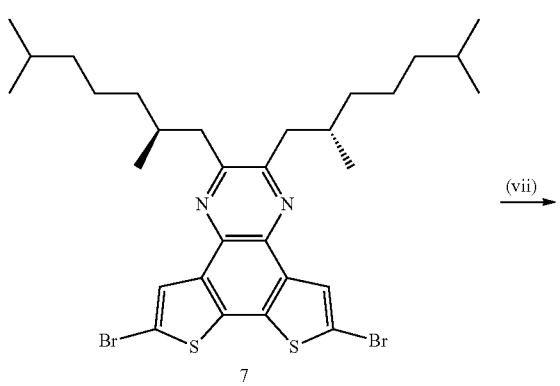

7

PQDT

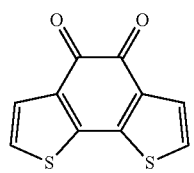

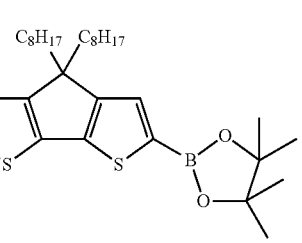

8

[a]Reagents and conditions: (i) 3-ethyl-5-(2-hydroxyethyl)-4-methylthiazolium bromide, triethylamine, ethanol, Ar, reflux overnight; (ii) pyridinium chlororchromate (PCC), methylene chloride, reflux overnight; (iii) hydroxyammonium chloride, pyridine, ethanol, reflux for 5 hours; (iv) platinum oxide, $H_2$, concentrated hydrogen chloride, absolute ethanol, r.t.; (v) 5, pyridine, methanol, reflux overnight; (vi) NBS, $CHCl_3$ — HOAc (1:1, v/v), r.t.; (vii) 8, tetrakis(triphenylphosphine)palladium, $Na_2CO_3$, toluene, $H_2O$, reflux, 7 days.

Scheme 2. Synthesis of copolymer PBDT[a]

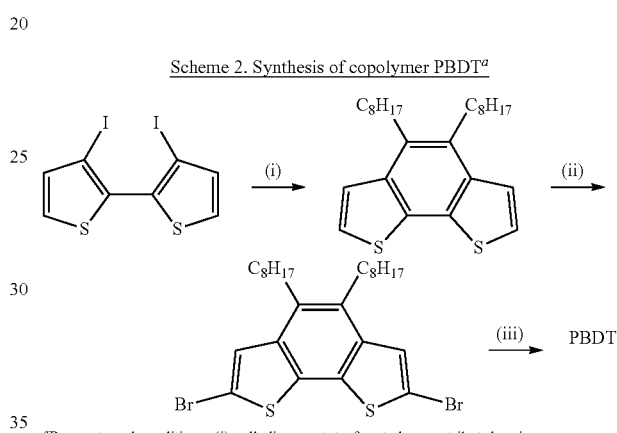

[a]Reagents and conditions: (i) palladium acetate, 9-octadecyne, tributyl amine, anhydrous DMF, 130° C.; (ii) NBS, $CHCl_3$ — HOAc (1:1, v/v), r. t.; (iii) 8, tetrakis (triphenylphosphine)palladium, $Na_2CO_3$, toluene, $H_2O$, reflux, 7 days.

As outlined in Scheme 3, the preparation of 2,9-dibromo-5,6-dioctylnaphtho[2,1-b:3,4-b']dithiophene started from 1,2-dichlorobenzene. A nickel-catalyzed Kumada coupling reaction between 1,2-dichlorobenzene and freshly prepared octylmagnesium bromide offered 1,2-dioctylbenzene. Iodination of 1,2-dioctylbenzene followed by palladium-catalyzed Suzuki coupling reaction with 3-thiophene boronic acid provided 4,5-bis(3-thienyl)-1,2-dioctylbenzene at high yield.[18] 5,6-dioctylnaphtho[2,1-b:3,4-b']dithiophene was then prepared via oxidative photocyclization by irradiation of a diluted toluene solution of 4,5-bis(3-thienyl)-1,2-dioctylbenzene under ambient conditions in the presence of a catalytic amount of iodine.[24,25] Subsequent bromination using NBS in a mixed solvent of chloroform/acetic acid offered the co-monomer 2,9-dibromo-5,6-dioctylnaphtho[2,1-b:3,4-b']dithiophene Scheme 3. Synthesis of copolymer PNDT[a]

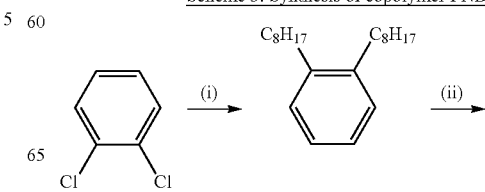

-continued

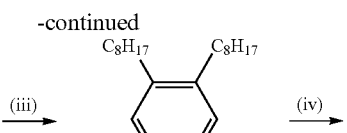

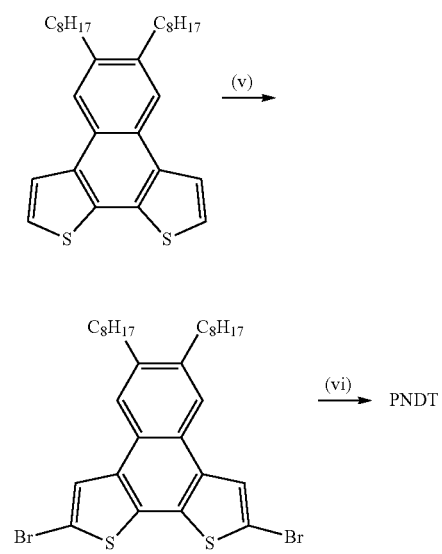

[a]Reagents and conditions: (i) octylmagnesium bromide, 1,3-Bis(diphenylphosphino)propane)-nickel(II) chloride, anhydrous ethyl ether; (ii) I$_2$, NaIO$_3$ HOAc — H$_2$SO$_4$ — H$_2$O, reflux; (iii) 3-thiophene boronic acid, Pd(PPh$_3$)$_4$, Na$_2$CO$_3$, toluene, EtOH and H$_2$O, reflux; (iv) I$_2$, O$_2$, under irradiation of 400 W mercury lamp; (v) NBS, CHCl$_3$ — HOAc (1:1, v/v), r.t.; (vi) 8, tetrakis(triphenylphosphine)palladium, Na$_2$CO$_3$, toluene, H$_2$O, reflux, 7 days.

Polymer Synthesis.

All copolymers were synthesized by a polycondensation of 2,6-bis(4,4,5,5-tetramethyl-1,3,2-dioxaborolan-2-yl)-4,4-dioctyl-4H-cyclopenta[2,1-b:3,4-b']dithiophene (8) and corresponding dibrominated co-monomers through Suzuki coupling reactions. All crude copolymers were washed successively by water and methanol and extracted by methanol and acetone successively using a Soxhlet apparatus to remove byproducts and oligomers. Finally, the polymers were extracted by chloroform, re-collected by precipitating them into methanol, and dried under vacuum. The alternating copolymers PBDT, PNDT and PQDT are soluble in common organic solvents such as methylene chloride, chloroform, THF and toluene and can be easily processed into thin films for further characterizations. The molecular structures of all alternating copolymers were confirmed by $^1$H NMR spectroscopy (supporting information).

The yields and molecular weights of three copolymers are listed in Table 1. High polymer yields (~90%) were obtained from Suzuki-coupling polymerizations. The molecular weights were determined by gel permeation chromatography (GPC) in THF using polystyrene standards. Thermogravimetric analysis (TGA) and differential scanning calorimetry (DSC) analysis revealed that all polymers did not degrade below 430° C. nor did they melt (supporting information).

TABLE 1

Polymerization results for polymers PBDT, PNDT and PQDT.

| | Yield[a] [%] | $M_w$[b] [kg/mol] | $M_n$[b] [kg/mol] | PDI[b] | $T_d$[c] [° C.] |
|---|---|---|---|---|---|
| PBDT | 88 | 39.1 | 20.6 | 1.90 | 432 |
| PNDT | 90 | 25.8 | 16.6 | 1.54 | 432 |
| PQDT | 86 | 30.9 | 16.1 | 1.91 | 430 |

[a]Soluble polymers extracted by CHCl$_3$ with respect to the overall yield.
[b]Determined by GPC in THF using polystyrene standards.
[c]The temperature of degradation corresponding to a 5% weight loss determined by TGA at a heating rate of 10° C./min.

Optical Absorption.

Figure 3:
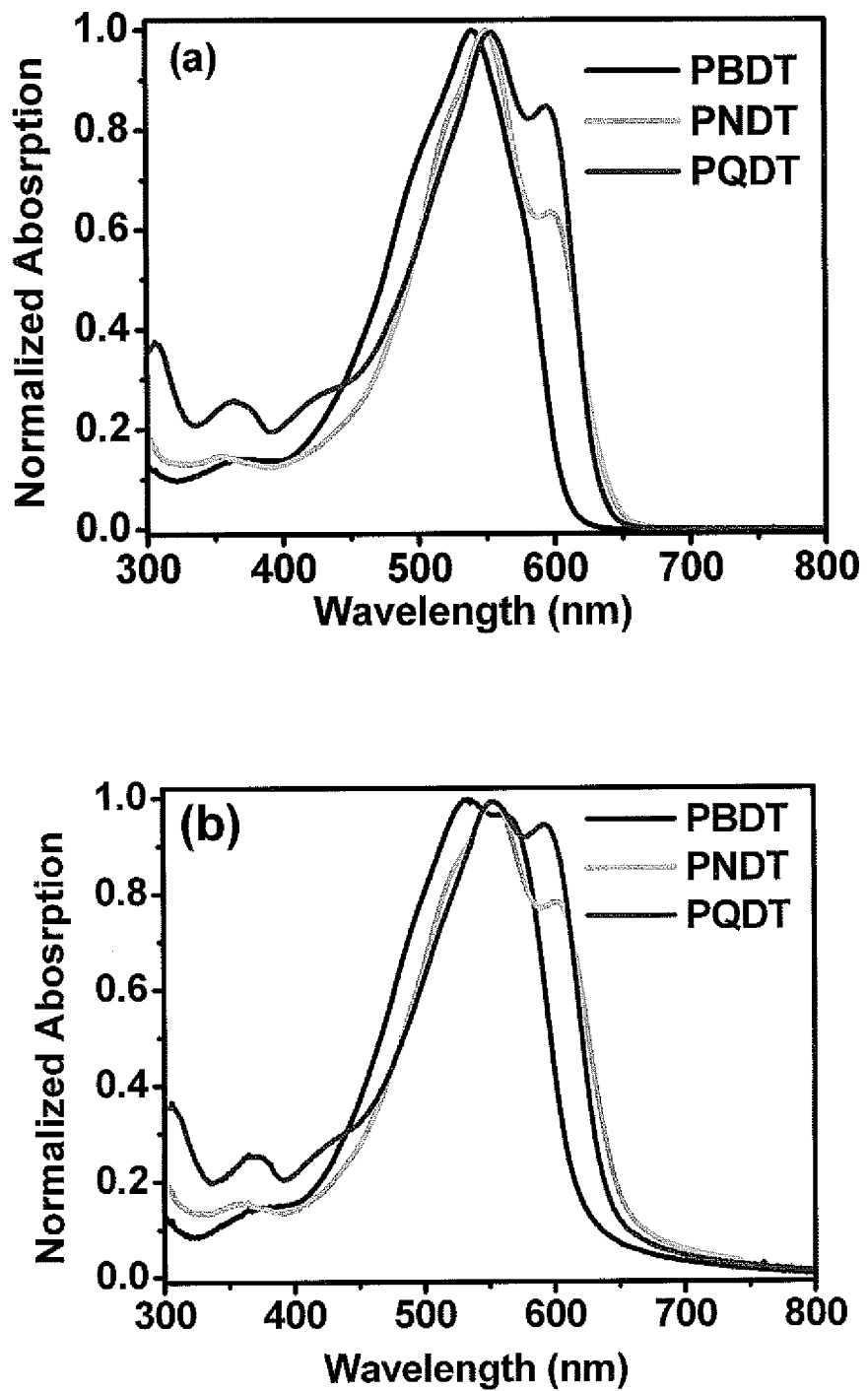
FIG. 3. Normalized UV-Vis absorption spectra of PBDT, PNDT and PQDT in (a) toluene solution and (b) as thin films.
Figure 4:
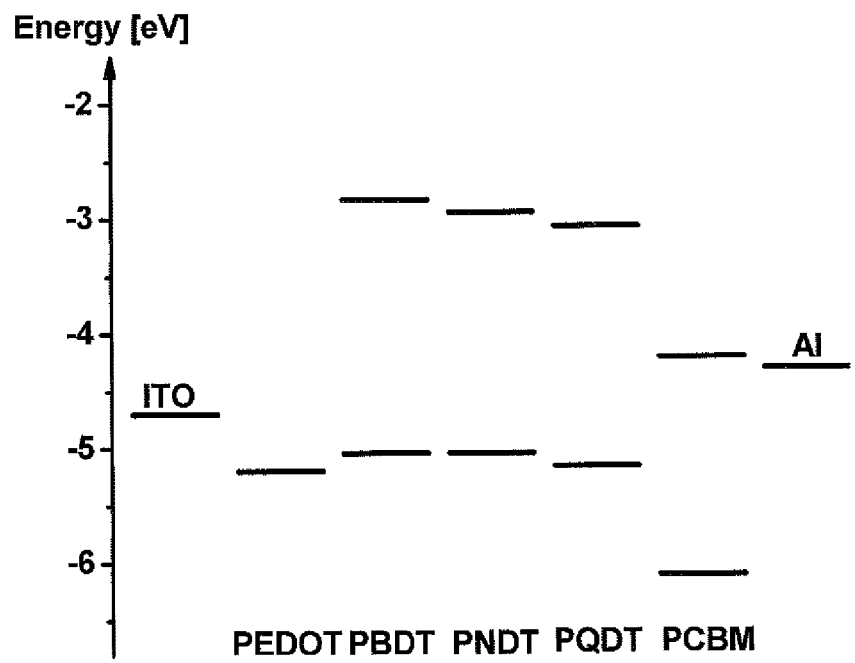
FIG. 4. Energy diagram with HOMO/LUMO levels of PBDT, PNDT, PQDT and PCBM in relation to the work functions of the electrode materials ITO/PEDOT:PSS and Al in a BHJ polymer/PCBM OPV device.

The electronic absorption data of the three alternating copolymers are listed in Table 2. All spectroscopic properties were measured both in toluene solutions (FIG. 3a) and as thin films on glass slides (FIG. 3b). As shown in FIG. 3a, PNDT and PQDT have almost identical absorption maxima at 552 nm, which is 15 nm red-shifted compared to that of PBDT. The low energetic edge of the absorption spectrum of individual polymer was used to approximate the band gap of corresponding polymer. The band gap of PBDT was estimated to be 2.06 eV (absorption edge: ~600 nm), while a smaller band gap of 1.96 eV was calculated for PNDT and PQDT (absorption edge: ~631 nm). Such a decrease in the band gap can be explained by the fact that the naphthalene and quinoxalene units provide more conjugation than the benzene unit when incorporated into the bithiophene unit in the conjugated backbone of copolymers. A similar behavior was observed for the absorption spectra of the three polymers at thin films (FIG. 3b). Unexpectedly, only a tiny red shift (less than 5 nm) was observed for the absorptions from solution to thin film for all copolymers, which suggests less inter-chain stacking induced by π-π interaction.[16] The negligible absorption shift between solution and thin film of three copolymers may be caused by the two octyl groups in 4H-cyclopenta[2,1-b:3,4-b']-dithiophene moiety which imparts steric hindrance and affects the planarity of the conjugated backbone.

Electrochemistry.

Cyclic voltammetry (CV) was employed to investigate the electrochemical properties of the three copolymers and to determine the energy levels of individual copolymers. Cyclic voltammograms of the oxidation and reduction behaviors (supporting information) were recorded from thin films of PBDT, PNDT and PQDT drop-casted from chloroform solutions as described in the experimental section. The potentials were internally calibrated using the ferrocene/ferrocenium redox couple (Fc/Fc$^+$) which has a known reduction potential of 4.8 eV.[26,27] The highest occupied molecular orbital (HOMO) and lowest unoccupied molecular orbital (LUMO) energy levels of copolymers were calculated from the onset oxidation potentials ($E_{onset}^{ox}$) and onset reductive potentials ($E_{onset}^{red}$), respectively, according to equation (1) and (2). The electrochemically determined band gaps were deduced from the difference between onset potentials from oxidation and reduction of copolymers as depicted in equation (3).

$$HOMO = -(E_{onset}^{ox} + 4.8)(eV) \quad (1)$$

$$LUMO = -(E_{onset}^{ox} + 4.8)(eV) \quad (2)$$

$$E_{gap}^{EC} = E_{onset}^{ox} - E_{onset}^{red} \quad (3)$$

The CV data of three copolymers are presented in Table 2. The band gap of PNDT or PQDT with bridged naphtho or quinoxalino segment to bithiophene moiety showed a decrease of ca. 0.1 eV compared to that of PBDT with bridged benzo segment. This behavior is consistent with the results from UV-Vis absorption spectra. However, the HOMO energy level of PNDT remained unchanged as compared to that of PBDT (−5.04 eV). Compared with PBDT and PNDT, PQDT showed a decrease of ca. 0.1 eV in its HOMO energy level (−5.15 eV). The LUMO energy level of PQDT also decreased about 0.1 eV accordingly to maintain a band gap of 2.10 eV. The noticeably lower HOMO and LUMO levels in the case of PQDT, are ascribed to the two nitrogen atoms in the planarized π system, because these two nitrogen atoms render the resulting conjugated molecule more electron-deficient. From these results, we conclude that bridging different π segments with intrinsically different electronic properties to the bithiophene moieties allows a moderate modulation of the band gap and energy level of resulting polymers. This finding will assist future design of semiconductive polymers with tunable electronic properties towards OPV applications.

of 3.61 mA/cm$^2$, a FF of 0.33, leading to the η value of 0.55%, a slightly improved performance relative to PBDT. The same $V_{oc}$ value of PBDT and PNDT based devices can be explained by the identical HOMO energy levels of both polymers (Table 2). Although the hole mobility of PBDT is slightly higher ($3.01 \times 10^{-5}$ cm$^2$ V$^{-1}$ S$^{-1}$) than that of PNDT ($1.3 \times 10^{-5}$ cm$^2$ V$^{-1}$ S$^{-1}$), the broader absorption of PNDT than that of PBDT resulted in higher short circuit current and thus the slightly improved overall efficiency for PNDT based devices. For the BHJ devices made from PQDT:PCBM films (100 nm), the devices exhibited an increased $V_{oc}$ value of 0.53 V, also an increased $J_{sc}$ value of 4.56 mA/cm$^2$ and an improved FF of 0.47, resulting in the significantly improved energy conversion efficiency of 1.14%. The increased $V_{oc}$ value of PQDT based devices is expected since PQDT has a lower HOMO energy level (−5.15 eV) than that of PBDT and PNDT (−5.04

TABLE 2

Optical and electrochemical data of the polymers PBDT, PNDT, PQDT

| | Uv-Vis absorption data | | | | | | Cyclic Voltammetry | | |
|---|---|---|---|---|---|---|---|---|---|
| | toluene solution | | | film | | | $E_{onest}^{ox}$ | $E_{onest}^{red}$ | |
| polymer | $\lambda_{max}$ [nm] | $\lambda_{onset}$ [nm] | $E_g^a$ [eV] | $\lambda_{max}$ [nm] | $\lambda_{onset}$ [nm] | $E_g^a$ [eV] | HOMO [V/eV] | LUMO [V/eV] | $E_{gap}^{EC}$ [eV] |
| PBDT | 538 | 602 | 2.06 | 538 | 617 | 2.00 | 0.24/−5.04 | −1.97/−2.83 | 2.21 |
| PNDT | 552 | 631 | 1.96 | 555 | 650 | 1.91 | 0.24/−5.04 | −1.86/−2.94 | 2.10 |
| PQDT | 554 | 631 | 1.96 | 555 | 641 | 1.94 | 0.35/−5.15 | −1.75/−3.05 | 2.10 |

$^a$ Calculated from the intersection of the tangent on the low energetic edge of the absorption spectrum with the abscissa.

Photovoltaic Properties.

Figure 5:
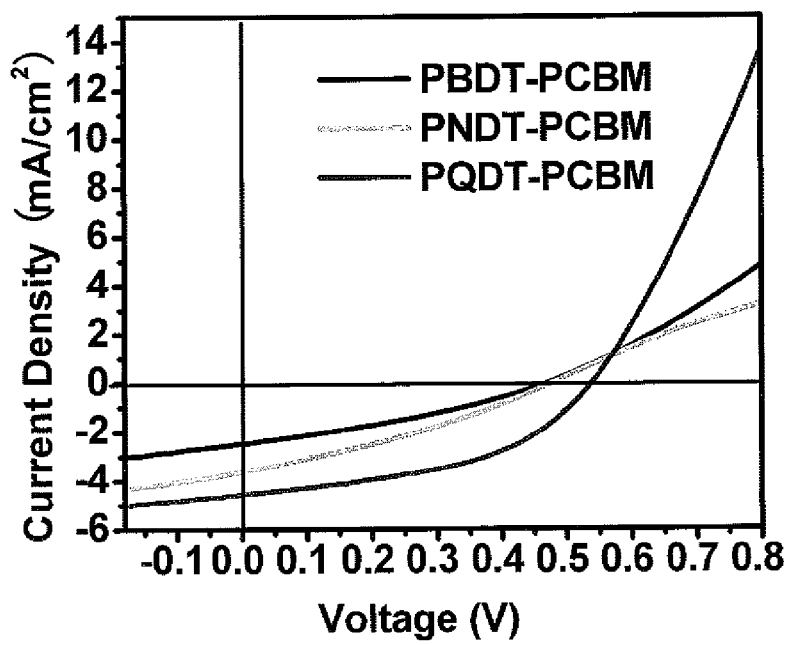
FIG. 5. Typical I-V characteristics (AM 1.5G, 100 mW/cm$^2$) of ITO/PEDOT:PSS(45 nm)/copolymer:PCBM (1:1.6, w/w)/Al(100 nm) devices.

PCBM as the electron accepting component has been widely used in OPV devices. FIG. 5 exhibits a diagram of energy levels of three alternating copolymers in relation to that of PCBM, and the work functions of indium tin oxide (ITO), poly(3,4-ethylenedioxythiophene) poly(styrenesulfonate) (PEDOT:PSS) and aluminum (Al) used as electrodes in an OPV device. The LUMO energy levels of three copolymers are distinctively higher than that of PCBM. The difference between the LUMO energy levels of three copolymers and PCBM is over 1.2 eV, which is sufficiently high to enable an unrestricted and directed charge transfer.[28] Thus, all three copolymers were applied as donors into a conventional BHJ type OPV device with PCBM as acceptor in order to investigate the effect of different bridging π segments within the bithiophene moiety on the photovoltaic properties.

Hole mobility values for all copolymers were estimated via space-charge limit current (SCLC) by fabricating a hole-only device according to Blom's device configuration[29,30] as detailed in the experimental section. The hole mobilities were found to be $3.01 \times 10^{-5}$ cm$^2$ V$^{-1}$S$^{-1}$, $1.3 \times 10^{-5}$ cm$^2$ V$^{-1}$ S$^{-1}$, $5.15 \times 10^{-5}$ cm$^2$ V$^{-1}$ S$^{-1}$ for PBDT, PNDT, and PQDT respectively.

Typical I-V characteristics of ITO/PEDOT:PSS/copolymer:PCBM (1:1.6, w/w)/Al devices are depicted in FIG. 5 under AM 1.5G irradiation (100 mW/cm$^2$). The devices with PBDT:PCBM layers (90 nm) showed an open circuit voltage ($V_{oc}$) of 0.47 V, a short circuit current density (4) of 2.47 mA/cm$^2$, and a fill factor (FF) of 0.32, giving an energy conversion efficiency (η) of 0.38%. The $V_{oc}$ value is close to the difference (0.82 V) between the HOMO energy level of PBDT and LUMO energy level of PCBM after the correction for an expected voltage loss of around 0.2 V at each electrode due to band bending.[31] The devices with PNDT:PCBM blends (90 nm) demonstrated a $V_{oc}$ value of 0.47 V, a $J_{sc}$ value eV). The increased current relative to that of PNDT is ascribed mainly to the fact that PQDT has higher hole mobility than that of PNDT since both polymers have the same band gap (2.10 eV). Tapping-mode atomic force microscopy (AFM) studies were carried out to investigate the film morphology of polymer:PCBM blends on their photovoltaic performances. Rough surfaces and blend phase separation were observed for PBDT:PCBM and PNDT:PCBM films (supporting information) compared to relatively smooth surface and more intimate mixing for PQDT:PCBM layer, which somehow explained better hole mobility of PQDT in devices over PBDT and PNDT. The improved miscibility of PQDT and PCBM, together with the higher $V_{oc}$ value and smaller band gap, leads to the improved overall energy conversion efficiency.

Figure 6:
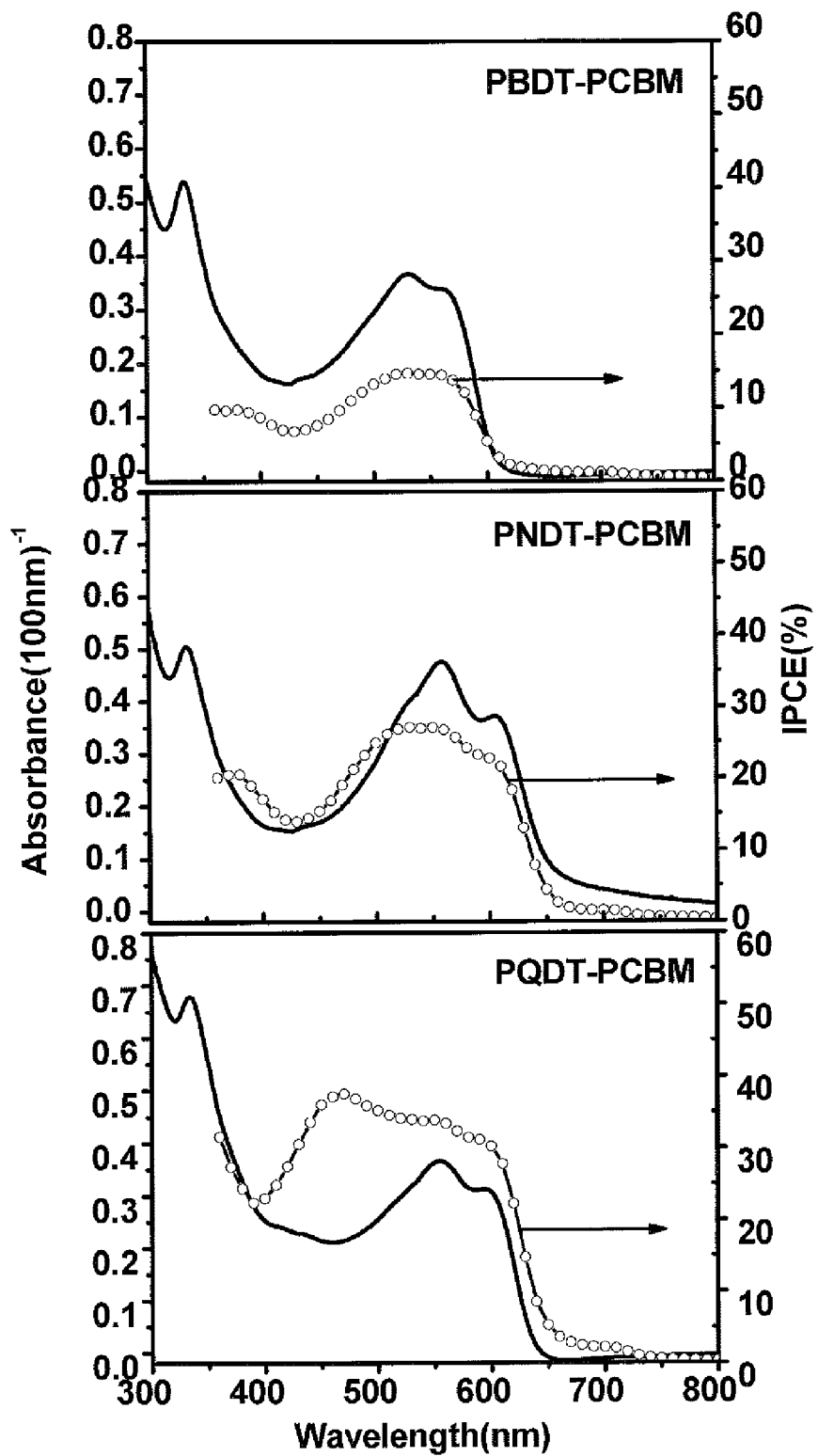
FIG. 6. IPCE spectra (gray circled line) of BHJ photovoltaic devices ITO/PEDOT:PSS (45 nm)/copolymer:PCBM (1:1.6, w/w)/Al (100 nm) and the optical absorptions for the corresponding films of the blend from polymers and PCBM (black solid line) with the thickness of 100 nm.

The incident-photon-to-current efficiency (IPCE) spectra of the photovoltaic devices from copolymer:PCBM blends are presented in FIG. 6 together with the absorption of thin films from copolymer: PCBM blends. The IPCE spectra of PBDT and PNDT match the optical absorptions well and show the maximum of 15% at 538 nm for PBDT and 27% at 555 nm for PNDT, respectively. For PBDT, a broad plateau around the maximum in IPCE spectrum exists between 500 and 580 nm, while occurring between 480 and 620 nm for PNDT. This phenomenon was caused by the stronger and wider absorption of PNDT:PCBM blend between 450 and 700 nm than that for PBDT:PCBM at the same film thickness. A similar match is found between the absorption spectrum and the IPCE spectrum for PQDT:PCBM films. The IPCE spectrum shows a maximum of 37% at 460 nm and an average value of 33% in the absorption area from 430 to 620 nm for devices based on PQDT:PCBM films. The higher IPCE value over the entire absorption wavelength region further explained the improved photovoltaic performance of PQDT: PCBM over the blends of the other two copolymers with PCBM.

Conclusions.

We have successfully synthesized three alternating copolymers based on 4H-cyclopenta[2,1-b:3,4-b']dithiophene as the common unit, while employing different structurally related conjugated units, namely, benzo[2,1-b:3,4-b']dithiophene (PBDT), naphtho[2,1-b:3,4-b']dithiophene (PNDT) and quinoxalino[2,1-b:3,4-b]dithiophene (PQDT). By bridging intrinsically different π system to bithophene moiety to obtain enhanced π-electron delocalization and incorporating them into semiconductive alternating copolymers, the band gap, the HOMO and LUMO energy levels of resulting copolymers can be fine-tuned as demonstrated from the investigation of optical absorption properties and electrochemical studies of PBDT, PNDT and PQDT. The three copolymers were applied as electron-donating materials with PCBM as acceptor in conventional BM photovoltaic devices. A peak IPCE value of 37% and an overall power conversion efficiency of 1.14% was obtained from a PQDT/PCBM blend device, which is very encouraging given the quite large band gap of 2.1 eV for PQDT. Although the energy conversion efficiencies for these un-optimized photovoltaic devices are still not sufficiently high, this study enriched our understanding of tuning the electronic properties of conjugated semiconductive polymers for photovoltaic applications and provided further insights for future materials design.

Experimental Section

Reagents and Instrumentation.

All reagents and chemicals were purchased from commercial sources (Aldrich, Acros, Strem, Fluka) and used without further purification unless stated otherwise. Reagent grade solvents were dried when necessary and purified by distillation. Melting points were uncorrected. Elemental analysis was carried out at the Atlantic Microlab. Gel permeation chromatography (GPC) measurements were performed on a Waters 2695 Separations Module apparatus with a differential refractive index detector with tetrahydrofuran (THF) as eluent. The obtained molecular weight is relative to the polystyrene standard. Thermogravimetric analysis (TGA) measurements were carried out with a PerkinElmer thermogravimetric analyzer (Pyris 1 TGA) at a heating rate of 10° C. min$^{-1}$ under a nitrogen atmosphere. The temperature of degradation ($T_d$) is correlated to a 5% weight loss. Differential scanning calorimetry (DSC) analyses were recorded on a DSC220C instrument from SIT Seiko Instruments. $^1$H nuclear magnetic resonance (NMR) measurements were recorded either with a Bruker Avance 300 MHz AMX or Bruker 400 MHz DRX spectrometer. $^{13}$C nuclear magnetic resonance (NMR) measurements were carried out with a Broker 400 MHz DRX spectrometer. Chemical shifts were expressed in parts per million (ppm), and splitting patterns are designated as s (singlet), d (doublet), t (triplet) and m (multiplet). Coupling constants J are reported in Hertz (Hz). The mass spectroscopy was carried out on Micromass Quattro II Triple Quadrupole Mass Spectrometer. 3,3'-diiodo-2,2'-bithiophene,[22] 4,4-dioctyl-4H-cyclopenta[2,1-b:3,4-b']dithiophene,[32] and benzo[2,1-b:3,4-b']bithiophene-4,5-quinone (5)[33,34] were synthesized according to literature procedures.

Electrochemistry.

Cyclic voltammetry measurements were carried out using a Bioanalytical Systems (BAS) Epsilon potentiostat equipped with a standard three-electrode configuration. Typically, a three electrodes cell equipped with a glassy carbon working electrode, a Ag/AgNO$_3$ (0.01 M in anhydrous acetonitrile) reference electrode, and a Pt wire counter electrode was employed. The measurements were done in anhydrous acetonitrile with tetrabutyl ammonium hexafluorophosphate (0.1 M) as the supporting electrolyte under an argon atmosphere at a scan rate of 100 mV/s. Polymer films were drop cast onto the glassy carbon working electrode from a 2.5 mg/mL chloroform solution and dried under house nitrogen stream prior to measurements. The potential of Ag/AgNO$_3$ reference electrode was internally calibrated by using the ferrocene/ferrocenium redox couple (Fc/Fc$^+$). The electrochemical onsets were determined at the position where the current starts to differ from the baseline.

Spectroscopy.

UV-Visible absorption spectra were obtained by a Shimadzu UV-2401PC spectrophotometer. Fluorescence spectra were recorded on a Shimadzu RF-5301PC spectrofluorophotometer. For the measurements of thin films, polymers were spin-coated onto pre-cleaned glass slides from 10 mg/mL polymer solutions in chlorobenzene.

AFM.

Tapping mode with a Nanoscope III AFM (Digital Instruments, Inc., Santa Barbara, Calif.), The measurements were performed at ambient conditions (in air, 20° C.) using Si cantilevers with a spring constant of ~50 N/m, a tip radius of 8 nm, and a resonance frequency of about 300 kHz.

Polymer Solar Cell Fabrication and Testing.

Glass substrates coated with patterned indium-doped tin oxide (ITO) were purchased from Thin Film Devices, Inc. The 150 nm sputtered ITO pattern had a resistivity of 15Ω/□. Prior to use, the substrates were ultrasonicated for 10 minutes in deionized water followed by the rinse with deionized water and the treatment in acetone and then 2-propanol in the same way. The substrates were dried under a stream of nitrogen and subjected to the treatment of UV-Ozone over 20 minutes. A filtered dispersion of PEDOT:PSS in water (Baytron-PH500) was then spin-coated onto clean ITO substrates under 4000 rpm for 60 seconds and then baked at 130° C. for 15 minutes to give a thin film with a thickness of 45 nm. A blend of polymer and PCBM (1:1.6 w/w, 10 mg/mL for polymers) was dissolved in chlorobenzene with heating at 60° C. for 2 hours, filtered through a 0.45 μm poly(tetrafluoroethylene) (PTFE) filter, spin-coated at 1200 rpm for 60 seconds onto PEDOT:PSS layer. The substrates were then dried under vacuum at room temperature for 12 hours. The thicknesses of films were recorded by a profilometer (Alpha-Step 200, Tencor Instruments). The devices were finished for measurement after thermal deposition of 100 nm aluminum film as the cathode at a pressure of ~1×10$^{-6}$ mbar. There are 8 devices per substrate, with an active area of 18 mm$^2$ per device. Device characterization was carried out under AM 1.5G irradiation with the intensity of 100 mW/m$^2$ (Oriel 91160, 300 W) calibrated by a NREL certified standard silicon cell. Current versus potential (I-V) curves were recorded with a Keithley 2400 digital source meter. IPCE were detected under monochromatic illumination (Oriel Cornerstone 260¼ m monochromator equipped with Oriel 70613NS QTH lamp) and the calibration of the incident light was performed with a monocrystalline silicon diode. All fabrication steps after adding the PEDOT:PSS layer onto ITO substrate, and characterizations were performed in gloveboxes under nitrogen atmosphere. For mobility measurements, the hole-only devices in a configuration of ITO/PEDOT:PSS (45 nm)/copolymer-PCBM (1:1.6, w/w)/Pd (40 nm) were fabricated. The experimental dark current densities J of polymer: PCBM blends were measured when applied with voltage from 0 to 6V. The applied voltage V was corrected from the built-in voltage $V_{bi}$[30] which was taken as a compensation voltage $V_{bi}=V_{oc}+0.05$ V and the voltage drop $V_{rs}$ across the indium tin oxide/poly(3,4-ethylene-dioxythiophene):poly(styrene sulfonic acid) (ITO/PEDOT:PSS) series resistance and contact resistance, which is found to be around 35Ω from a reference device without the polymer layer. From the plots of $J^{0.5}$ vs. V (supporting information), hole mobilities of copolymers can be deduced from[35]

$$J = \frac{9}{8}\varepsilon_r \varepsilon_0 \mu_h \frac{V^2}{L^3} \quad (4)$$

where $\varepsilon_0$ is the permittivity of free space, $\varepsilon_r$ is the dielectric constant of the polymer which is assumed to be around 3 for the conjugated polymers in our experiment,[36] $\mu_h$ is the hole mobility, V is the voltage drop across the device, and L is the film thickness of active layer.

Synthesis (6S,11S)-9-hydroxy-2,6,11,15-tetramethylhexadeca-2,14-dien-8-one (1).[37]

To a 250 mL of two-necked round-bottom (RB) flask containing (−) citronellal (25.0 g, 163 mmol) in 50 mL of ethanol under argon was added the catalyst of 3-ethyl-5-(2-hydroxyethyl)-4-methylthiazolium bromide (4.1 g, 16.3 mmol) and triethylamine (17.0 mL, 120 mmol). The mixture was then heated to reflux over night. After removal of the solvent under reduced pressure, the resulted mixture was poured into 100 mL of water and extracted by ethyl ether (3×60 mL). The combined organic layer was dried over anhydrous $MgSO_4$ and concentrated under vacuum. The residue was purified by flash chromatography on silica gel (hexane:ethyl acetate=20:1, v/v) to afford 18.5 g of product as a colorless oil (yield: 75%). $^1H$ NMR (400 MHz, $CDCl_3$) δ 5.08 (m, 2H), 4.15 (m, 1H), 3.47 (dd, 1H, J=5.04 Hz), 2.40 (m, 1H), 2.2 (m, 1H), 1.9-2.1 (m, 6H), 1.60 (d, 12H), 1.1-1.3 (m, 4H), 0.8-1.0 (m, 6H). $^{13}C$ NMR (400 MHz, $CDCl_3$) δ 212.63, 131.63, 131.30, 124.52, 124.40, 124.00, 75.59, 74.70, 45.16, 45.15, 41.15, 41.00, 37.95, 36.85, 36.83, 35.56, 29.36, 29.04, 28.92, 28.81, 25.65, 25.42, 25.39, 25.36, 25.22, 20.29, 19.82, 19.65, 18.46, 17.60.

(6S,11S)-2,6,11,15-tetramethylhexadeca-2,14-diene-8,9-dione (2).

To a solution of (7.0 g, 22.7 mmol) in 100 mL of methylene chloride was added 7.5 g of PCC. The mixture was heated to reflux. After 16 hours, the mixture was cooled to room temperature and filtered. The solution was concentrated under reduced pressure. The crude compound was purified by flash chromatography on silica gel (hexane:ethyl acetate=20:1, v/v) to afford the product as a colorless oil. Yield: 3.5 g (50%). $^1H$ NMR (400 MHz, $CDCl_3$) δ 5.06 (m, 2H), 2.66-2.74 (dd, 2H, J=5.64, 16.71 Hz), 2.51-2.60 (dd, 2H, J=7.98, 16.73 Hz), 1.92-2.02 (m, 6H), 1.5-1.67 (s, 6H), 1.58 (s, 6H), 1.19-1.35 (m, 4H), 0.89 (d, 6H, J=6.66 Hz). $^{13}C$ NMR (400 MHz, $CDCl_3$) δ 200.05, 131.60, 124.07, 52.96, 36.94, 28.49, 25.66, 25.36, 19.71, 17.60.

(6S,11S)-2,6,11,15-tetramethylhexadeca-2,14-diene-8,9-dione dioxime (3).

A 250 mL of two-necked RB flask containing a solution of 2 (6.12 g, 20.0 mmol) in ethanol (60 mL) and pyridine (8.0 mL) was purged with argon. Hydroxyammonium chloride (7.0 g, 100.0 mmol) was then added in one portion. The mixture was heated to reflux for 5 hours. After removal of the solvent under reduced pressure, 100 mL of water/ethanol (2:1, v/v) was added and ultrasonicated before filtration. The solid was then rinsed by 20 mL of cold hexane and dried under vacuum to afford a white pure solid. Yield: 5.5 g (95%). mp: 131-131.6° C. $^1H$ NMR (400 MHz, $CD_3OD$) δ 4.93 (m, 2H), 3.16 (m, 2H), 2.32-2.47 (m, 4H), 1.72-1.90 (m, 6H), 1.51 (s, 6H), 1.44 (s, 6H), 1.17-1.20 (m, 2H), 1.01-1.05 (m, 2H), 0.72 (d, 6H, J=6.7 Hz). $^{13}C$ NMR (400 MHz, $CD_3OD$) 157.95, 131.66, 126.05, 38.51, 32.19, 31.42, 26.68, 25.86, 20.16, 17.68.

(6S,11S)-2,6,11,15-tetramethylhexadecane-8,9-diamine dihydrogen chloride (4).

To a solution of 3 (1.9 g) in 50 mL of absolute ethanol at room temperature was added platinum oxide (0.4 g) and 2.0 mL of concentrated hydrogen chloride. The mixture was then purged with hydrogen and was kept stirring under hydrogen (with a hydrogen balloon) over 10 hours. After removing the solvent under reduced pressure, the residue was rinsed with cold hexane and directly used in the next step without further purification.

2,3-bis((S)-2,6-dimethylheptyl)dithieno[3,2-f:2',3'-h]quinoxaline (6).

To a 100 mL of two-necked RB flask equipped with a condenser was added the solution of 4 (1.20 g) in 50 mL of methanol, 5 (0.66 g, 3 mmol) and 2.0 mL of pyridine. The mixture was then heated to reflux with stirring over night. After removing the solvent under reduced pressure, the residue was re-dissolved in 30 mL of methylene chloride and washed by water and dried over anhydrous $MgSO_4$. The organic layer was then concentrated and the residue was purified by flash chromatography on silica gel (hexane:methylene chloride=4:1, v/v) to afford 0.91 g of pure product as a white solid (yield: 60%). mp: 57.5-58.7° C. $^1H$ NMR (300 MHz, $CDCl_3$) δ 8.31 (d, 2H, J=5.28 Hz), 7.51 (d, 2H, J=5.22 Hz), 2.94-3.16 (dd, 2H, J=6.08 Hz, 14.2 Hz), 2.87-2.90 (dd, 2H, J=8.0 Hz, 14.2 Hz), 2.33 (m, 2H), 1.55 (m, 2H), 1.2-1.52 (m, 12H), 1.03 (d, 6H, J=6.58 Hz). 0.88 (d, 12H, J=7.45 Hz). $^{13}C$ NMR (400 MHz, $CDCl_3$) δ 154.06, 136.04, 135.11, 133.95, 124.12, 42.13, 39.23, 37.36, 32.91, 27.98, 24.87, 22.71, 22.59, 19.82. MS: m/z=496.6 $[M+2H]^+$ (Calcd.: 494.3)

6,9-dibromo-2,3-bis((S)-2,6-dimethylheptyl)dithieno[3,2-f:2',3'-h]quinoxaline (7).

To a solution of 6 (0.99 g, 2.0 mmol) in 20 mL of chloroform/acetic acid (1:1, v/v) at room temperature was added NBS (0.75 g, 4.2 mmol). The resulting mixture was stirred at room temperature for 24 hours and then diluted by 50 mL of water. The organic layer was washed by 5% sodium hydroxide solution, water and brine and dried over anhydrous $MgSO_4$. After removing the solvent, the crude product was further purified by flash chromatography on silica gel (hexane:methylene chloride=5:1, v/v) to afford 0.85 g of pure product as a white solid (yield: 65%). mp: 106.4-107.9° C. $^1H$ NMR (300 MHz, $CDCl_3$) δ 8.15 (s, 2H), 3.00-3.07 (dd, 2H, J=6.05 Hz, 14.38 Hz), 2.78-2.85 (dd, 2H, J=7.96 Hz, 14.38 Hz), 2.28 (m, 2H), 1.55 (m, 2H), 1.17-1.45 (m, 12H), 0.98 (d, 6H, J=6.60 Hz). 0.88 (d, 12H, J=6.58 Hz). $^{13}C$ NMR (400 MHz, $CDCl_3$) δ 155.12, 135.13, 134.73, 133.60, 126.73, 112.97, 42.17, 39.27, 37.39, 32.73, 28.03, 24.88, 22.73,

2,6-Bis(4,4,5,5-tetramethyl-1,3,2-dioxaborolan-2-yl)-4,4-dioctyl-4H-cyclopenta[2,1-b:3,4-b'] dithiophene (8).

A solution of 4,4-dioctyl-4H-cyclopenta[2,1-b:3,4-b'] dithiophene (1.2 g, 3.0 mmol) in 20 mL of dry THF under argon was cooled to −78° C., and n-BuLi in hexane (2.5 M, 4.8 mL, 12 mmol) was added over 10 min with stirring. The mixture was kept at −78° C. for another 1 hour before 2-isopropoxy-4,4,5,5-tetramethyl[1,3,2]dioxaborolane (3.2 mL, 25 mmol) Was added. The cooling bath was removed after 3 hours and the mixture was allowed to warm to room temperature overnight (16 h). After subsequent dilution with ethyl ether and washing with brine and large amount of water, the organic layer was dried over anhydrous $MgSO_4$, and concentrated under reduced pressure to give a solid which was washed further with cold methanol and dried in vacuo to afford the pure product as a pale yellow solid (1.4 g, 71%). mp: 109-110° C. $^1$H NMR (300 MHz, $CDCl_3$): δ 7.42 (s, 2H), 1.79 (m, 4H), 1.36 (s, 24H), 1.1-1.24 (m, 10H), 0.90-0.93 (m, 4H), 0.84 (t, 6H, J=7.08 Hz). $^{13}$C NMR (400 MHz, $CDCl_3$): δ 161.41, 143.84, 131.04, 83.97, 52.74, 37.79, 31.75, 29.99, 29.24, 24.76, 24.46, 22.56, 14.02. MS: m/z=654.6 $[M]^+$ (Calcd.: 654.4). Anal. Calcd. for $C_{37}H_{60}B_2O_4S_2$: C, 67.89; H, 9.24; S, 9.80. Found: C, 68.05; H, 9.41; S, 9.72.

4,5-dioctylbenzo[2,1-b:3,4-b']dithiophene.[23]

To a two-necked RB flask under nitrogen was added 1.39 g (3.3 mmol) of 3,3'-diiodo-2,2'-bithiophene, 222 mg (0.33 mmol) of $Pd(OAc)_2$, 2.5 g (10 mmol) of 9-octadecyne, tributyl amine 1.85 g (10 mmol), and 10 mL of anhydrous DMF. The mixture was heated at 130° C. for 4 hours. After cooling down to room temperature, 50 mL of ether ethyl was. The organic phase was washed with water several times, dried by $MgSO_4$, concentrated under reduced pressure. The residue was further purified by flash chromatography on silica gel (hexane as eluent) to afford the pure product as a colorless liquid (1.16 g, yield: 85%). $^1$H NMR (300 MHz, $CDCl_3$) δ 7.46 (d, 2H, J=5.43 Hz), 7.37 (d, 2H, J=5.42 Hz), 3.01 (t, 4H, J=7.89 Hz), 1.68 (m, 4H), 1.51 (m, 4H), 1.30 (m, 16H), 0.89 (t, 6H, J=6.7 Hz). $^{13}$C NMR (400 MHz, $CDCl_3$) δ 137.47, 131.58, 131.32, 123.55, 123.38, 31.87, 31.52, 30.43, 30.16, 29.48, 29.27, 22.63, 14.04. MS: m/z=414.7 $[M]^+$ (Calcd.: 414.7).

2,7-dibromo-4,5-dioctylbenzo[2,1-b:3,4-b'] dithiophene

To a solution of 4,5-dioctylbenzo[2,1-b:3,4-b']dithiophene (0.83 g, 2 mmol) in 10 mL of chloroform/glacial acetic acid (1:1, v/v) was added 0.72 g of NBS at room temperature. After the reaction was completed, 20 mL of chloroform was added. The mixture was then washed by water, 5% NaOH and brine. After drying with anhydrous $MgSO_4$, the organic phase was concentrated and the residue was further purified by flash chromatography on silica gel (hexane as eluent) to give 0.8 g final product (yield: 70%). mp: 63.8-65.2° C. $^1$H NMR (300 MHz, $CDCl_3$) δ 7.39 (s, 2H), 2.88 (t, 4H, J=8.25 Hz), 1.58 (m, 4H), 1.48 (m, 4H), 1.32 (m, 16H), 0.89 (t, 6H, J=6.9 Hz). $^{13}$C NMR (400 MHz, $CDCl_3$) δ 137.28, 131.46, 131.40, 126.26, 112.53, 31.89, 31.41, 30.36, 30.10, 29.44, 29.28, 22.67, 22.61, 19.86. MS: m/z=652.6 [M+2H] (Calcd.: 650.1). Anal. Calcd. for $C_{30}H_{40}Br_2N_2S_2$: C, 55.21; H, 6.18; Br, 24.49; N, 4.29; S, 9.83. Found: C, 55.49; H, 6.24; Br, 24.59; N, 4.18; S, 9.78.

14.08. MS: m/z=572.6 $[M]^+$ (Calcd.: 572.5). Anal. Calcd. for $C_{26}H_{36}Br_2S_2$: C, 54.55; H, 6.34; Br, 27.91; S, 11.20. Found: C, 54.75; H, 6.32; Br, 27.89; S, 11.35.

1,2-dioctylbenzene.

The synthesis of 1,2-dioctylbenzene and 4,5-dioctyyl-1,2-diiodobenzene was adopted from the reported procedure.[38] A flame dried, 250 mL of three-necked RB flask equipped with a condenser and an addition funnel was loaded with magnesium metal turnings (12.0 g, 0.48 mol) in 20 mL of anhydrous ethyl ether under an argon atmosphere. A solution of 1-bromooctane (80.5 mL, 0.46 mol) in 50 mL of anhydrous ethyl ether was added dropwise in a rate that a gentle reflux was maintained. After the addition of the bromide solution, the resulting mixture was heated under reflux for additional 2 hours. After cooling to room temperature, the clear solution of the Grignard reagent was transferred through a cannula into a flame dried addition funnel and added dropwise to a stirred solution of 1,2-dichlorobenzene (23 mL, 0.2 mol) and 1,3-bis(diphenylphosphino)propane)-nickel(II) chloride (0.7 g, 1.29 mmol) in 50 mL of anhydrous ethyl ether at room temperature. The reaction mixture was then heated to reflux overnight and then cooled to room temperature and poured into 200 mL of hydrochloric acid (2 M) with ice. The organic layer was separated and washed with water, $Na_2CO_3$, brine and water and dried over anhydrous $MgSO_4$. After removing the solvent under reduced pressure, the residue was purified by passing through a short silica gel column (hexane as eluent). The distillation of the resulting oil under reduced pressure gave 39.0 g of pure 1,2-dioctyllbenzene (138° C./0.25 mmHg) as a colorless liquid (yield: 65%). $^1$H NMR (400 MHz, $CDCl_3$) δ 7.12 (m, 4H), 2.59 (t, 4H, J=7.76 Hz), 1.56 (m, 4H), 1.27-1.37 (m, 20H), 0.88 (t, 6H, J=6.36 Hz). $^{13}$C NMR (400 MHz, $CDCl_3$) δ 140.56, 129.08, 125.66, 32.69, 31.90, 31.35, 29.81, 29.51, 29.28, 22.68, 14.11. MS: m/z=302.3 $[M]^+$ (Calcd.: 302.3).

4,5-dioctyl-1,2-diiodobenzene.

1,2-Dioctylbenzene (12.3 g, 40.6 mol) was added to a RB flask loaded with glacial acetic acid (150 mL), $H_2SO_4$ (coned, 9.0 mL), $H_2O$ (1 mL), $NaIO_3$ (4.016 g, 20.3 mmol), and $I_2$ (11.34 g, 44.7 mmol) at room temperature. The resulting mixture was then heated under reflux overnight. After cooling to room temperature, a saturated aqueous $Na_2S_2O_4$ solution was added until the color of the mixture changed from purple to light brown. The mixture was then extracted with $CH_2Cl_2$ (50 mL×3), washed with saturated $Na_2S_2O_4$, $H_2O$, and brine, and then dried over anhydrous $Na_2SO_4$. After removing the solvent under reduced pressure, the brownish residue was purified by flash chromatography on silica gel to afford a colorless oil (18.7 g, yield: 83%). $^1$H NMR (400 MHz, $CDCl_3$) δ 7.60 (s, 2H), 2.46 (t, 4H, J=8.0 Hz), 1.52 (m, 4H), 1.27-1.37 (m, 20H), 0.88 (t, 6H, J=7.04 Hz). $^{13}$C NMR (400 MHz, $CDCl_3$) δ 142.62, 139.69, 103.97, 31.87, 31.80, 30.85, 29.54, 29.35, 29.16, 22.60, 14.05. MS: m/z=554.1 $[M]^+$ (Calcd.: 554.1).

4,5-Bis(3-thienyl)-1,2-dioctylbenzene.[18]

To a three-necked 250 mL RB flask equipped with a condenser was added 4,5-dioctyl-1,2-diiodobenzene (11.08 g, 20 mmol), 3-thiophene boronic acid (6.4 g, 50.0 mmol), $Na_2CO_3$ (24.0 g, 226 mmol) in a mixed solvent of toluene (50 mL), EtOH (50 mL), and $H_2O$ (50 mL). The resulting mixture was vigorously stirred during the cycle of evacuation/refilling with argon three times. The catalyst Pd(PPh$_3$)$_4$ (1% equiv., 575 mg, 0.54 mmol) was then added to the mixture under a gentle argon stream and the system was heated at reflux overnight. After cooling to room temperature, the reaction mixture was diluted with 100 mL of ethyl ether and the aqueous layer was removed. The organic layer was washed with water, brine and dried with anhydrous MgSO$_4$. After the solvent removal under reduced pressure, the residue was purified by flash chromatography on silica gel (hexane:ethyl acetate=20:1, v/v) to provide 7.2 g of the product (yield: 78%). $^1$H NMR (400 MHz, CDCl$_3$) δ 7.25 (s, 2H), 7.17 (dd, 2H), J=4.92 Hz, 2.98 Hz), 7.05 (dd, 2H), J=1.22 Hz, 2.97 Hz), 6.80 (dd, 2H, J=1.23 Hz, 4.94 Hz), 2.66 (t, 4H), J=7.80 Hz), 1.65 (m, 4H), 1.30-1.50 (m, 20H), 0.90 (t, 6H, J=6.96 Hz). $^{13}$C NMR (400 MHz, CDCl$_3$) δ 142.20, 140.03, 132.65, 130.92, 129.08, 124.39, 122.38, 32.45, 31.91, 31.40, 29.88, 29.51, 29.29, 22.68, 14.13. MS: m/z=466.3 [M]$^+$ (Calcd.: 466.2).

5,6-Dioctylnaphtho[2,1-b:3,4-b']dithiophene.

In a quartz tube was added a solution of 4,5-bis(3-thienyl)-1,2-dioctylbenzene (0.5 g, 1.1 mmol) and iodine (30 mg) in toluene (500 mL). The system was then irradiated by a 400 W mercury lamp equipped with an efficient cooling system for 16 hours under magnetic stirring and air bubbling. The reaction mixture was washed with a saturated aqueous solution of Na$_2$S$_2$O$_3$, dried over MgSO$_4$ and concentrated. The residue was purified by flash chromatography on silica gel (hexane as eluent), and a white solid was obtained (0.33 g, yield: 65%). mp: 62.2-63.1° C. $^1$H NMR (400 MHz, CDCl$_3$) δ 8.11 (s, 2H), 7.97 (d, 2H), J=5.34 Hz), 7.47 (d, 2H, J=5.30), 2.86 (t, 4H, J=7.76 Hz), 1.74 (m, 4H), 1.32-1.50 (m, 20H), 0.92 (t, 6H, J=6.80 Hz). $^{13}$C NMR (400 MHz, CDCl$_3$) δ 139.22, 134.12, 131.25, 126.09, 124.04, 123.34, 122.74, 33.14, 31.29, 31.52, 29.86, 29.58, 29.34, 22.70, 14.14. MS: m/z=464.4 [M]$^+$ (Calcd.: 464.2).

2,9-dibromo-5,6-dioctylnaphthe[2,1-b:3,4-b']dithiophene.

To a stirred solution of 5,6-dioctylnaphtho[2,1-b:3,4-b']dithiophene (1 g, 2.16 mmol) in a mixture of chloroform-acetic acid (1/1, v/v, 10 mL) at room temperature was added NBS (0.773 g, 4.3 mmol). The resulting solution was stirred overnight. The mixture was poured into 100 mL of water and extracted with chloroform (50 mL). The combined organic layer was further washed with 5% aqueous NaOH solution, brine and water, dried with MgSO$_4$, and was concentrated under reduced pressure. The residue was purified by flash chromatography on silica gel to give 0.92 g of the pure product (yield: 68%). mp: 105.3-106.4° C. $^1$H NMR (400 MHz, CDCl$_3$) δ 7.84 (s, 2H), 7.80 (d, 2H), 2.79 (m, 4H, J=7.63 Hz), 1.70 (m, 4H), 1.31-1.48 (m, 20H), 0.91 (t, 6H, J=6.91 Hz). $^{13}$C NMR (400 MHz, CDCl$_3$) δ 139.84, 133.84, 130.90, 125.51, 124.90, 123.64, 111.98, 33.08, 31.93, 31.31, 29.88, 29.57, 29.35, 22.71, 14.14. MS: m/z=620.2 [M]$^+$ (Calcd.: 620.0). Anal. Calcd for C$_{30}$H$_{38}$Br$_2$S$_2$: C, 57.88; H, 6.15; Br, 25.67; S, 10.30. Found: C, 57.97; H, 6.20; Br, 25.84; S, 10.38.

Synthesis of Alternating Copolymers Via Suzuki Coupling Polymerization.

A representative procedure is as follows. To a flame dried 25 mL of two-necked RB flask equipped with a condenser was added 7 (195.8 mg, 0.3 mmol), 8 (196.4 mg, 0.3 mmol), 6.0 mL of 2 M Na$_2$CO$_3$, 10 mL of toluene, 2 drops of Aliquat 336 under a gentle argon stream with vigorous stirring. The resulting mixture was evacuated and refilled with argon for three cycles to remove oxygen and then was added Pd(PPh$_3$)$_4$ (17 mg, 0.015 mmol, 5% equiv.) under argon stream. The mixture was heated under reflux over 7 days. After cooling to room temperature, the organic layer was separated and washed by water. Addition of 100 mL of methanol to organic solution offered the precipitate, which was collected by filtration and successively washed with water and methanol and dried under air. The crude polymer was then extracted subsequently with methanol, acetone, and chloroform in a Soxhlet extractor. The fraction from chloroform was concentrated under reduced pressure and precipitated into methanol to give the polymer PQDT as a blue solid (0.23 g, 86%). $^1$H NMR (400 MHz, CDCl$_3$): δ 7.79 (2H), 7.32 (2H), 3.08 (2H), 2.86 (2H), 2.32 (2H), 1.98 (4H), 1.20-1.80 (H), 0.95 (6H), 0.85 (6H).

PBDT yield: 0.23 g (88%). $^1$H NMR (400 MHz, CDCl$_3$) δ 7.46 (2H), 7.17 (2H), 2.98 (4H), 1.92 (4H), 1.80-1.22 (48H), 0.93 (6H), 0.85 (6H).

PNDT yield: 0.22 g (90%). $^1$H NMR (400 MHz, CDCl$_3$) δ 7.97 (2H), 7.85 (2H), 7.38 (2H), 2.85 (4H), 2.01 (4H), 1.9-1.2 (48H), 0.98-0.7 (12H).

REFERENCES FOR EXAMPLE 1:

(1) Ma, W. L. et al., *Adv. Funct. Mater.* 2005, 15, 1617-1622.
(2) Li, G. et al., *Nature Mater.* 2005, 4, 864-868.
(3) Thompson, B. C.; Fréchet, J. M. *J. Angew. Chem. Int. Ed.* 2008, 47, 58-77.
(4) Scharber, M. C. et al., *Adv. Mater.* 2006, 18, 789-794.
(5) Brabec, C. J. et al., *Adv. Funct. Mater.* 2002, 12, 709-712.
(6) Muhlbacher, D. et al., *Adv. Mater.* 2006, 18, 2884-2889.
(7) Peet, J. et al., *Nature Mater.* 2007, 6, 497-500.
(8) Zhang, F. L. et al., *Adv. Funct. Mater.* 2006, 16, 667-674.
(9) Andersson, L. M. et al., Appi. Phys. Lett. 2007, 91, 071108/1-071108/3.
(10) Slooff, L. H. et al., *Appl. Phys. Lett.* 2007, 90, 143506/1-143506/3.
(11) Wienk, M. M. et al., *Appi. Phys. Lett.* 2006, 88, 153511/1-153511/3.
(12) Yao, Y. et al., *Appi. Phys. Lett.* 2006, 89, 153507/1-153507/3.
(13) Ashraf, R. S. et al., *Macromol. Rapid Commun.* 2006, 27, 1454-1459.
(14) Blouin, N.; Michaud, A.; Leclerc, M. *Adv. Mater.* 2007, 19, 2295-2300.
(15) Blouin, N. et al., *J. Am. Chem. Soc.* 2008, 130, 732-742.
(16) Roncali, *J. Chem. Rev.* 1997, 97, 173-205.
(17) Tovar, J. D.; Rose, A.; Swager, T. M. *J. Am. Chem. Soc.* 2002, 124, 7762-7769.
(18) Tovar, J. D.; Swager, T. M. *Adv. Mater.* 2001, 13, 1775-1780.
(19) Polycyclic hydrocarbons I and II; Clar, E. Ed. Academic Press: London 1964.
(20) Watson, M. D.; Fechtenkotter, A.; Müllen, K. Chem. Rev. 2001, 101, 1267-1300.
(21) Shklyarevskiy, I. O. et al., *J. Am. Chem. Soc.* 2005, 127, 16233-16237.
(22) Miura, M.; Satoh, T.; Watanabe, H.; Ueda, M. WO/2007/105638, 2007.
(23) Watanabe, H. et al., *Chem. Lett.* 2007, 36, 1336-1337.
(24) Jayasuriya, N. et al., *J. Org. Chem.* 1989, 54, 4203-4205.
(25) Nicolas, Y. et al., *Org. Lett.* 2004, 6, 273-276.
(26) Pommerehne, J. et al., *Adv. Mater.* 1995, 7, 551-554.
(27) Zhan, X. W. et al., *Macromolecules* 2002, 35, 2529-2537.

(28) Arkhipov, V. I.; Bassler, H. *Phys. Status Solidi A* 2004, 201, 1152-1187.

(29) Melzer, C. et al., *Adv. Funct. Mater.* 2004, 14, 865-870.

(30) Mihailetchi, V. D. et al., *Adv. Funct. Mater.* 2005, 15, 795-801.

(31) Mihailetchi, V. D. et al., *J. Appl. Phys.* 2003, 94, 6849-6854.

(32) Coppo, P. et al., *J. Mater. Chem.* 2002, 12, 2597-2599.

(33) Wynberg, H.; Sinnige, H. J. M. *Rec. Trav. Chim.* 1969, 88, 1244-1245.

(34) Ohnishi, H.; Kozaki, M.; Okada, K. *Synth. Met.* 2003, 135, 85-86.

(35) Goodman, A. M.; Rose, A. *J. Appl. Phys.* 1971, 42, 2823-2830.

(36) Goh, C. et al., *Appl. Phys. Lett.* 2005, 86, 122110-122113.

(37) Popp, F. D. *J. Heterocyclic Chem.* 1974, 11, 79-82.

(38) Zhou, Q.; Carroll, P. J.; Swager, T. M. *J. Org. Chem.* 1994, 59, 1294-1301.

EXAMPLE 2

Synthesis of Compounds and Polymers

Synthesis of Compounds 8 and 10

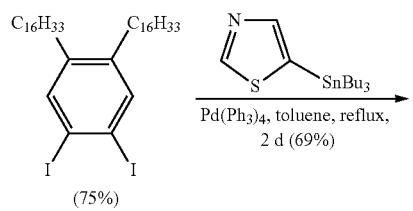

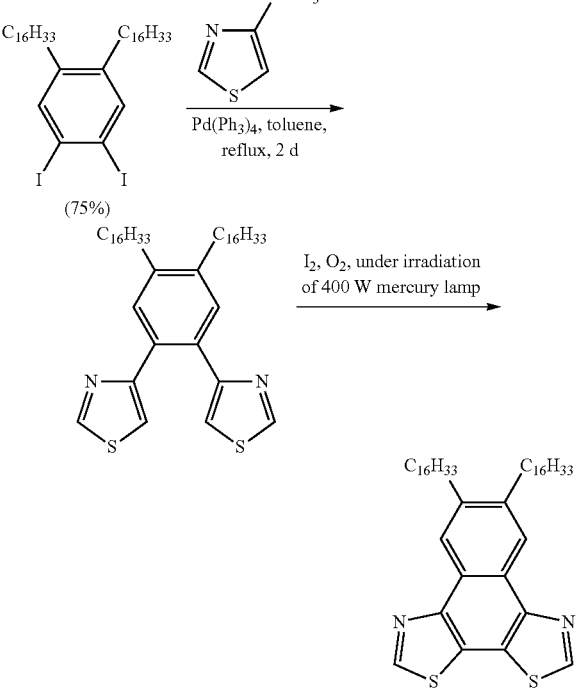

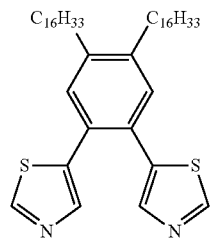

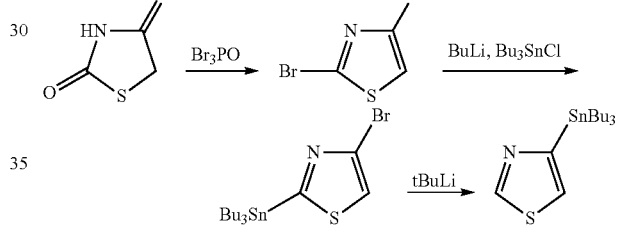

Synthesis of Compound 11 and Polymers

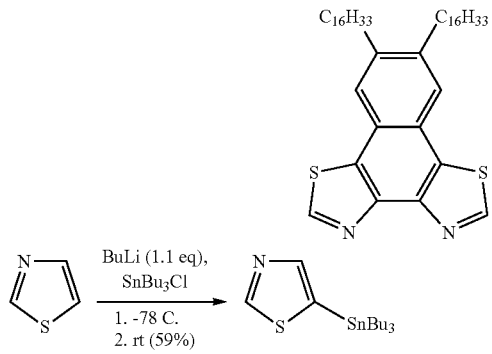

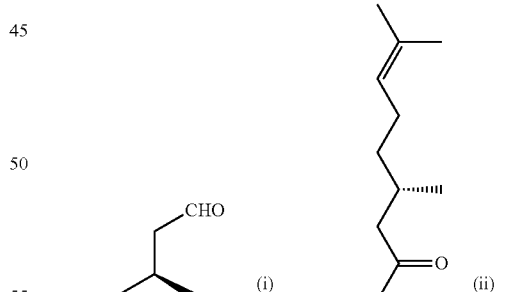

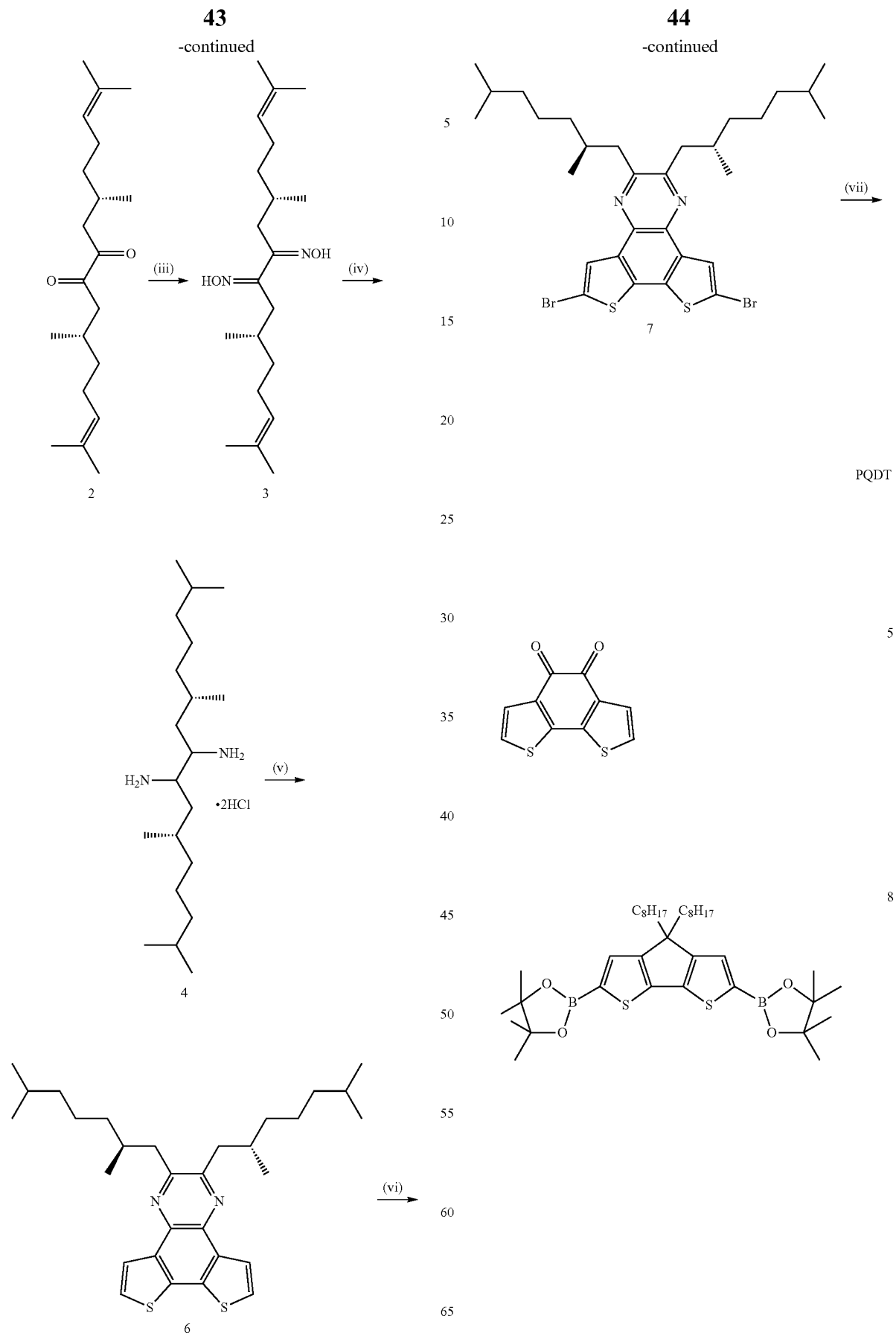

Synthesis of Compound 27 and Polymers
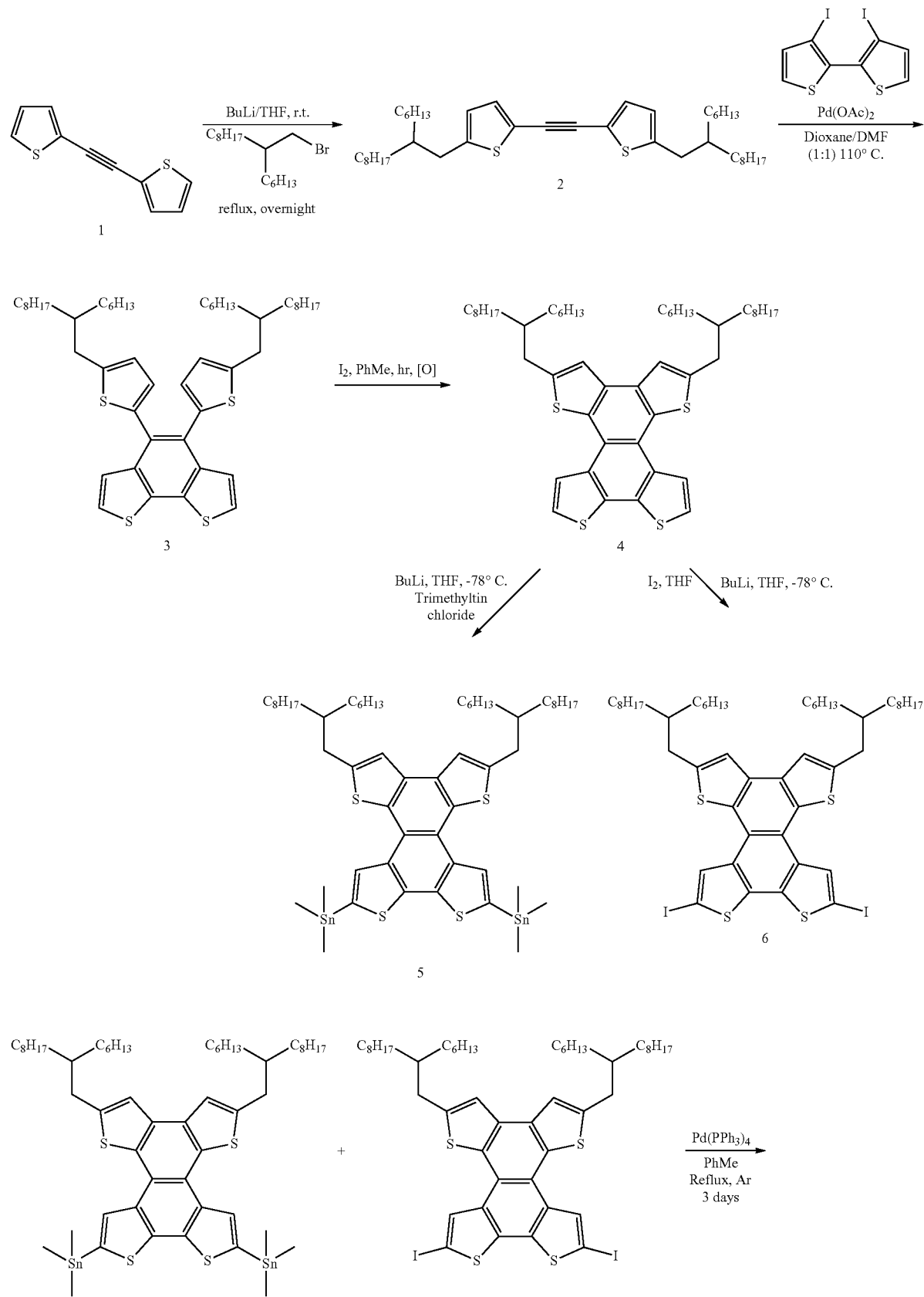

-continued
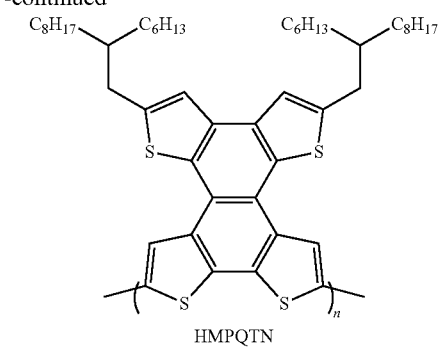
HMPQTN
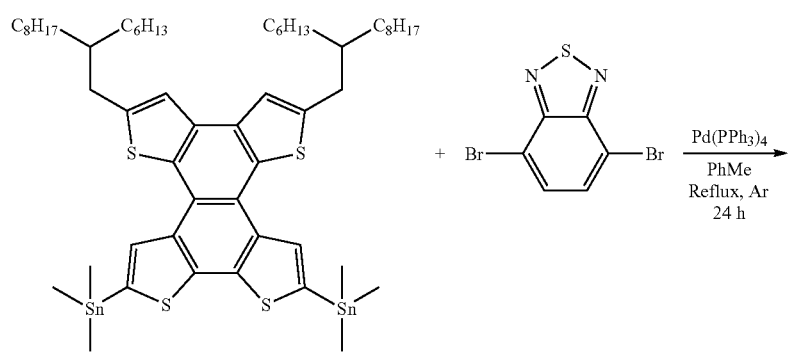
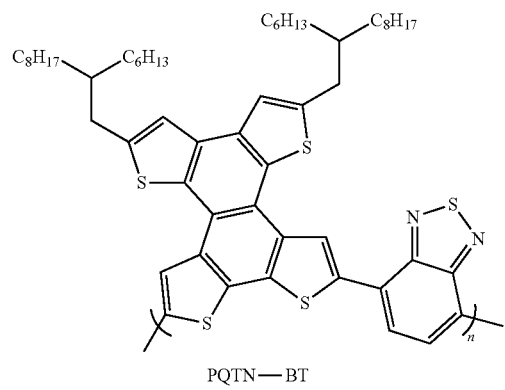
PQTN—BT

Synthesis of PDTBn-sol-DTBT

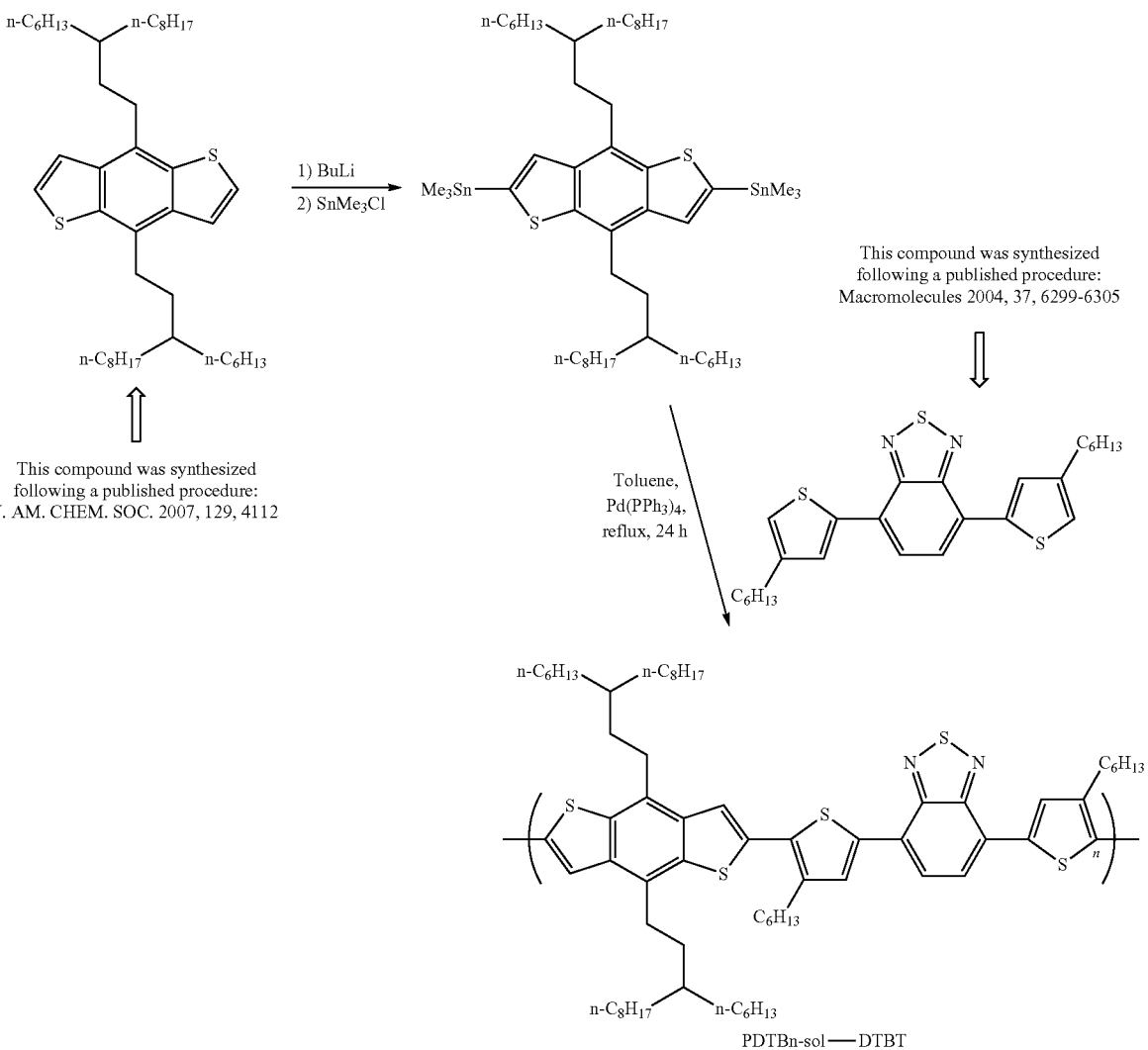

SYNTHESIS OF COMPOUND 11 AND POLYMERS

(6S,11S)-9-hydroxy-2,6,11,15-tetramethylhexadeca-2,14-dien-8-one (1).

To a 250 mL of two-necked round-bottom (RB) flask containing (−)citronellal (25.0 g, 163 mmol) in 50 mL of ethanol under argon was added the catalyst of 3-ethyl-5-(2-hydroxyethyl)-4-methylthiazolium bromide (4.1 g, 16.3 mmol) and triethylamine (17.0 mL, 120 mmol). The mixture was then heated to reflux over night. After removal of the solvent under reduced pressure, the resulted mixture was poured into 100 mL of water and extracted by ethyl ether (3×60 mL). The combined organic layer was dried over anhydrous $MgSO_4$ and concentrated under vacuum. The residue was purified by flash chromatography on silica gel (hexane:ethyl acetate=20: 1, v/v) to afford 18.5 g of product as a colorless oil (yield: 75%). $^1$H NMR (400 MHz, $CDCl_3$) δ 5.08 (m, 2H), 4.15 (m, 1H), 3.47 (dd, 1H, J=5.04 Hz), 2.40 (m, 1H), 2.2 (m, 1H), 1.9-2.1 (m, 6H), 1.60 (d, 12H), 1.1-1.3 (m, 4H), 0.8-1.0 (m, 6H). $^{13}$C NMR (400 MHz, $CDCl_3$) δ 212.63, 131.63, 131.30, 124.52, 124.40, 124.00, 75.59, 74.70, 45.16, 45.15, 41.15, 41.00, 37.95, 36.85, 36.83, 35.56, 29.36, 29.04, 28.92, 28.81, 25.65, 25.42, 25.39, 25.36, 25.22, 20.29, 19.82, 19.65, 18.46, 17.60.

(6S,11S)-2,6,11,15-tetramethylhexadeca-2,14-diene-8,9-dione (2).

To a solution of 1 (7.0 g, 22.7 mmol) in 100 mL of methylene chloride was added 7.5 g of PCC. The mixture was heated to reflux. After 16 hours, the mixture was cooled to room temperature and filtered. The solution was concentrated under reduced pressure. The crude compound was purified by flash chromatography on silica gel (hexane:ethyl acetate=20: 1, v/v) to afford the product as a colorless oil. Yield: 3.5 g (50%). $^1$H NMR (400 MHz, $CDCl_3$) δ 5.06 (m, 2H), 2.66-2.74 (dd, 2H, J=5.64, 16.71 Hz), 2.51-2.60 (dd, 2H, J=7.98, 16.73 Hz), 1.92-2.02 (m, 6H), 1.5-1.67 (s, 6H), 1.58 (s, 6H), 1.19-1.35 (m, 4H), 0.89 (d, 6H, J=6.66 Hz). $^{13}$C NMR (400 MHz, $CDCl_3$) δ 200.05, 131.60, 124.07, 52.96, 36.94, 28.49, 25.66, 25.36, 19.71, 17.60.

(6S,11S)-2,6,11,15-tetramethylhexadeca-2,14-diene-8,9-dione dioxime (3).

A 250 mL of two-necked RB flask containing a solution of 2 (6.12 g, 20.0 mmol) in ethanol (60 mL) and pyridine (8.0 mL) was purged with argon. Hydroxyammonium chloride (7.0 g, 100.0 mmol) was then added in one portion. The mixture was heated to reflux for 5 hours. After removal of the solvent under reduced pressure, 100 mL of water/ethanol (2:1, v/v) was added and ultrasonicated before filtration. The solid was then rinsed by 20 mL of cold hexane and dried under vacuum to afford a white pure solid. Yield: 5.5 g (95%). mp: 131-131.6° C. $^1$H NMR (400 MHz, CD$_3$OD) δ 4.93 (m, 2H), 3.16 (m, 2H), 2.32-2.47 (m, 4H), 1.72-1.90 (m, 6H), 1.51 (s, 6H), 1.44 (s, 6H), 1.17-1.20 (m, 2H), 1.01-1.05 (m, 2H), 0.72 (d, 6H, J=6.7 Hz). $^{13}$C NMR (400 MHz, CD$_3$OD) δ 157.95, 131.66, 126.05, 38.51, 32.19, 31.42, 26.68, 25.86, 20.16, 17.68.

(6S,11S)-2,6,11,15-tetramethylhexadecane-8,9-diamine dihydrogen chloride (4).

To a solution of 3 (1.9 g) in 50 mL of absolute ethanol at room temperature was added platinum oxide (0.4 g) and 2.0 mL of concentrated hydrogen chloride. The mixture was then purged with hydrogen and was kept stirring under hydrogen (with a hydrogen balloon) over 10 hours. After removing the solvent under reduced pressure, the residue was rinsed with cold hexane and directly used in the next step without further purification.

2,3-bis((S)-2,6-dimethylheptyl)dithieno[3,2-f:2',3'-h]quinoxaline (6).

To a 100 mL of two-necked RB flask equipped with a condenser was added the solution of 4 (1.20 g) in 50 mL of methanol, 5 (0.66 g, 3 mmol) and 2.0 mL of pyridine. The mixture was then heated to reflux with stirring over night. After removing the solvent under reduced pressure, the residue was re-dissolved in 30 mL of methylene chloride and washed by water and dried over anhydrous MgSO$_4$. The organic layer was then concentrated and the residue was purified by flash chromatography on silica gel (hexane:methylene chloride=4:1, v/v) to afford 0.91 g of pure product as a white solid (yield: 60%). mp: 57.5-58.7° C. $^1$H NMR (300 MHz, CDCl$_3$) δ 8.31 (d, 2H), J=5.28 Hz), 7.51 (d, 2H, J=5.22 Hz), 2.94-3.16 (dd, 2H, J=6.08 Hz, 14.2 Hz), 2.87-2.90 (dd, 2H, J=8.0 Hz, 14.2 Hz), 2.33 (m, 2H), 1.55 (m, 2H), 1.2-1.52 (m, 12H), 1.03 (d, 6H), J=6.58 Hz). 0.88 (d, 12H, J=7.45 Hz). $^{13}$C NMR (400 MHz, CDCl$_3$) δ 154.06, 136.04, 135.11, 133.95, 124.12, 42.13, 39.23, 37.36, 32.91, 27.98, 24.87, 22.71, 22.59, 19.82. MS: m/z=496.6 [M+2H]$^+$ (Calcd.: 494.3)

Synthesis of Alternating Copolymers Via Suzuki Coupling Polymerization

A representative procedure is as follows. To a flame dried 25 mL of two-necked RB flask equipped with a condenser was added 7 (195.8 mg, 0.3 mmol), 8 (196.4 mg, 0.3 mmol), 6.0 mL of 2 M Na$_2$CO$_3$, 10 mL of toluene, 2 drops of Aliquat 336 under a gentle argon stream with vigorous stirring. The resulting mixture was evacuated and refilled with argon for three cycles to remove oxygen and then was added Pd(PPh$_3$)$_4$ (17 mg, 0.015 mmol, 5% equiv.) under argon stream. The mixture was heated under reflux over 7 days. After cooling to room temperature, the organic layer was separated and washed by water. Addition of 100 mL of methanol to organic solution offered the precipitate, which was collected by filtration and successively washed with water and methanol and dried under air. The crude polymer was then extracted subsequently with methanol, acetone, and chloroform in a Soxhlet extractor. The fraction from chloroform was concentrated under reduced pressure and precipitated into methanol to give the polymer PQDT as a blue solid (0.23 g, 86%). $^1$H NMR (400 MHz, CDCl$_3$): δ 7.79 (2H), 7.32 (2H), 3.08 (2H), 2.86 (2H), 2.32 (2H), 1.98 (4H), 1.20-1.80 (H), 0.95 (6H), 0.85 (6H).

SYNTHESIS OF COMPOUND 27 AND POLYMERS

Synthesis of Compound 4(27).

In a 1000 mL of round bottom flask was added a solution of compound 3 (2.0 g, 2.5 mmol) and iodine (100 mg) in toluene (800 mL). The mixture was then put into the irradiation from a 400 W mercury lamp equipped with an efficient cooling system for 16 hours under magnetic stirring and air bubbling. The reaction mixture was then washed with a saturated aqueous solution of Na$_2$S$_2$O$_3$, dried over MgSO$_4$ and concentrated. After chromatography on silica gel (eluent: hexane), a colorless liquid was obtained (1.1 g, yield: 55%). $^1$H NMR (300 MHz, CDCl$_3$) δ 8.64 (d, 2H, J=5.51 Hz), 7.64 (d, 211, J=5.51 Hz), 7.52 (s, 2H), 3.01 (d, 4H, J=6.71 Hz), 1.88 (m, 2H), 1.40-1.20 (m, 48H), 0.88-0.83 (m, 12H). $^{13}$C NMR (400 MHz, CDCl$_3$) 145.01, 133.68, 132.92, 132.70, 132.62, 126.03, 123.46, 121.30, 120.24, 40.14, 35.25, 35.16, 33.46, 31.93, 31.60, 30.00, 29.68, 29.65, 29.35, 26.71, 26.88, 22.69, 14.14.

Synthesis of Compound 5

Compound 4 (0.8 g, 1.0 mmol) was dissolved in dry THF (30 mL) under argon at room temperature. 2.5M of n-BuLi in hexane (0.84 mL, 2.1 mmol) was added dropwise. After stirring at room temperature for 20 minutes, trimethyltin chloride (1 M in hexanes, 3 mL, 3 mmol) was injected in by a syringe. The reaction was then quenched by 20 mL of water ten minutes later. The mixture was extracted with ethyl ether. The organic layer was washed with water several times and dried over anhydrous magnesium sulfate. After removal of the solvent, the residue was dried under high vacuum to afford 0.8 g of pure product (yield 70%) as a pale yellow viscous liquid which was directly used in the next step without any purification.

$^1$H NMR (300 MHz, CDCl$_3$) δ 8.67 (s, 2H), 7.53 (s, 2H), 3.04 (d, 4H, J=6.61 Hz), 1.90 (m, 2H), 1.40-1.20 (m, 48H), 0.83-0.88 (m, 12H), 0.55 (s, 18H). $^{13}$C NMR (400 MHz, CDCl$_3$) 144. 67, 137.52, 137.42, 133.89, 133.61, 133.54, 132.69, 120.99, 120.26, 53.37, 39.94, 35.09, 33.43, 31.93, 30.02, 29.68, 29.36, 26.72, 26.68, 22.68, 14.08, 8.07.

Synthesis of Compound 6

Compound 4 (0.8 g, 1.0 mmol) was dissolved in dry THF (30 mL) under argon at room temperature. 2.5M of n-BuLi in hexane (0.84 mL, 2.1 mmol) was added dropwise. After stirring at room temperature for 20 minutes, 3 g of iodine (3 mmol) dissolved in 10 mL of anhydrous THF was transferred into the reaction mixture. The reaction was then quenched by 20 mL of water ten minutes later. 20 mL of 5% sodium hydroxide solution was added into the mixture and kept stirring for about 10 minutes. The mixture was then extracted with ethyl ether. The organic layer was washed with water several times and dried over anhydrous magnesium sulfate. After removal of the solvent, the residue was purified by flash chromatography on silica gel (hexane as eluent) to afford the 0.63 g of pure product (yield 60%) as a pale yellow liquid. $^1$H NMR (300 MHz, CDCl$_3$) δ 8.54 (s, 2H), 7.43 (s, 2H) 3.00 (d, 4H, J=6.69 Hz), 1.90 (m, 2H), 1.40-1.20 (m, 48H), 0.88-0.83 (m, 12H). $^{13}$C NMR (400 MHz, CDCl$_3$) 144.76, 135.20, 134.88, 133.44, 132.94, 131.45, 120.07, 119.02, 74.18, 40.18, 35.44, 33.50, 32.00, 31.96, 30.18, 29.84, 29.75, 29.41, 26.77, 26.71, 22.75, 22.71, 14.16, 14.16.

Synthesis of Homopolymer HMPQTN via Stilly Coupling Polymerization.

To a 25 mL of round bottom flask equipped with a condenser was added 3 (450.8 mg, 0.4 mmol), 4 (421.2 mg, 0.4 mmol) and 20 mL of anhydrous toluene. The mixture was then evacuated and refilled with argon over three cycles to remove oxygen and finally was added Pd(PPh$_3$)$_4$ (23 mg, 0.02 mmol, 5% equiv.) under argon stream. The mixture was heated under reflux over 2 days. After cooling to room temperature, the organic solution was added dropwise to 100 mL of methanol to obtain precipitate, which was collected by filtration and washed with methanol and dried. The crude polymer was then extracted subsequently with methanol, acetone, hexane, and chloroform in a Soxlet's extractor. The fraction from chloroform was concentrated under reduced pressure, and the residue was added dropwise to excess methanol to precipitate the polymer HMPQTN as a red solid (0.28 g, 44% yield).

Synthesis of D-A Copolymer PQTN-BT.

The polymerization was carried out in a scale of 0.5 mmol for each monomer using the same procedure as the preparation of HMPQTN. Subsequent Soxlet extraction with methanol, acetone, hexane, and chloroform finally afforded 0.28 g of the polymer from chloroform fraction with the yield of 60%.

EXAMPLE 3

Development of Low Band Gap Polymers with Deep LUMO Levels for Highly Efficient Polymer Solar Cells As a potential low cost alternative to mainstream silicon solar cells, polymer solar cells have attracted a significant amount of attention in the research community.[1] The prevailing concept is to construct an organic p-n junction, usually by a heterogeneous blend of a conjugated polymer (p-type) with a fullerene derivative (n-type). The phase separation in this bulk heterojunction (BHJ) leads to exciton separation and charges transport through different domains.[1c]

Fullerene derivatives (such as PC$_{61}$BM) have been extensively used as the n-type semiconductor in BHJ solar cells due to their superior electron accepting and transporting behavior. However, these fullerene derivatives are usually poor light absorbers, thereby leaving the task of light absorbing to the conjugated polymers. Moreover, fullerene derivatives usually have fixed energy levels (e.g., a LUMO of 4.2 eV), which largely dictate the appropriate energy levels of the conjugated polymers in order to construct the required type II heterojunction alignment (i.e., polymer and fullerene with staggered band energies)[2] for effective exciton splitting. These stringent requirements set the proposed "ideal" conjugated polymer with an estimated low HOMO energy level of −5.4 eV and a small band gap of 1.5 eV.[3] Therefore, a significant amount of efforts has been devoted to the engineering band gap and energy level of conjugated polymers; as a result, a few highly efficient polymers have been reported with the record high efficiency surpassing 7%.[4]

In order to concurrently lower the HOMO energy level and the band gap as required by the ideal polymer, we recently proposed the "weak donor-strong acceptor" strategy to construct alternating copolymers, in order to approach ideal polymers.[3c] A few such materials, by incorporating weak donor moieties based on fused benzodithiophene, and a strong acceptor based on benzothiadiazole (BT), have successfully demonstrated with noticeably high efficiency in typical BHJ devices.[5] In these conjugated polymers, close to ideal HOMO energy levels were achieved (e.g., −5.46 eV), which led to the observed open circuit voltage ($V_{oc}$) as high as 0.85 V.[5b] However, the band gaps of these materials were still relatively larger than the proposed 15 eV of ideal polymers, which explains why mediocre short circuit currents ($J_{sc}$) were obtained. Logically, in order to further improve the efficiency, a smaller band gap is needed to achieve a higher short circuit current ($J_{sc}$) while the low HOMO energy level should still be maintained.

Our previous study indicated that the LUMO of donor-acceptor copolymers largely resides on the acceptor moiety.[6] Therefore, we envisioned that installing a "stronger" acceptor to lower the LUMO energy level in conjunction with these proven weak donors would lead to a smaller band gap and maintain the low HOMO energy level in these newly designed materials.

If we replaced the benzene in the BT unit with pyridine, the new acceptor, thiadiazolo[3,4-c]pyridine (PyT), would be one such stronger acceptor. Similar strategy has been demonstrated by Leclerc et al.;[7] the copolymer (PCDTPT) indeed showed a much lower LUMO level compared with that of PCDTBT. However, a much lower efficiency of 0.7% was obtained for the newly synthesized PCDTPT, than the 3.6% of the original PCDTBT, presumably due to the low molecular weight and low solubility of PCDTPT. To solve these issues, we employed the strategy of a "soluble" acceptor,[5a, 6a] by flanking the PyT moiety with two alkylated thienyl units, which converted the PyT into the new soluble stronger acceptor, DTPyT. As demonstrated in our previous study,[6a] anchoring alkyl chains to the 4 position of the thienyl units of DTPyT would only introduce minimum steric hindrance, while significantly improving the molecular weight and solubility of resulting polymers.

Scheme 4. Molecular structure of
PNDT—DTPyT, PQDT—DTPyT and PBnDT—DTPyT.

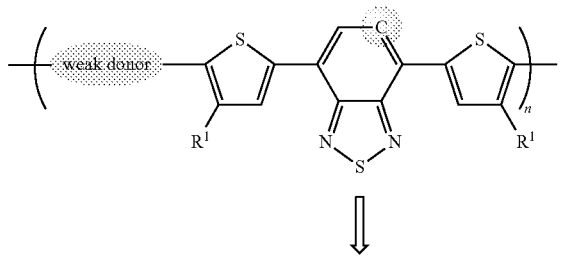

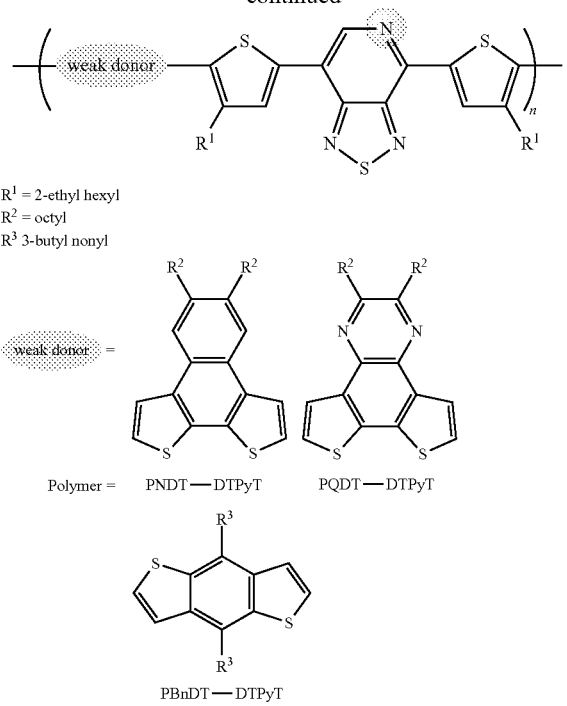

$R^1$ = 2-ethyl hexyl
$R^2$ = octyl
$R^3$ 3-butyl nonyl

Polymer = PNDT—DTPyT   PQDT—DTPyT

PBnDT—DTPyT

Herein we report the synthesis of a series of "weak donor-strong acceptor" polymers PNDT-DTPyT, PQDT-DTPyT and PBnDT-DTPyT by copolymerizing various donor moieties, NDT (naphtho[2,1-b:3,4-b']dithiophene), QDT (dithieno[3,2-f:2',3'-h]quinoxaline), BnDT (benzo[1,2-b:4,5-b']dithiophene) with the newly conceived soluble DTPyT acceptor moiety (Scheme 4). Our preliminary investigation on the photovoltaic properties of these polymers in typical BHJ devices using $PC_{61}BM$ as the electron acceptor showed highly respectable power conversion efficiency (PCE) over 5.5% for PQDT-DTPyT, and over 6% for PBnDT-DTPyT and PNDT-DTPyT.

The synthesis of the alkylated DTPyT is modified from the reported procedure[7] (experimental details given below). The other co-monomers—alkylated NDT, QDT and BnDT—were prepared by us previously.[5a, 8] Three polymers, PNDT-DTPyT, PQDT-DTPyT and PBnDT-DTPyT were synthesized via the microwave-assisted Stille polycondensation[1e] between alkylated dibrominated DTPyT and corresponding distannane monomers. To ensure a good solubility in the processing solvents, alkyl chains were properly anchored on both the DTPyT monomer and the other three co-monomers, with only negligible steric hindrance introduced.[6a]

We noticed an interesting color change from red to blue shortly after adding catalyst to the solution of NDT distannane monomer and alkylated dibromoDTPyT monomer at room temperature, indicating the occurrence of Stille reaction at room temperature for this specific pair (NDT and DTPyT). Crude polymers were purified by the Soxhlet extraction with methanol, ethyl acetate, hexane and chloroform. The chloroform fraction was concentrated and re-precipitated in methanol to afford the purified polymers. Gel permeating chromatography (GPC) studies of these three polymers were conducted in trichlorobenzene at high temperature (135° C.). All three polymers showed much higher molecular weight than that PCDTPT,[7] especially in the case of PBnDT-DTPyT (Table 3), underscoring the usefulness of introducing the "soluble" acceptor.

TABLE 3

Polymerization results and energy levels of PNDT-DTPyT, PQDT-DTPyT and PBnDT-DTPyT.

| Polymers | Yield | Mw [kg/mol][a] | PDI | HOMO [eV][b] | LUMO [eV][b] |
|---|---|---|---|---|---|
| PNDT-DTPyT | 92% | 17.1 | 2.14 | 5.36 | 3.42 |
| PQDT-DTPyT | 88% | 21.7 | 2.27 | 5.50 | 3.44 |
| PBnDT-DTPyT | 53% | 104.4 | 3.64 | 5.47 | 3.44 |

[a]Determined by GPC in TCB at 135° C. using polystyrene standards.
[b]HOMO and LUMO levels were calculated from the onsets of oxidation peaks and reduction peaks, respectively.

Figure 7:
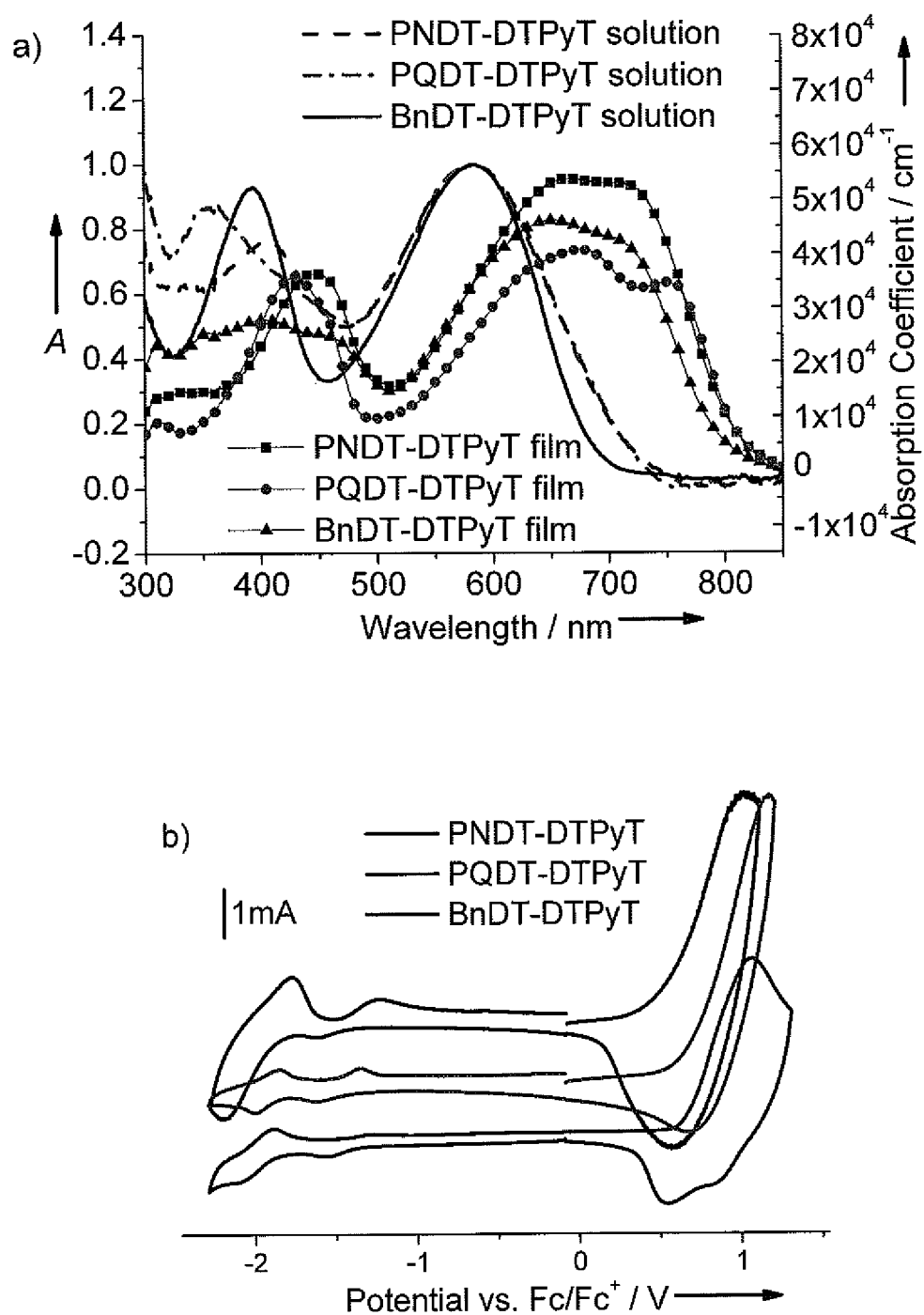
FIG. 7. (a) The UV-vis absorption spectra of PNDT-DTPyT, PQDT-DTPyT and PBnDT-DTPyT in chlorobenzene solution at 100° C. and in solid films. (b) Electrochemical cyclic voltammetry curves of PNDT-DTPyT, PQDT-DTPyT and PBnDT-DTPyT.

The UV-vis absorption spectra of the three polymers in chlorobenzene solution at elevated temperature (100° C.) and in the solid state are shown in FIG. 7a. The solution absorption spectra of the three polymers at high temperature are almost identical, containing two absorption maxima as typically observed for donor-acceptor low band gap materials. However, these polymers tend to aggregate. For example, a large bathochromic shift (ca. 25-90 nm) was noticed even in the solution at room temperature (Supporting Information). Because BHJ photovoltaic (PV) cells are solid state devices, the absorption of these polymers as thin films is more probative. The absorption spectra in the solid state are quite different for these three polymers, indicating different polymer chain organization and interaction in thin films.[1e] For example, the absorption of PBnDT-DTPyT has the largest redshift when transitioning from solution to the film, presumably due to the symmetric molecular structure of the BnDT unit which helps molecular stacking in the solid state. A larger redshift of the absorption spectrum of PNDT-DTPyT than that of PQDT-DTPyT was observed, suggesting PNDT-DTPyT adopts a more planar polymer chain conformation and more effective chain-chain stacking in the solid state. The estimated optical band gaps of PNDT-DTPyT, PQDT-DTPyT and PBnDT-DTPyT are 1.53 eV, 1.56 eV and 1.51 eV respectively, noticeably reduced (ca. 0.09-0.19 eV) compared with the band gaps of their DTBT counterparts.[5]

The electrochemical behavior of all three polymers was measured by the cyclic voltammetry (CV) (FIG. 7b). The recorded cyclic voltammogram was used to estimate the corresponding HOMO and LUMO energy levels of each polymer (Table 3). The LUMO levels of all three polymers, calculated from the onset of the reduction potential, are almost identical within the experimental error, indicative of the identical acceptor unit (DTPyT). This agrees well with the previous discovery that LUMO of donor-acceptor polymer is primarily located in the acceptor unit.[3c, 6a, 7] Therefore, the change of the electron-donor moiety has only negligible effect on the LUMO levels of the resulting polymers. In addition, replacing the DTBT with the stronger acceptor of DTPyT in these three polymer lowered the LUMO energy levels of these polymers by ~0.2 eV compared with the corresponding values of their DTBT analog.[5] The lowered LUMO energy level explains the observed band gap reduction in these polymers. It is also worth noting that all three weak donors—NDT, QDT and BnDT—were able to maintain low HOMO energy levels around the ideal HOMO energy level of −5.4 eV.

Figure 8:
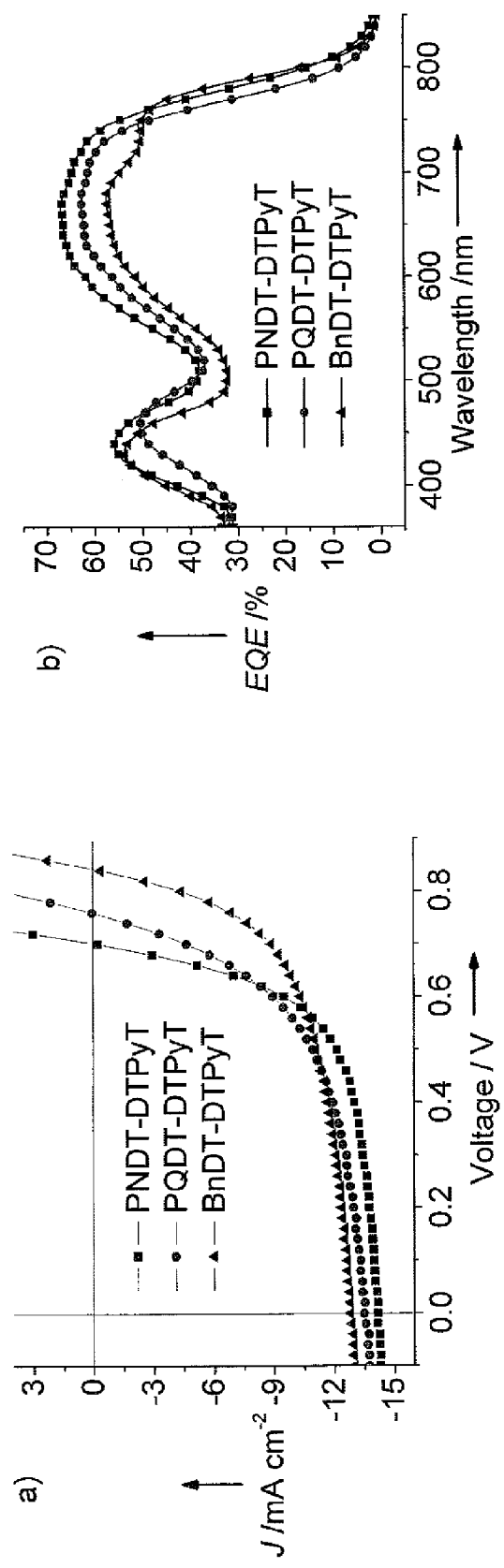
FIG. 8. (a) Current density-voltage (J-V) curves of polymer/PCBM based solar cell devices under AM 1.5G illumination (100 mW cm$^{-2}$). (b) External quantum efficiency (EQE) curves of polymer/PCBM based solar cell devices.
Figure 9:
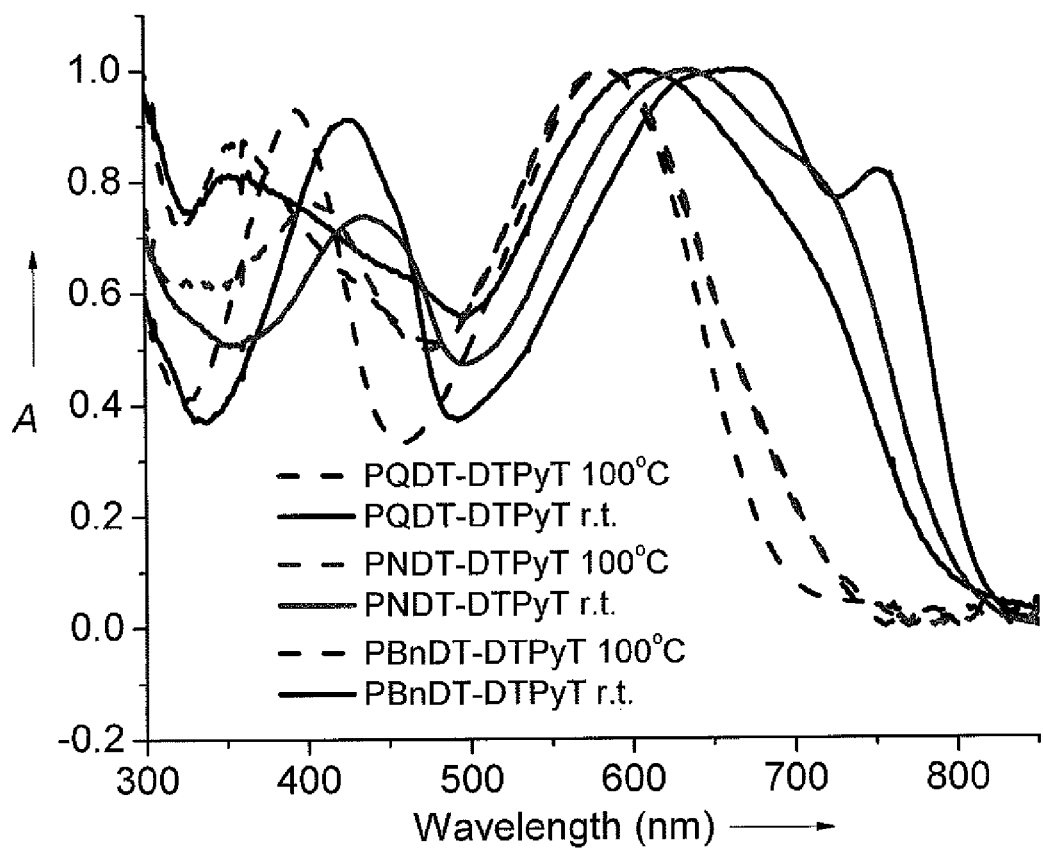
FIG. 9. UV-vis Absorption spectra of PNDT-DTPyT, PQDT-DTPyT and PBnDT-DTPyT in chlorobenzene (CB) solution at room temperature and 100° C.

BHJ PV devices were fabricated with a typical configuration of ITO/PEDOT:PSS(40 nm)/polymer:$PC_{61}BM$/Ca(40 nm)/Al(70 nm). All PV devices were tested under simulated AM1.5G illumination (100 mW/cm$^2$). Typical current density-voltage (J-V) characteristics are shown in FIG. 8a and summarized in Table 4. All devices showed promising efficiency over 5.5% with one of these three polymers as the donor material and $PC_{61}BM$ as the electron acceptor in our initial trials. The highest current of 14.2 $mA/cm^2$ was obtained for PNDT-DTPyT based devices, which is among the highest $J_{sc}$ obtained for BHJ device consisting of a donor polymer and $PC_{61}BM$ as the acceptor.[9] The high $J_{sc}$ along with a $V_{oc}$ of 0.71V and a high fill factor (FF) of 0.61, yields an impressive PCE of 6.20% for PNDT-DTPyT:$PC_{61}BM$ based BHJ solar cells. When PQDT-DTPyT or PBnDT-DTPyT with deeper HOMO levels is used in BHJ solar cells, we observe higher $V_{oc}$ than that of PNDT-DTPyT based devices. Though PQDT-DTPyT based devices generate smaller $J_{sc}$ than that of PNDT-DTPyT devices, presumably due to the slightly larger band gap of PQDT-DTPyT, a PCE of 5.57% is still achieved because the increased $V_{oc}$ partially compensates the decreased $J_{sc}$.

Because these two polymers (PQDT-DTPyT and PNDT-DTPyT) only differ by two atoms in the respective repeating units, the increased $V_{oc}$ is a direct result from the deeper HOMO level introduced by the QDT unit. Interestingly, the $J_{sc}$ of PBnDT-DTPyT based device is smaller than those of the other two polymers based devices, despite that the PBnDT-DTPyT polymer has the smallest band gap. Though not wishing to be bound by theory, two possible reasons are proposed to explain this observation. First, PBnDT-DTPyT has the longest solubilizing chains among all three studies polymers. Therefore, the effective chromophore density in the solid state is the lowest in the case of PBnDT-DTPyT, as corroborated by its relatively low absorption coefficient. Second, such long alkyl chains could increase the inter-conjugated backbone distance and lower the hole mobility.[10] However, a noticeably high $V_{oc}$ of 0.85 V was obtained, which helps reach a respectable PCE of 6.32% in PBnDT-DTPyT based BHJ devices.

To further confirm the accuracy of the measurements, the external quantum efficiency (EQE) curves of the devices based on these three polymers were acquired and shown in FIG. 3b. All devices showed very high incident photo-conversion efficiency, with maxima around 670 nm. The calculated $J_{sc}$ values by integrating the EQE data with an AM1.5G reference spectrum match the experimental values within 5% error. Further increase on the $J_{sc}$ is still possible when $PC_{71}BM$ is employed to replace $PC_{61}BM$, since $PC_{71}BM$[1a, 11] has significant absorption in the visible region than $PC_{61}BM$.

TABLE 4

Photovoltaic properties of PNDT-DTPyT, PQDT-DTPyT and PBnDT-DTPyT based BHJ solar cells processed with polymer/$PC_{61}BM$ 1:1 (w/w) blend in DCB.

| Polymers | Thickness [nm] | $J_{sc}$ [mA/$cm^2$] | $V_{oc}$ [V] | FF [%] | $PCE_{max}$ ($PCE_{average}$) [%] |
|---|---|---|---|---|---|
| PNDT-DTPyT | 85 | 14.16 | 0.71 | 61.7 | 6.20 (6.07) |
| PQDT-DTPyT | 90 | 13.49 | 0.75 | 55.1 | 5.57 (5.32) |
| PBnDT-DTPyT | 90 | 12.78 | 0.85 | 58.2 | 6.32 (6.11) |

In summary, a soluble strong acceptor, DTPyT, which is stronger than the commonly used DTBT, has been synthesized and incorporated into our "weak donor-strong acceptor" copolymer. Three new polymers (PNDT-DTPyT, PQDT-DTPyT and PBnDT-DTPyT) showed noticeably reduced LUMO levels, slightly reduced HOMO levels, thus smaller band gap than their DTBT counterparts. The smaller band gap significantly improves the observed $J_{sc}$ of the related BHJ devices, while the low HOMO energy level maintains the high $V_{oc}$. Therefore, all three polymers achieved high efficiency numbers in the BHJ devices, demonstrating the great utility of DTPyT acceptor moiety in designing high performance solar cell materials.

Experimental Section

Reagents and Instrumentation

All reagents and chemicals were purchased from commercial sources (Aldrich, Acros, Matrix Scientific) and used without further purification unless stated otherwise. Reagent grade solvents were dried when necessary and purified by distillation. Microwave assisted polymerizations were conducted in a CEM Discover Benchmate microwave reactor. Gel permeation chromatography (GPC) measurements were performed on a Polymer Laboratories PL-GPC 220 instrument (at the University of Chicago) using 1,2,4-trichlorobenzene as the eluent (stabilized with 125 ppm BHJ) at 135° C. The obtained molecular weight is relative to the polystyrene standard. $^1H$ and $^{13}C$ nuclear magnetic resonance (NMR) measurements were recorded either with a Bruker Avance 300 MHz AMX or Bruker 400 MHz DRX spectrometer. UV-visible absorption spectra were obtained by a Shimadzu UV-2401PC spectrophotometer. The thicknesses of films were recorded by a profilometer (Alpha-Step 200, Tencor Instruments). Cyclic voltammetry measurements were carried out using a Bioanalytical Systems (BAS) Epsilon potentiostat equipped with a glass carbon working electrode, a Ag/$AgNO_3$ (0.01M in anhydrous acetonitrile) reference electrode, and a Pt wire counter electrode. The measurements were done in anhydrous acetonitrile with tetrabutyl ammonium hexafluorophosphate (0.1 M) as the supporting electrolyte under an argon atmosphere at a scan rate of 100 mV/s. The potential of Ag/$AgNO_3$ reference electrode was internally calibrated by using the ferrocene/ferrocenium redox couple (Fc/$Fc^+$), which has a known reduction potential of 4.8 eV.

Polymer Solar Cell Fabrication and Testing

Glass substrates coated with patterned indium-doped tin oxide (ITO) were purchased from Thin Film Devices, Inc. The 150 nm sputtered ITO pattern had a resistivity of 15Ω/□. Prior to use, the substrates were ultrasonicated for 20 minutes in acetone followed by deionized water and then 2-propanol. The substrates were dried under a stream of nitrogen and subjected to the treatment of UV-Ozone over 30 minutes. A filtered dispersion of PEDOT:PSS in water (Baytron PH500) was then spun cast onto clean ITO substrates and then baked at 140° C. for 15 minutes. A blend of polymer and PCBM was dissolved in chlorinated solvent with heating at 110° C. for 8 hours. All the solutions were then spun cast onto PEDOT:PSS layer and dried at room temperature in the glovebox under nitrogen atmosphere for 12 hours. Then a 40 nm film of calcium and a 70 nm aluminum film were thermal deposited at a pressure of $1\times10^{-6}$ mbar. here are 8 devices per substrate, with an active area of 0.12 $cm^2$ per device. Device characterization was carried out under AM 1.5G irradiation with the intensity of 100 mW/cm² (Oriel 91160, 300 W) calibrated by a NREL certified standard silicon cell. Current density versus potential (J-V) curves were recorded with a Keithley 2400 digital source meter. EQE were detected under monochromatic illumination (Oriel Cornerstone 260¼ m monochromator equipped with Oriel 70613NS QTH lamp) and the calibration of the incident light was performed with a monocrystalline silicon diode. All fabrication steps after adding the PEDOT:PSS layer onto ITO substrate, and characterizations were performed in gloveboxes under nitrogen atmosphere.

Detailed Synthesis

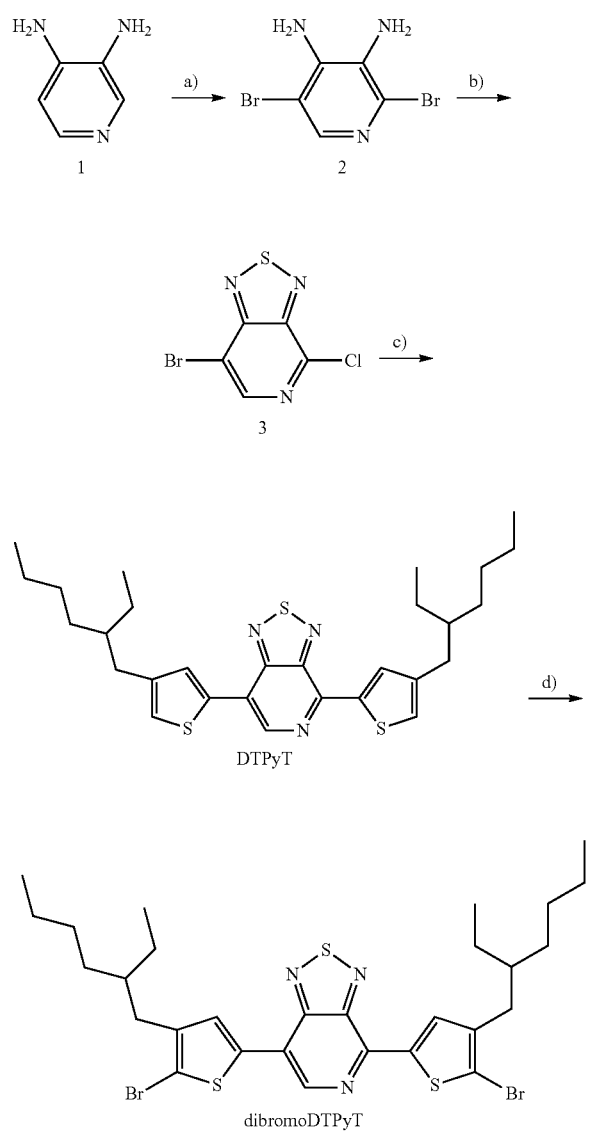

a). HBr, Br₂, reflux 40% b). SOCl₂ reflux 55% c). (4-(2-ethylhexyl)thiophen-2-yl)trimethylstannane, PdCl₂(PPh₃)₂, DMF, THF, reflux, 74% d). NBS, THF, rt, 80%.

The 7-bromo-4-chloro[1,2,5]thiadiazoleo[3,4-c]pyridine (3) (Blouin et al., *J. Am. Chem. Soc.* 2008, 130, 732) and (4-(2-ethylhexyl)thiophen-2-yl) trimethylstannane (Zhou et al., *Macromolecules* 2010, 43, 811) have been reported in the literature. Other compounds have been synthesized following procedures described below.

Synthesis of DTPyT

In a 250 mL flame-dried 2-neck round-bottom flask with a condenser, (4-(2-ethylhexyl)thiophen-2-yl)trimethylstannane (2.04 g, 4.2 mmol, 2.2 eq), 7-bromo-4-chloro[1,2,5] thiadiazoleo[3,4-c]pyridine (0.475 g, 1.90 mmol, 1 eq) and argon-saturated DMF 10 mL and THF 10 mL were added. The mixture was then purged with argon for 15 min. Then, bis(triphenylphosphine)palladium(II) dichloride (Pd(PPh₃)₂Cl₂) was added and the reaction mixture was heated to reflux overnight. The reaction mixture was then cooled to room temperature and the solvent was evaporated. The crude red product was re-dissolved in THF and filtered through a short silica gel. The solvent was evaporated and the product was recrystallized from ethanol. Yield: 0.74 g (74%) ¹H NMR (400 MHz, CDCl₃): δ 8.81 (s, 1H), 8.50 (s, 1H), 7.93 (s, 1H), 7.18 (s, 1H), 7.05 (s, 1H), 2.64 (m, 4H), 1.67 (m, 2H), 1.21-1.42 (m, 16H), 0.95 (m, 12H).

Synthesis of dibromoDTPyT.

DTPyT (0.24 g, 0.456 mmol) and N-bromosuccinimide (NBS) (178 mg, 0.1 mmol) were added into THF under stirring. The reaction mixture was stirred at a room temperature for 6 h, then the reaction mixture washed with washed with brine and dried over anhydrous sodium sulfate. The solvent was removed at a reduced pressure to give the product as a red solid. Needle-like crystal was obtained by recrystallizing from ethanol. Yield: 249 mg (80%). ¹H NMR (400 MHz, CDCl₃): δ 8.65 (s, 1H), 8.29 (s, 1H), 7.72 (s, 1H), 2.58 (m, 4H), 1.71 (m, 2H), 1.20-1.40 (m, 16H), 0.91 (m, 12H). ¹³C NMR (400 MHz, CDCl₃): δ 154.59, 145.49, 143.41, 142.49, 140.16, 140.82, 135.76, 133.06, 129.06, 119.85, 117.08, 112.55, 40.00, 34.07, 32.55, 28.81, 25.79, 23.05, 14.08, 10.86.

General Procedures for Microwave-Assisted Polymerization.

To a 10 mL Microwave pressurized vial equipped with a stirring bar, NDT (104 mg, 0.132 mmol), dibromoDTPyT (90 mg, 0.132 mmol), Pd₂(dba)₃ (6 mg) and P(o-tol)₃, (16.5 mg) were added. Then the tube was sealed and evacuated and refilled with argon for three cycles, followed by the addition of o-xylene (0.6 mL) and DMF (0.1 mL) into the tube in a glovebox. Reaction tube was put into microwave reactor and heated to 150° C. under 300 watt microwave for 20 min. After cooling to room temperature, the organic solution was added dropwise to 200 mL of methanol to obtain precipitate, which was collected by filtration and washed with methanol and dried. The crude polymer was then extracted subsequently with methanol, acetone, hexane and CHCl₃ in a Soxhlet's extractor. The fraction from chloroform was concentrated under reduced pressure and precipitated into methanol to give the polymer PNDT-4DTBT (120 mg, 92%) as a dark green solid.

PNDT-DTPyT.

¹H NMR (400 MHz, CDCl₂CDCl₂): δ 8.98-7.53 (br, 7H), 3.21-2.40 (br, 8H), 2.12-1.22 (br, 42H), 1.22-0.75 (br, 18H).

PQDT-DTPyT.

$^1$H NMR (400 MHz, CDCl$_2$CDCl$_2$): δ 8.95-7.65 (br, 5H), 3.31-2.42 (br, 8H), 2.22-1.83 (br, 6H), 1.83-1.23 (br, 36H), 1.23-0.81 (br, 18H).

PBnDT-DTPyT.

$^1$H NMR (400 MHz, CDCl$_2$CDCl$_2$): δ 8.95 (s, 1H), 8.64 (s, 1H), 8.09 (s, 1H), 7.76 (s, 1H), 7.70 (s, 1H), 3.28 (br, 4H), 3.07 (br, 4H), 1.96 (br, 6H), 1.70-1.27 (br, 50H), 1.08-0.85 (br, 24H).

TABLE 5

Optical data of PNDT-DTPyT, PQDT-DTPyT and BnDT-DTPyT.

| | UV-Vis Absorption | | | | | | | | |
|---|---|---|---|---|---|---|---|---|---|
| | CB solution at 100° C. | | | CB solution at room temp. | | | Film | | |
| Polymer | $\lambda_{max}$ [nm] | $\lambda_{onset}$ [nm] | $E_g^a$ [eV] | $\lambda_{max}$ [nm] | $\lambda_{onset}$ [nm] | $E_g^a$ [eV] | $\lambda_{max}$ [nm] | $\lambda_{onset}$ [nm] | $E_g^a$ [eV] |
| PNDT-DTPyT | 583 | 727 | 1.71 | 635 | 800 | 1.55 | 667, 712 | 812 | 1.53 |
| PQDT-DTPyT | 583 | 717 | 1.73 | 607 | 790 | 1.57 | 654 | 797 | 1.56 |
| PBnDT-DTPyT | 583 | 682 | 1.82 | 670 | 810 | 1.53 | 676 | 819 | 1.51 |

$^a$Calculated from the intersection of the tangent on the low energetic edge of the absorption spectrua with the baseline.

TABLE 6

Mobility of polymers under SCLC condition.

| | Polymer Only | | Polymer:PCBM (1:1) | |
|---|---|---|---|---|
| | Thickness (nm) | Mobility (cm2/V · s) | Thickness (nm) | Mobility (cm2/V · s) |
| PNDT-DTPyT | 50 | $1.94 \times 10^{-6}$ | 70 | $4.97 \times 10^{-6}$ |
| PQDT-DTPyT | 60 | $1.58 \times 10^{-6}$ | 90 | $1.79 \times 10^{-5}$ |
| PBnDT-DTPyT | 60 | $2.76 \times 10^{-6}$ | 75 | $5.91 \times 10^{-6}$ |

REFERENCES FOR EXAMPLE 3

[1] a) J. C. Bijleveld, A et al., *J. Am. Chem. Soc.* 2009, 131, 16616; b) N. S. Lewis, Science 2007, 315, 798; c) G. Yu et al., *Science* 1995, 270, 1789; d) S. H. Park et al., *Nat. Photonics* 2009, 3, 297; e) R. C. Coffin, et al., *Nat. Chem.* 2009, 1, 657; f) L. Hua et al., *Angew. Chem.*, Int. Ed. 2010, 49, 1500; g) S. Xiao et al., *ACS Symp. Ser.* 2010, 1034, 71.

[2] A. Moulton, J.-M. Nunzi, Polym. Int. 2006, 55, 583.

[3] a) B. C. Thompson, J. M. J. Frechet, Angew. Chem., Int. Ed. 2008, 47, 58; b) M. C. Scharber et al., Adv. Mater. 2006, 18, 789; c) H. Zhou et al., *ACS Appl. Mater. Interfaces* 2010, 2, 1377.

[4] a) H.-Y. Chen et al., *Nat. Photonics* 2009, 3, 649; b) Y. Liang et al., *Adv. Mater.* 2010, DOI: 10.1002/adma.200903528.

[5] a) S. C. Price, A. C. Stuart, W. You, *Macromolecules* 2010, 43, 4609; b) H. X. Zhou et al., L. Q. Yang, W. You, *Macromolecules* 2010, Submitted.

[6] a) H. X. Zhou et al., *Macromolecules* 2010, 43, 811; b) S. Xiao et al., *ACS Appl. Mater. Interfaces* 2009, 1, 1613; c) S. Xiao et al., *Adv. Funct. Mater.* 2010, 20, 635.

[7] N. Blouin et al., *J. Am. Chem. Soc.* 2008, 130, 732.

[8] a) S. Q. Xiao, H. X. Zhou, W. You, *Macromolecules* 2008, 41, 5688; b) J. H. Hou et al., *Macromolecules* 2008, 41, 6012.

[9] a) Y. Liang et al., *J. Am. Chem. Soc.* 2009, 131, 56; b) Y. Y. Liang et al., *J. Am. Chem. Soc.* 2009, 131, 7792.

[10] Y. Kim et al., *Nat. Mater.* 2006, 5, 197.

[11] a) Q. Zheng et al., *J. Am. Chem. Soc.* 2010, 132, 5394; b) F. Huang et al., *J. Am. Chem. Soc.* 2009, 131, 13886.

EXAMPLE 4

Polymers Containing Fluorine Atoms for High Performance Solar Cells

With intense research on cheap sustainable energy, the past several years have seen great performance advances of bulk heterojunction (BHJ) polymer solar cells.[1] Major improvements were originated from the application of novel semiconducting polymers as electron donor, while maintaining fullerene derivatives as electron acceptor. In a typical BHJ devices with 6,6-phenyl-C61-butyric acid methyl ester (PC$_{61}$BM) as the electron acceptor, an ideal polymer as the major light absorber should have a low band gap around 1.4 eV with broad absorption and high absorption coefficient to allow maximum sun light harvest to generate a high short circuit current (J$_{sc}$); and as an electron donor material, a LUMO level around −3.9 eV and a deep HOMO level around −5.5 eV are essential to guarantee efficient exciton separation and a high open circuit voltage (V$_{oc}$). Maximum power conversion efficiency (PCE) over 10% is predicted for such single layered BHJ devices.[2]

To construct such ideal donor polymers, a "weak donor-strong acceptor" strategy has been demonstrated, which utilizes internal charge transfer (ICT) between a weak electron-rich unit (weak donor) to a strong electron-deficient unit (strong acceptor).[3] Several polymers designed by this approach showed highly promising results with both high V$_{oc}$ and J$_{sc}$.[4] However, further improvement on J$_{sc}$ is limited by the relatively high LUMO levels and large band gap, because the electron withdrawing ability of the acceptor unit in those polymers, 4,7-dithien-2-yl-2,1,3-benzothiadiazole (DTBT), was not strong enough. Same problem was also found in other polymers containing DTBT acceptor unit.[1b,5] Thus, a stronger acceptor unit is needed to decrease LUMO levels of polymers. Therefore, the 5,6-difluoro-4,7-dithien-2-yl-2,1,3-benzothiadiazole (DTfBT) is envisioned. Two hydrogen atoms on BT unit are replaced by fluorine atoms with high electron negativity to decrease electron density on the benzene ring, making it a stronger acceptor. The twisting of polymer chains and interruption of electron delocalization is avoided because of the negligible steric hinderance of small radius fluorine atoms with flanking thiophene units. In addition, the two thiophene units would enhance polymer chain interaction to increase hole mobility.

Computational studies using density functional theory (DFT) approaches were performed to evaluate the potential use of DTfBT unit in high performance photovoltaic materials prior to synthesis. Benzo(1,2-b:4,5-b')dithiophene (BnDT) was chosen as the donor unit, because first, as a "weak donor", it would keep HOMO levels of the polymer down. Second, its symmetric nature and the rigid fused aromatic system can enhance electron delocalization and interchain interaction to improve charge mobility.[1f] Third, branched alkyl side chain enable good solubility and processibility in organic solvent and suitable miscibility with PCBM. Energy levels of the copolymer (PBnDT-DTfBT) (Scheme 6a) of BnDT unit and DTfBT unit was simulated and compared with its DTBT analogue (PBnDT-DTBT). A HOMO level of −5.30 eV and a LUMO level of −2.97 eV were shown for PBnDT-DTfBT. Both are decreased about 0.1 eV compared with those of PBnDT-DTBT, resulting in similar band gaps. Thus, higher PCE was expected for PBnDT-DTfBT based devices with a larger $V_{oc}$ and a similar $J_{sc}$.

Here in, we report the synthesis of the DTfBT monomer and PBnDT-DTfBT polymer. Our preliminary tests on its BHJ device demonstrate a large $V_{oc}$ of 0.91V, a high $J_{sc}$ of 12.0 mA/cm$^2$ and enhanced FF of 0.62. A record-high PCE of 6.86% was thus obtained with PC$_{61}$BM as electron acceptor without special treatments.[1e]

Scheme 6. (a) Chemical structure of PBnDT—DTfBT
(b) Synthetic Route of DTfBT and PBnDT—DTfBT polymer[a]

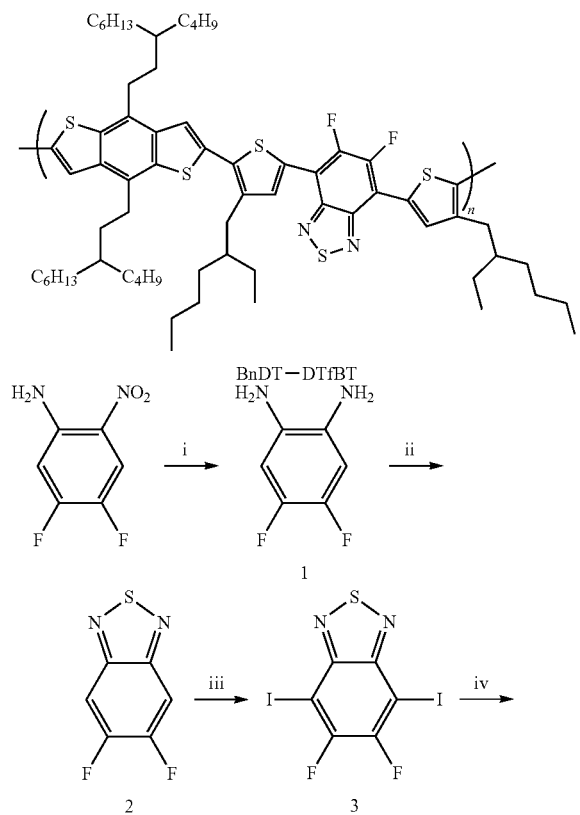

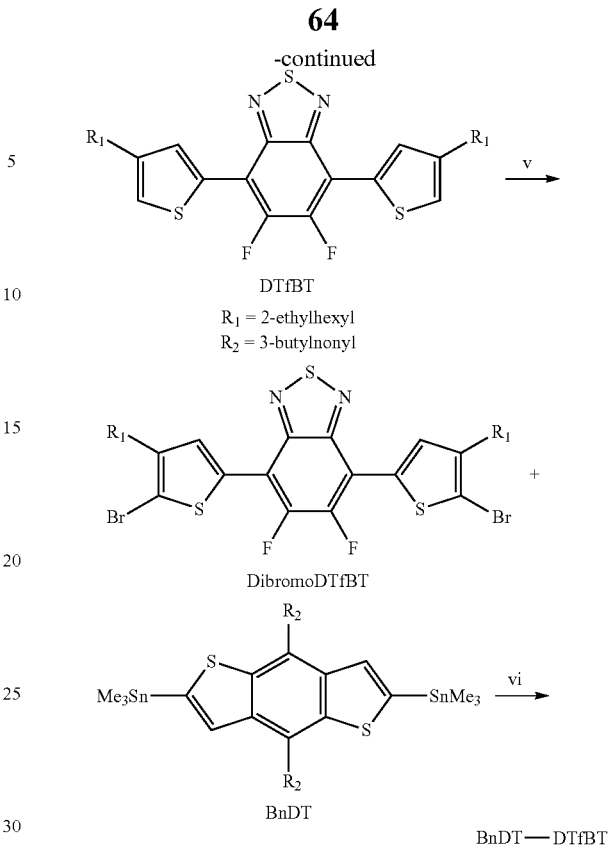

[a](i) Pd/C, H$_2$, ethyl acetate, 3 d; (ii) SOCl$_2$, Et$_3$N, chloroform, 5 h; (iii) I$_2$, fuming H$_2$SO$_4$, reflux, overnight; (iv) (2-ethylhexylthiophen-2-yl) trimethylstannane, Pd(PPh$_3$)$_4$, THF, reflux, 2 d; (v) NBS, THF, 8 h; (vi) Pd$_2$(dba)$_3$, P(o-tolyl)$_3$, o-xylene, Microwave, 150° C., 20 min.

Synthesis of DTfBT is shown in Scheme 6. 5,6-difluorobenzothiadiazole (2) was synthesized via Pd catalyzed hydrogenation followed by treating with SOCK, with overall yield of ~70%. The oxidative halogenation with I$_2$ and fuming sulfuric acid successfully iodinated the highly electron-deficient and deactivated benzene ring, giving unstable 3.[6] Stille coupling reaction was conducted immediately after previous reaction with excess amount of (2-ethylhexylthiophen-2-yl) trimethylstannane, giving DTfBT as orange solid in 43% yield from 2. The monomer dibromoDTfBT was obtained by NBS bromination of DTfBT.

PBnDT-DTfBT was prepared by a microwave-assisted Stille coupling reaction with 89% yield. To ensure good solubility, 2-ethylhexyl and 3-butylnonyl side chains were employed on DTfBT and BnDT, respectively.[7] However, the solubility of resulting polymer PBnDT-DTfBT is still low in common organic solvent at room temperature. Gel permeation chromatography (GPC) studies using TCB at 135° C. as the eluent showed number average molecular weight (M$_n$) of 33.8 kg/mol with a polydispersity index (PDI) of 2.6.

Figure 10:
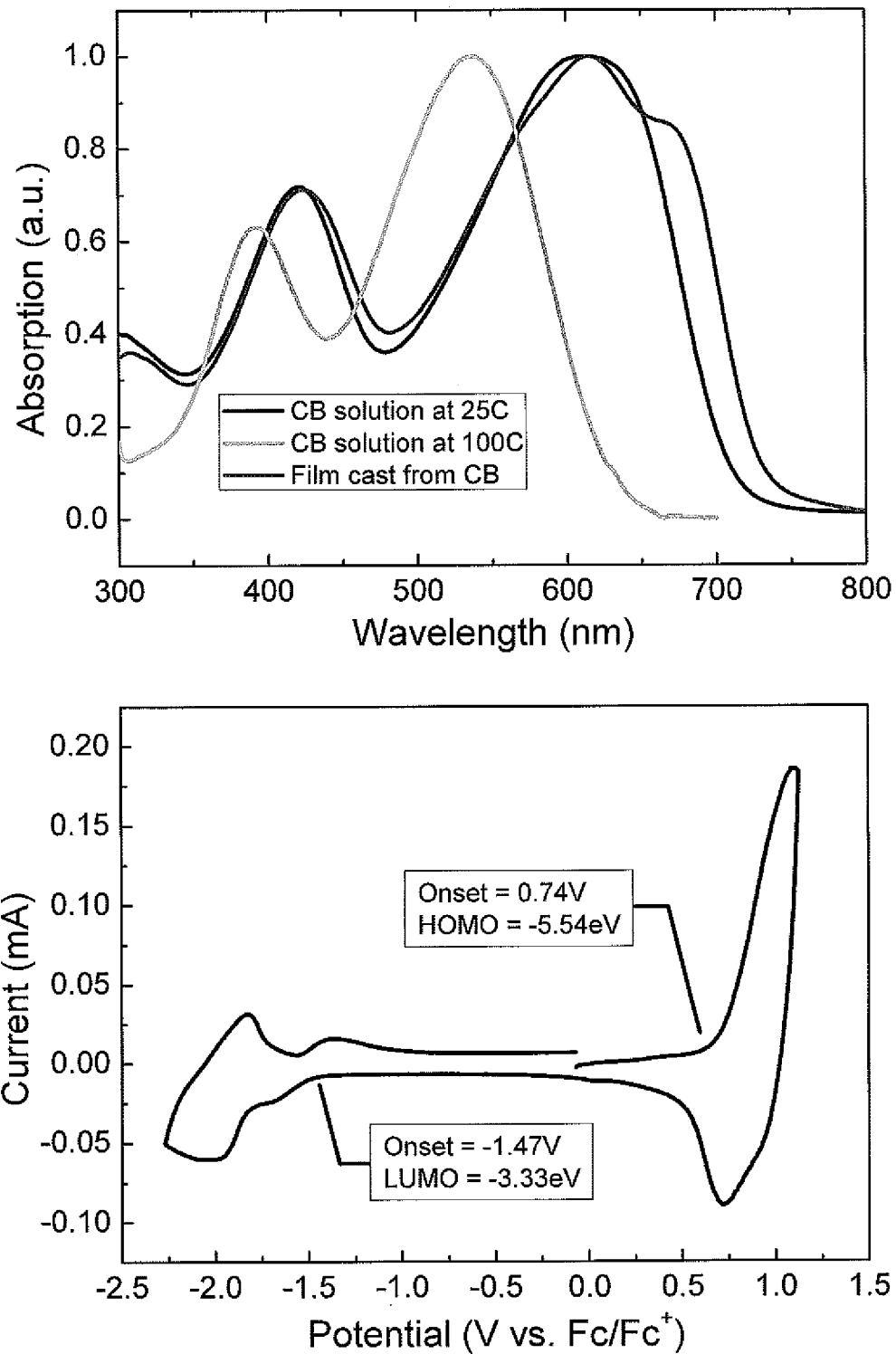
FIG. 10. (a) Absorption spectra of PBnDT-DTfBT in CB at room temperature (black), 100° C. (green) and thin film (red). (b) Cyclic voltammogram (50 mV s$^{-1}$) of PBnDT-DTfBT film drop cast on a glassy carbon electrode in Bu$_4$NBF$_4$/CH$_3$CN.
Figure 11:
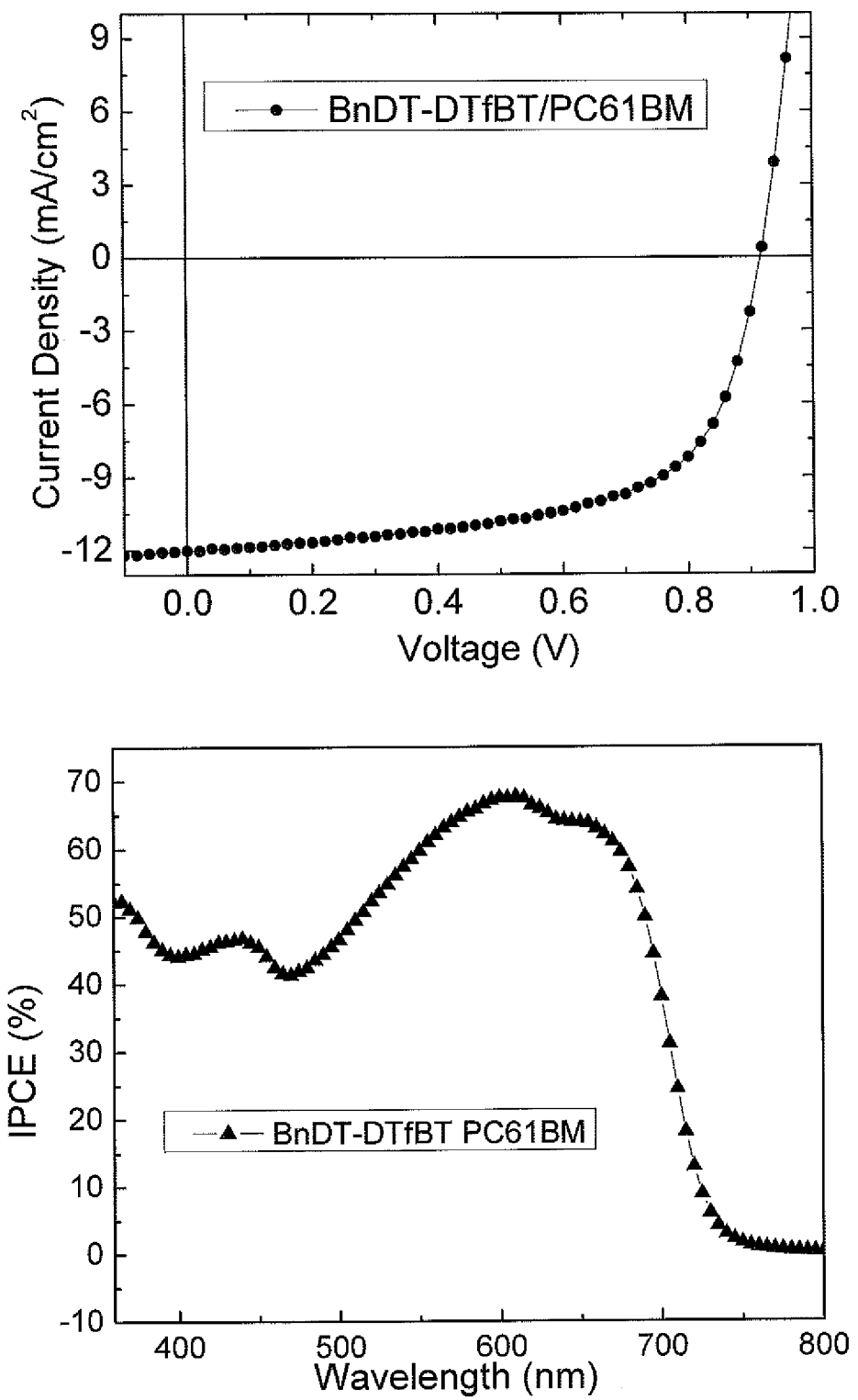
FIG. 11. (a) Characteristic J-V curves of the devices of polymer based BHJ solar cells under 1 Sun condition (100 mW/cm$^2$). (b) IPCE and absorption of semi-optimized devices.

UV-vis absorption spectra of PBnDT-DTfBT under various conditions are shown in FIG. 10a. The absorption of PBnDT-DTfBT solution in CB at room temperature is ca.80 nm redshifted comparing with the polymer solution in CB at 100° C., indicating significant polymer chain interactions and the formation of polymer chain aggregation at room temperature. Both the absorption spectra of polymer solution at room temperature and polymer film exhibit a same absorption maximum ($\lambda_{max}$) at 615 nm, suggesting similar polymer chain conformation at both states. A shoulder was observed in film absorption, indicating extra rigid-rod polymer chain packing in solid state.[1d] A band gap of 1.7 eV for PBnDT-DTfBT was calculated from absorption onset similar with that of PBnDT-DTBT. The electrochemical behavior of PBnDT-DTfBT measured by the cyclic voltammetry (CV) is shown in FIG. 11b. The HOMO and LUMO energy levels of PBnDT-DTfBT are both lower than those of PBnDT-DTBT resulting in similar band gaps, which agrees well with the DFT simulation.

BHJ solar cells were fabricated using PBnDT-DTfBT as electron donor material and $PC_{61}BM$ as electron acceptor materials with a general structure of ITO/PEDOT:PSS/PBnDT-DTfBT:$PC_{61}BM$/Ca(35 nm)/Al(70 nm). All the devices were tested under simulated AM1.5G illumination (100 mW/cm²). Typical current density-voltage (J-V) curve and the IPCE are shown in FIG. 11a. The best performing PBnDT-DTfBT/$PC_{61}BM$ BHJ solar cells were fabricated by spin-coating a polymer:$PC_{61}BM$ (1:1 w/w) solution in DCB onto a PEDOT:PSS layer with a thin film of ~95 nm. As expected, with deep HOMO level, PBnDT-DTfBT exhibits a $V_{oc}$ of 0.9V, 0.1V larger than PBnDT-DTBT devices. A $J_{sc}$ of 12.0 mA/cm² was also obtained, significantly improved from 9.7 mA/cm² in PBnDT-DTBT polymer devices, in spite of similar band gaps. Incident photo to current efficiency (IPCE) of PBnDT-DTfBT BHJ devices was thus measured (FIG. 11b). Significant photo-to-current response was obtained in nearly the entire visible range which suggests a highly efficient photoconversion process in the device. An IPCE>60% was observed spanning from 550 nm to 670 nm. A maximum IPCE of 67.6% at 610 nm represents one of the highest IPCE values in low band gap polymer solar cells. The calculated $J_{sc}$ by integrating the spectral response of the cells agrees well with photocurrent obtained by J-V measurements (within 2% error). This high IPCE response and a fill factor of 62.8% also indicate an improved active layer morphology which has been demonstrated in other fluorine containing polymer devices.[8] An impressive PCE of 6.86% was achieved in initial trials, which is among one of the highest PCE obtained in polymer/$PC_{61}BM$ BRJ solar cells.

In summary, a stronger acceptor—DTfBT—was successfully applied in constructing a low band gap polymer PBnDT-DTfBT with both decreased HOMO and LUMO levels by "weak donor—strong acceptor" strategy. Results showed both large V, of 0.91V and high $J_{sc}$ of 12.0 mA/cm², yielding 6.86% PCE in BHJ device with $PC_{61}BM$.

REFERENCES FOR EXAMPLE 4

(1) (a) Chen, H.-Y. et al., *Nat Photon* 2009, 3, 649; (b) Park, S. H. et al., *Nat. Photonics* 2009, 3, 297; (c) Zou, Y. et al., *J. Am. Chem. Soc.* 2010, 132, 5330; (d) Coffin, R. C. et al., *Nat. Chem.* 2009, 1, 657; (e) Piliego, C. et al., *J. Am. Chem. Soc.* 2010; (f) Liang, Y. et al., *J. Am. Chem. Soc.* 2009, 131, 56; (g) Liang, Y. et al., *Adv. Mater.* 2010, DOL: 10.1002/adma.200903528.
(2) Scharber, M. C. et al., *Adv. Mater.* 2006, 18, 789.
(3) (a) Roncali, *J. Macromol. Rapid Commun.* 2007, 28, 1761; (b) Zhang, Q. T. et al., *J. Am. Chem. Soc.* 1997, 119, 5065; (c) Zhou, H. et al., *ACS Appl. Mater. Interfaces* 2010, 2, 1377.
(4) (a) Zhou, H. et al., *Macromolecules* 2010, Submitted; (b) Price, S. C. et al., *Macromolecules* 2010, 43, 4609.
(5) (a) Qin, R. et al., *J. Am. Chem. Soc.* 2009, 131, 14612; (b) Huo, L. et al., *Angew. Chem. Int. Ed.* 2010, 49, 1500; (c) Zheng, Q. et al., *J. Am. Chem. Soc.* 2010, 132, 5394; (d) Wang, E. et al., *Appl. Phys. Lett.* 2008, 92, 033307; (e) Svensson, M. et al., *Adv. Mater.* 2003, 15, 988; (f) Blouin, N. et al., *J. Am. Chem. Soc.* 2008, 130, 732.
(6) Hellmann, M.; Bilbo, A. J.; Pummer, W. J. *J. Am. Chem. Soc.* 1955, 77, 3650.
(7) Zhou, H. X. et al., *Macromolecules* 2010, 43, 811.
(8) Kim, J. S. et al., *Adv. Mater.* 2010, 22, 1355.

EXAMPLE 5

Fluorine Substituted Conjugated Polymer of Medium Band Gap

Yields Efficient Polymer-Fullerene Solar Cells

Rapid and recent developments in the field of conjugated polymers have led to dramatic increases in polymer solar cell performance, reaching power conversion efficiencies over 6%.[1,2,3,4] Research activities on new materials development have been almost exclusively focused on creating polymers with low band gaps, in order to extend the light absorption to 900 nm and beyond for increased light harvesting.[1,5,6] However, medium (or even slightly wider) band gap polymers are still relevant to photovoltaics in their own right. Low band gap materials quite often are designed with higher than optimal HOMO energy levels in order to achieve a narrow band gap. While this provides a high short circuit current ($J_{sc}$) from the increased light absorption, the open circuit voltage ($V_{oc}$) suffers.[6] A high $V_{oc}$ is more readily achieved through medium band gap polymers with a low HOMO energy level.[7-9] Moreover, conjugated polymers usually have a relatively narrow absorption width,[10] which significantly limits the light absorption of these materials and leads to lower than expected $J_{sc}$. An emerging solution is to employ a tandem cell structure, stacking two cells with active layers absorbing different parts of the solar spectrum. This would cover a much wider portion of the solar influx, significantly improving the overall device efficiency.[11,12] In this regard, medium band gap polymers with high photovoltaic efficiency would be desirable in addition to high performance low band gap polymers.

Poly(3-hexylthiophene) has long been the standard medium band gap polymer used in tandem solar cells, since single bulk heterojunction (BHJ) cells of P3HT blended with PCBM exhibit a reliably measured power conversion efficiency between 4% and 5%.[13] However, P3HT exhibits a very high lying HOMO energy level of −5.1 eV, which limits the $V_{oc}$ of the resulting photovoltaic cells to a low value of 0.6 V. Second, P3HT based BHJ cell requires either thermal[13] or solvent annealing[14] to reach maximum performance, a time consuming process, which is not conducive to roll to roll high throughput manufacturing. Thus, the seemingly overlooked medium band gap polymers warrant further exploration.

Research efforts in this group have recently focused on developing low band gap intramolecular charge transfer (ICT) copolymers using the design motif outlined in Scheme 7. 1a.[15-18] The motif uses a band gap reducing aromatic group (e.g. benzothiadiazole) to obtain a low band gap, and two flanking thiophenes which provide planarity and a position to anchor solubilizing alkyl chains. To apply this motif to the design of medium band gap copolymers, an acceptor unit with a higher LUMO energy level is required in order to widen the band gap. One such candidate is the 2-alkyl-benzo[d][1,2,3]triazoles (TAZ), which requires a higher potential to reduce due to the substitution of the sulfur atom in benzothiadiazole with a nitrogen atom. The lone pair on the nitrogen atom is more basic than the lone pairs on sulfur, and is more easily donated into the triazole ring. This causes polymers employing benzotriazoles as the acceptor unit to be more electron rich, which leads to a higher LUMO energy level. Therefore, wider band gaps are observed for TAZ based polymers than the benzothiadiazole based counterparts. TAZ based polymers also provide an additional advantage of incorporating solubilizing alkyl chains onto the acceptor unit, rather than on the thiophene rings on the backbone of the polymer. Alkyl chains anchored to the thiophene rings on the polymer backbone may cause steric repulsion between the adjacent monomer units. Therefore, placing the alkyl chain away from the polymer backbone on the TAZ unit allows the polymer backbone to adopt a more planar conformation. We hypothesize that this increased planarity would increase the hole mobility of the resulting polymer.

While a wider band gap is a disadvantage in that less light is harvested from the solar spectrum, the larger gap between the HOMO and the LUMO on the polymer provides an opportunity to increase the open circuit voltage.[19] In order to increase the $V_{oc}$ while holding the band gap constant, the energy levels of both the HOMO and LUMO of the conjugated polymer must be decreased simultaneously. Thus, electron withdrawing groups would need to be added to the polymer. Fluorine has recently attracted attention as an electron withdrawing group used in high efficiency photovoltaic polymers.[1] Since it is only one small atom in size, it can be introduced onto the polymer backbone without any deleterious steric effects that a larger electron withdrawing group such as a nitro or trifluoromethyl group would incur. Density functional theory calculations predicted a 0.11 eV decrease in the HOMO energy level by adding two fluorine atoms to the benzotriazole unit. Thus, the fluorinated monomer, FTAZ, was envisioned and synthesized.

Herein we report two new polymers incorporating benzodithiophene (BnDT) as the donor and either benzotriazole (HTAZ) or fluorinated analog (FTAZ) as the acceptor. Both polymers show an optical gap of 2.0 eV, which is even slightly bigger than that of P3HT (1.9 eV). However, the photovoltaic performance of PBnDT-HTAZ is on par with that of P3HT, with an overall efficiency of 4.3% at an active layer thickness of 230 nm. More impressive results come from the PBnDT-FTAZ:PC$_{61}$BM based BHJ cells, which show a $V_{oc}$ of 0.79 V, a $J_{sc}$ of 12.45 mA/cm$^2$, and a very notable FF of 72.2%, leading to a highest overall efficiency of 7.1% with an active layer thickness of 250 nm. Furthermore, PBnDT-FTAZ based BHJ cells are able to achieve an efficiency of 6% at an unprecedented active layer thickness of 1 micron. All these boast the great potential of PBnDT-FTAZ in constructing low cost, high efficiency solar cells.

RESULTS AND DISCUSSION

Synthesis of Monomers and Polymers.

While HTAZ was synthesized according to literature reports,[20,21] the synthesis of the fluorinated monomer FTAZ is depicted in Scheme 7b. The synthesis began with a standard alkylation of 1.[22] Poor regioselectivity for the desired 2 position resulted in poor yields, which is typical for this type of reaction. In the second step, direct electrophilic bromination of the electron deficient fluorinated benzotriazole, 2, with molecular bromine resulted in low yield. Therefore, an alternative approach was explored to first activate the 4 and 7 positions of the benzotriazole by deprotonating the benzotriazole ring with LDA, and then quenching the resulting anion immediately with trimethylsilyl chloride. The resulting carbon-silicon bonds can then be brominated with excess bromine in chloroform at room temperature, affording 3 in 53% yield over two steps. A Negishi coupling followed by an NBS bromination then finished the synthesis of the fluorinated monomer FTAZ.

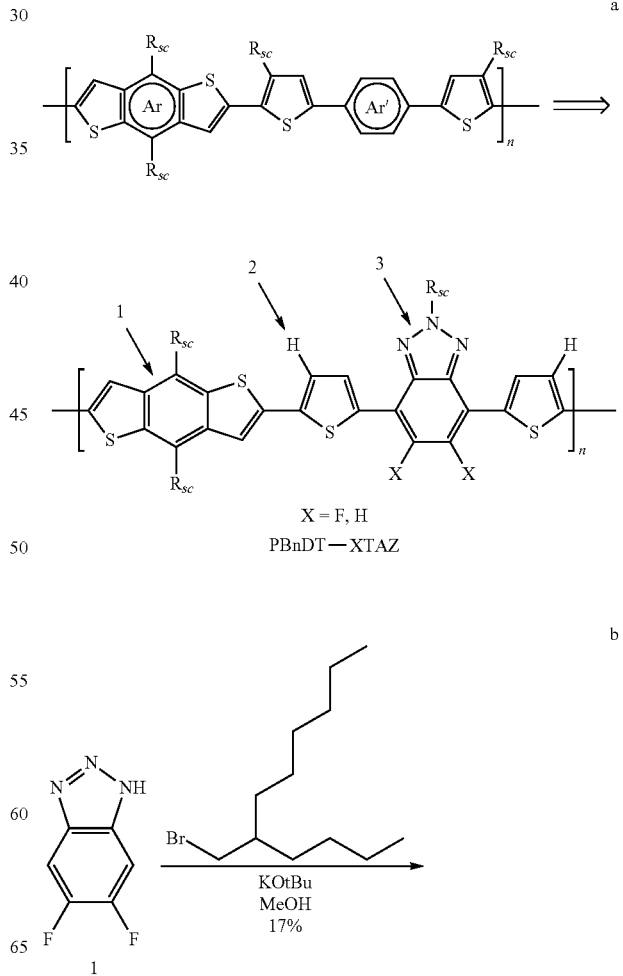

Scheme 7.

-continued

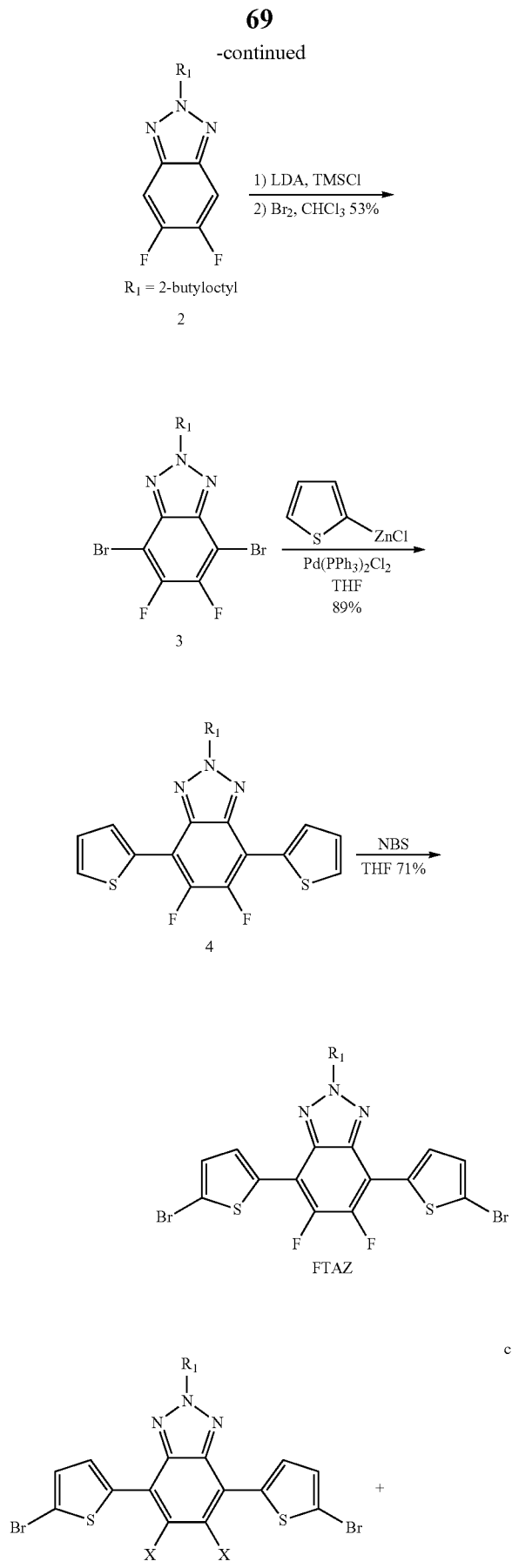

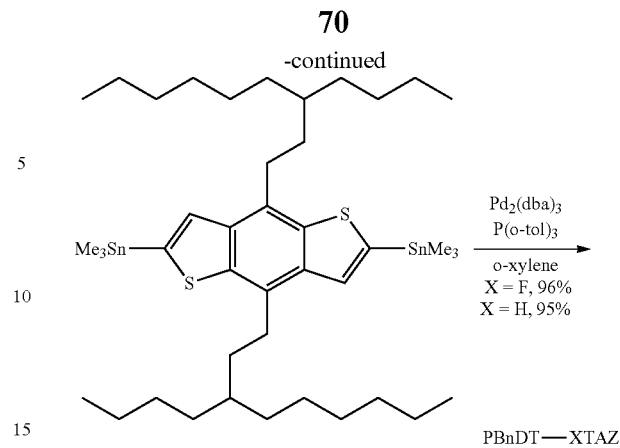

(a) Typical design motif used by our research group and others shown on the left. 1) Benzene was chosen as the Ar unit to provide a lower HOMO. 2) Movement of the solubilizing chains to the Ar' group reduces steric hindrance between the BnDT monomer and adjacent thiophenes. 3) Benzotriazole chosen as the band gap lowering aryl unit to provide a medium gap. Ar = Aryl unit used to control the HOMO energy level of the polymer. Ar' = Band gap reducing aromatic group. $R_{sc}$ = solubilizing alkyl chain. (b) Synthesis of FTAZ monomer. (c) Synthesis of polymers PBnDT—FTAZ and PBnDT—HTAZ with a Stille polycondensation polymerization.

Polymerization of the HTAZ and FTAZ monomers using standard microwave Stille polycondensation conditions[6] with the distannyl monomer 2,6-bis(trimethyltin)-4,8-di(3-butyl-nonyl)benzo[1,2-b:4,5-b']dithiophene produced the corresponding copolymers (PBnDT-HTAZ and PBnDT-FTAZ, Scheme 7c in yields greater than 95%. Both polymers were purified by Soxhlet extraction with methanol, ethyl acetate, hexanes, and chloroform. The resulting purple solids from the chloroform fraction exhibit high and nearly identical molecular weight distributions (Table 7).

Optical and Electrochemical Properties.

The intrinsic properties of the two polymers are summarized in Table 1. Both polymers exhibit nearly identical optical band gaps around 2.0 eV from the absorption edge of their thin films (FIG. 12c), though the fluorinated material has a slightly higher absorption coefficient. However, the fluorinated material shows a more pronounced peak at around 575 nm in solution at room temperature, which is associated with inter-chain interactions. And while both absorption spectra blue shift by about 12 nm when collected in boiling chlorobenzene, the interchain association band still remains at a higher relative intensity for the fluorinated material (PBnDT-FTAZ). This observed absorption behavior of PBnDT-FTAZ indicates that it aggregates in solution much more strongly than PBnDT-HTAZ.

Figure 12:
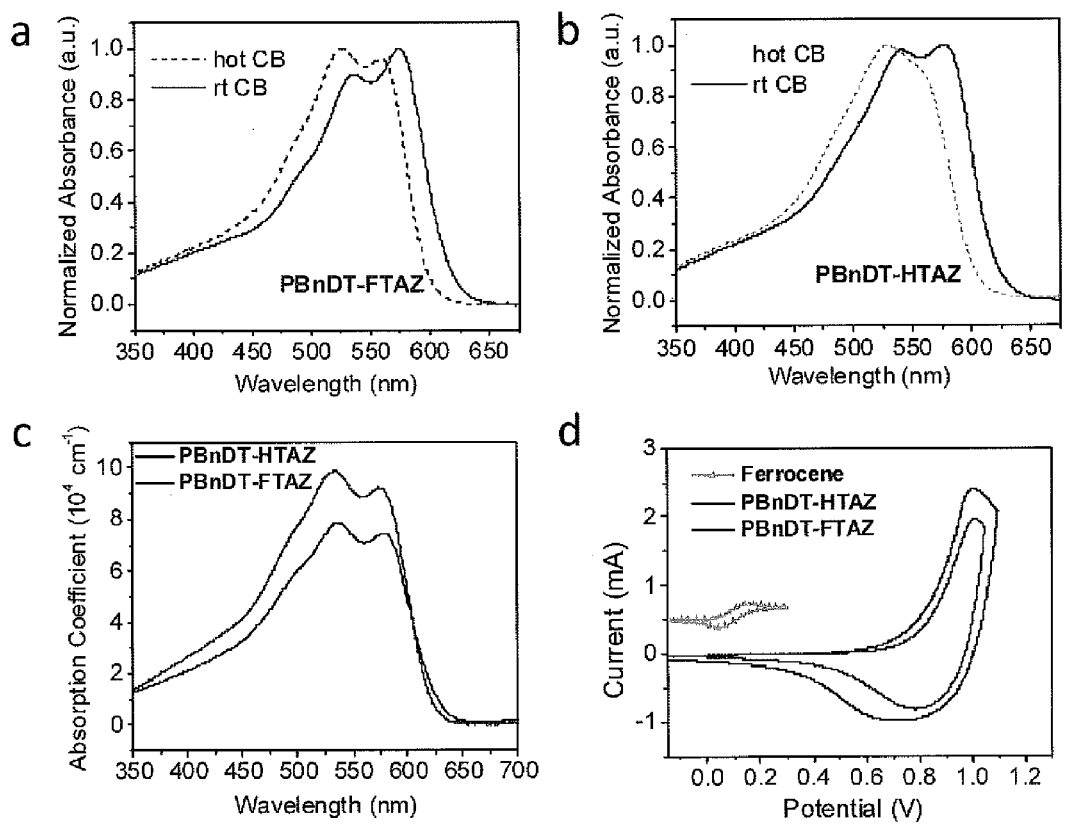
FIG. 12. Solution UV-Visible absorption spectra for a) PBnDT-FTAZ and b) PBnDT-HTAZ; c) Film UV-Vis absorption spectra for both polymers; d) The oxidative portion of the cyclic voltammogram for PBnDT-FTAZ and PBnDT-HTAZ. The ferrocene/ferrocenium redox couple is used as a standard (−4.8 eV) and is shifted up the Y-axis by 0.5 mA for clarity.

In addition to small differences in absorption spectra, the two polymers display very similar electrochemical oxidation characteristics as well (FIG. 12d). Cyclic voltammetry reveals reversible oxidation behavior for both polymers, with the fluorinated polymer (PBnDT-FTAZ) being oxidized only 0.07 V after PBnDT-HTAZ. This slight difference is also predicted by DFT calculations for the HOMO energy levels of each material. Both materials display HOMO energy levels at least 0.2 eV lower than the currently favored, wide band gap polymer, P3HT (−5.1 eV), implying that a higher $V_{oc}$ could be obtained than that of the P3HT based devices 0.6 V).

TABLE 7

Key polymer properties and calculated photovoltaic performances for PBnDT-HTAZ and PBnDT-FTAZ.

| Polymer | $M_n$/PDI[a] [kg/mol] | Film $E_g$[b] [eV] | Extinction Coefficient[c] [cm$^{-1}$] | HOMO (CV) [eV] | LUMO (CV) [eV] | DFT Calculated HOMO [eV] | $J_s$ (mA/cm$^2$) | $J_{so}$[d] (mA/cm$^2$) | $V_{oc}$[d] Cal (V) | $V_{oc}$ Measured (V) |
|---|---|---|---|---|---|---|---|---|---|---|
| PBnDT-HTAZ | 47.6/2.57 | 1.98 | 7.9 × 10$^4$ | −5.29 | −2.87 | −5.08 | 1.90 × 10$^{-5}$ | 33.64 | 0.68 | 0.71 |
| PBnDT-FTAZ | 42.2/2.36 | 2.00 | 9.8 × 10$^4$ | −5.36 | −3.05 | −5.19 | 1.60 × 10$^{-5}$ | 18.74 | 0.76 | 0.79 |

[a]$M_n$ = Number-average molecular weight determined by GPC in 1,2,4-trichlorobenzene at 135° C.
[b]Band gap calculated from the onset of the absorption of the solid film.
[c]Measured from Film absorption spectra at $\lambda_{max}$ (534 nm).
[d]Calculation based on HOMO measured from CV and using the saturation dark current density, according to equation $$V_{oc} \approx \frac{nKT}{q} \ln\left(\frac{J_{sc}}{J_{so}}\right) + \frac{\Delta E_{DA}}{2q}$$

The fluorinated material shows slightly reduced saturation dark currents which, in conjunction with a lower HOMO, leads to an increase in the open circuit voltage by 0.1 V (15%).

Photovoltaic Properties.

Figure 13:
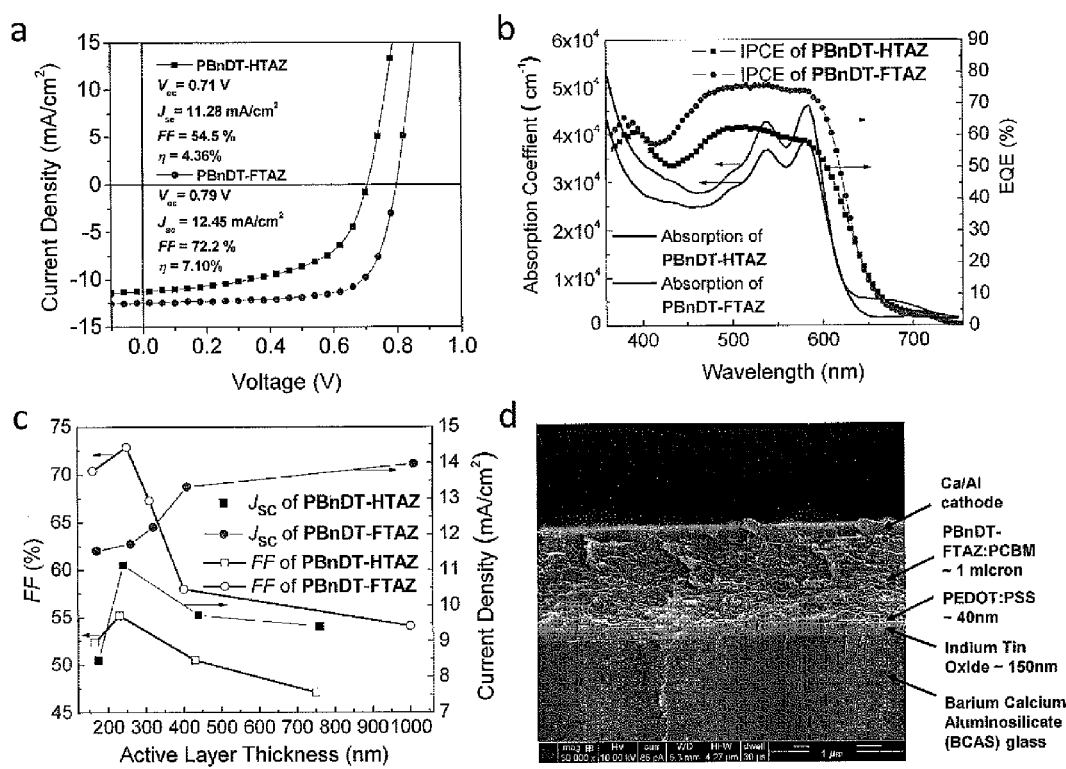
FIG. 13. (a) J-V curves for the highest performing cells for each polymer. The fluorine atoms cause increases in every performance category. PBnDT-FTAZ overall performs 76% better than PBnDT-HTAZ. (b) Incident photon to current efficiency and solid film absorption of each blend of polymer: PC$_{61}$BM. (c) Dependence of the FF and J$_{sc}$ on the thickness of the active layer. (d) SEM of 1 micron active layer that showed 6% power conversion efficiency (scale bar: 1 μm).

Optimized photovoltaic devices were obtained by spin casting a 1:2 blend of polymer:PC$_{61}$BM in 1,2,4-trichlorobenzene (TCB), and then allowing the trichlorobenzene to evaporate slowly in a petri dish. Solvents that evaporated faster such as dichlorobenzene and other ratios of polymer to PC$_{61}$BM produced suboptimal results. This is likely due to the extended solvent evaporation time from the higher boiling TCB, which allows more time for polymer chains to organize into a near optimal morphology during solvent annealing. Thickness optimizations were conducted and summarized in Table 2. While the optimal thickness for PBnDT-HTAZ is easily identified as around 230 nm with the highest $J_{sc}$ and FF among corresponding values associated with all thicknesses studied, the optimal thickness in the case of PBnDT-FTAZ is arguably estimated to be around 250 nm where the highest efficiency was obtained (7.1%) (FIG. 13a-13b). In fact, one particular feature of the fluorinated material (PBnDT-FTAZ) is its insensitivity to changes in active layer thickness. The $J_{sc}$ continuously rises as the thickness of the active layer of PBnDT-FTAZ:PC$_{61}$BM BHJ cells increases (FIG. 13c and Table 8). However, the fill factor peaks around 250 nm with a value of 72%, then drops off as the thickness increases. Nevertheless, an efficiency of 6% was still observed even at an unprecedented active layer thickness of 1 micron in the case of PBnDT-FTAZ (FIG. 13d).

It is intriguing to note that PBnDT-FTAZ performs almost twice as well as PBnDT-HTAZ, though the only difference between these two polymers is the two fluorine atoms on the benzotriazole unit. This is due to a 0.09 V increase in the $V_{oc}$, a 10% increase in the $J_{sc}$, and an increase from 55% to 72% in the FF of PBnDT-FTAZ based BHJ cells. The small increase in $V_{oc}$ can be explained by two factors. First, the HOMO energy level for PBnDT-FTAZ is 0.07 eV lower than the non-fluorinated material, due to the electron withdrawing effect of the fluorine atoms. Additionally, PBnDT-FTAZ also exhibits a slightly lower $J_{so}$ value (Table 7).[23,24] This is likely due to the repulsive nature of the fluorine atoms, which repel hydrocarbon materials.[25] This hypothesis was tested with X-ray diffraction spectroscopy (Table 9), and indeed a larger d-spacing was observed for the fluorinated polymer PBnDT-FTAZ than for the non-fluorinated material (18.6 Å vs. 17.5 Å). It is, therefore, not unreasonable to conclude that PC$_{61}$BM is also kept slightly farther away from the PBnDT-FTAZ chains during electron transfer reactions. This would increase the electron-hole charge transfer complex separation and slow down bimolecular recombination. This retardation of the recombination rate has also been witnessed in fluorinated dyes in dye sensitized solar cells.[26] By combining the HOMO energy level and the $J_{so}$, the calculated $V_{oc}$ matches the experimental value extremely well (Table 7), quantitatively explaining the difference in the observed $V_{oc}$.

TABLE 8

Thickness optimizations for photovoltaic devices.

| Polymer | Polymer:PC$_{61}$BM (w:w) | Thickness [nm] | $V_{oc}$ [V] | $J_{sc}$ [mA/cm$^2$] | FF [%] | $\eta_{average}$ ($\eta_{max}$) [%] |
|---|---|---|---|---|---|---|
| PBnDT-HTAZ | 1:2 | 165 | 0.66 | 8.47 | 52.4 | 2.94 (3.27) |
|  | 1:2 | 230 | 0.70 | 11.14 | 55.2 | 4.30 (4.36) |
|  | 1:2 | 430 | 0.66 | 9.73 | 50.5 | 3.25 (3.29) |
|  | 1:2 | 750 | 0.71 | 9.41 | 47.1 | 3.14 (3.18) |
| PBnDT-FTAZ | 1:2 | 160 | 0.74 | 11.54 | 70.4 | 6.03 (6.49) |
|  | 1:2 | 250 | 0.79 | 11.83 | 72.9 | 6.81 (7.10) |
|  | 1:2 | 310 | 0.79 | 12.20 | 67.3 | 6.47 (6.76) |
|  | 1:2 | 400 | 0.74 | 13.33 | 58.0 | 5.83 (6.17) |
|  | 1:2 | 1000 | 0.74 | 13.97 | 54.1 | 5.60 (6.06) |

The ability of the fluorinated polymer to maintain very high FF even at active layer thicknesses above 200 nm, and the high $J_{sc}$ are likely due to the high hole mobility of the polymer (Table 9). The hole mobility of PBnDT-FTAZ is an order of magnitude higher than the copolymer without fluorines in both neat polymer films, and when blended with $PC_{61}BM$. The mobility values for the PBnDT-FTAZ:$PC_{61}$BM blend ($1×10^{-3}$ cm$^2$/V·s) are the same order of magnitude as P3HT blends ($2×10^{-4}$ cm$^2$/V·s) in BHJ devices.[27] Hence, we attribute the large increase in $J_{sc}$ and FF, at least partially, to the increased hole mobility of the fluorinated polymer.

TABLE 9

X-Ray diffraction results and SCLC measured hole mobilities for PBnDT-HTAZ and PBnDT-FTAZ.

| Polymer | SCLC measurement | | XRD measurement | |
|---|---|---|---|---|
| | Thickness (nm) | Mobility (cm$^2$/V · s) | 2θ [°] | d-spacing [Å] |
| PBnDT-HTAZ Only | 340 | $3.34 × 10^{-6}$ | 5.05 | 17.50 |
| PBnDT-HTAZ: PCBM (1:2) | 270 | $2.94 × 10^{-4}$ | 4.96 | 17.82 |
| PBnDT-FTAZ Only | 440 | $6.76 × 10^{-5}$ | 4.73 | 18.68 |
| PBnDT-FTAZ: PCBM (1:2) | 170 | $1.03 × 10^{-3}$ | 4.72 | 18.72 |

Conclusions.

In summary, two nearly identical polymers with a medium band gap of 2.0 eV have been designed and synthesized following our design motif. The only structural difference between the two is that PBnDT-FTAZ bears two fluorine atoms on the benzotriazole ring of the PBnDT-HTAZ. While the photovoltaic performance of PBnDT-HTAZ based BHJ solar cells is already on par with that of P3HT based ones, a pleasant surprise comes from the fluorinated material, PBnDT-FTAZ, with a peak device efficiency of 7.1% observed. Though the two fluorine atoms have a minimal effect on the optical and electrochemical properties of the polymer, they have a profound effect on the hole mobility of the polymer, and thus the photovoltaic performance. PBnDT-FTAZ based BHJ devices consistently show a higher FF and $J_{sc}$ than PBnDT-HTAZ based devices at comparable thicknesses. Such a high hole mobility likely also explains that fact that PBnDT-FTAZ:$PC_{61}$BM solar cell can still achieve over 6% efficiency even at an unprecedented thickness of 1 micron (of the active layer). However, other factors are likely contributing to the increase in efficiency. Investigations to further understand the impact of the fluorine atoms on the morphology, self assembly behavior, and exciton related dynamics are currently underway.

Experimental

General Methods.

All reagents and chemicals were purchased from commercial sources (Aldrich, Acros, Strem, Fluka) and used without further purification unless stated otherwise. Reagent grade solvents were dried when necessary and purified by distillation. $^1$H nuclear magnetic resonance (NMR) spectra were obtained at 400 or 300 MHz as solutions in CDCl$_3$. $^{13}$C NMR proton decoupled spectra were obtained at 100 MHz as solutions in CDCl$_3$. Chemical shifts are reported in parts per million (ppm, δ) and referenced from tetramethylsilane. Coupling constants are reported in hertz (Hz). Spectral splitting patterns are designated as s, singlet; d, doublet; dd, doublet of doublets; t, triplet; m, multiplet; and br, broad. Melting points are uncorrected. UV-vis absorption spectra were obtained by a Shimadzu UV-2401PC spectrophotometer. For the measurements of thin films, the polymer was spincoated at 600 rpm onto precleaned glass slides from 10 mg/mL polymer solution in chlorobenzene and dried slowly in a Petri dish for 3 h. Gel permeation chromatography (GPC) measurements were performed on a Polymer Laboratories PL-GPC 220 instrument, using 1,2,4-trichlorobenzene as the eluent (stabilized with 125 ppm BHT) at 135° C. The obtained molecular weight is relative to polystyrene standards. Cyclic voltammetry measurements were carried out using a Bioanalytical Systems (BAS) Epsilon potentiostat equipped with a standard three-electrode configuration. Typically, a three-electrode cell equipped with a glassy carbon working electrode, a Ag/AgNO$_3$ (0.01 M in anhydrous acetonitrile) reference electrode, and a Pt wire counter electrode were employed. The measurements were done in anhydrous acetonitrile with tetrabutylammonium hexafluorophosphate (0.1 M) as the supporting electrolyte under an argon atmosphere at a scan rate of 100 mV/s. Polymer films were drop-cast onto the glassy carbon working electrode from a 2.5 mg/mL chloroform solution and dried under house nitrogen stream prior to measurements. The potential of Ag/AgNO$_3$ reference electrode was internally calibrated by using the ferrocene/ferrocenium redox couple ($F_c/F_c^+$). The electrochemical onsets were determined at the position where the current starts to differ from the baseline. The highest occupied molecular orbital (HOMO) in electron volts was calculated from the onset of the oxidation potential ($E_{ox}$) according to the following equation.

$$HOMO = -[4.8\ eV + e(E_{ox} - E_{Fc/Fc+})]$$

Microwave reactions were performed using a CEM Discover Benchmate microwave reactor.

Polymer Solar Cell Fabrication and Testing.

Glass substrates coated with patterned tin-doped indium oxide (ITO) were purchased from Thin Film Devices, Inc. Prior to use, the substrates were ultrasonicated for 15 minutes in 2-propanol. The substrates were dried under a stream of nitrogen and subjected to the treatment of UV-Ozone for 15 min. A 0.45 μm filtered dispersion of PEDOT:PSS in water (Baytron PH500) was then spun cast onto clean ITO substrates at 4000 rpm for 60 s and then baked at 140° C. for 10 min to give a thin film with a thickness of 40 mm. A 1:2 w/w blend of polymer:PCBM at a 12 mg/mL concentration of polymer was dissolved in trichlorobenzene with heating at 140° C. overnight, filtered through a 1 μm poly(tetrafluoroethylene) (PTFE) filter, and spun cast between 400-1200 rpm for 60 s onto the PEDOT:PSS layer. The substrates were then dried at room temperature under N$_2$ for 12 h. The devices were finished for measurement after thermal deposition of a 30 nm film of calcium and then a 100 nm aluminum film as the cathode at a pressure of ~$1×10^{-6}$ mbar. There are eight devices per substrate, with an active area of 12 mm$^2$ per device. The thicknesses of films were recorded by a profilometer (Alpha-Step 200, Tencor Instruments), and AFM Images were taken using an Asylum Research MFP3D Atomic Force Microscope. Device characterization was carried out under AM 1.5G irradiation with the intensity of 100 mW/cm$^2$ (Oriel 91160, 300 W) calibrated by a NREL certified standard silicon cell. Current density versus potential (1-V) curves were recorded with a Keithley 2400 digital source meter. EQE were detected under monochromatic illumination (Oriel Cornerstone 260¼ m monochromator equipped with Oriel 70613NS QTH lamp) and the calibration of the incident light was performed with a monocrystalline silicon diode. All fabrication steps after adding the PEDOT: PSS layer onto ITO substrate, and characterizations were performed in a glove box under nitrogen atmosphere. For mobility measurements,[28] the hole-only devices in a configuration of ITO/PEDOT:PSS (45 nm)/polymer-PCBM/Pd (40 nm) were fabricated. The experimental dark current densities J of polymer:PCBM blends were measured when applied with voltage from 0 to 6 V. The applied voltage V was corrected from the built-in voltage $V_{bi}$ which was taken as a compensation voltage $V_{bi}=V_{oc}+0.05$ V and the voltage drop $V_{bi}$ across the ITO/PEDOT:PSS series resistance and contact resistance, which is found to be around 35Ω from a reference device without the polymer layer. From the plots of $J^{0.5}$ vs V, hole mobilities of copolymers can be deduced from the equation $$J = \frac{9}{8}\varepsilon_r\varepsilon_0\mu_h\frac{V^2}{L^3}$$

where $\varepsilon_0$ is the permittivity of free space, $\varepsilon_r$ is the dielectric constant of the polymer which is assumed to be around 3 for the conjugated polymers, $\mu_h$ is the hole mobility, V is the voltage drop across the device, and L is the film thickness of active layer.

Synthesis

Reagents.

All solvents are ACS grade unless otherwise noted. Anhydrous THF was obtained by distillation from sodium/benzophenone prior to use. Diisopropylamine was distilled from potassium hydroxide prior to use. 4,7-dibromo-2-(2-butyloctyl)-2H-benzo[d][1,2,3]triazole(Balan, A. et al., *Chem. Mater.* 20 (24), 7510-7513 (2008); Tanimoto, A. & Yamamoto, T., *Macromolecules* 39 (10), 3546-3552 (2006)) 2,6-Bis(trimethyltin)-4,8-(3-butylnonyl)benzo[1,2-b:4,5-b']dithiophene, 2-butyloctylbromide, and 5,6-difluoro-1H-benzo[d][1,2,3]triazole were prepared according to modified literature procedures (Pan, H. et al., *Chemistry of Materials* 18 (14), 3237-3241 (2006); Tylleman, B. t. et al., *Chem. Mater.* 21 (13), 2789-2797 (2009); Charushin, V. N. et al., *Mendeleev Commun.* 15 (2), 45-46 (2005)). All reagents were purchased from VWR, Fisher Scientific, Dynamic Absorbents, Silicycle, Accela ChemBio Inc., and were used without further purification.

4,7-bis(5-bromothiophen-2-yl)-2-(2-butyloctyl)-2H-benzo[d][1,2,3]triazole (HTAZ).

Thiophene (3.01 g, 2.5 eq) was dissolved in dry THF (40 mL) in a flame dried flask under argon. The mixture was cooled to 0° C. in an ice bath, and 1.6M n-BuLi in hexanes (22.8 mL, 2.55 eq) was added dropwise over 3 minutes. The solution was stirred for 35 min maintaining the temperature at 0° C., and then anhydrous $ZnCl_2$ (5.07 g, 2.6 eq) was added as a solution in 40 mL dry THF. The reaction was stirred for 5 min at 0° C., and then $Pd(PPh_3)_2Cl_2$ (602 mg, 6 mol %) was added in one portion. 4,7-dibromo-2-(2-butyloctyl)-2H-benzo[d][1,2,3]triazole (6.39 g, 1.0 eq) was then added via cannula as a solution in 20 mL of dry THF. The reaction mixture was then heated to reflux, and stirred for 16 h. The reaction mixture was then poured into water and extracted with ethyl acetate. The organic layer was then washed with water (3×), dried ($MgSO_4$), filtered, concentrated in vacuo, and purified by column chromatography on silica gel using 4:1 hexanes:$CH_2Cl_2$ as the eluent. The resulting fluorescent yellow solid was then dissolved into THF (80 mL), and N-bromosuccinimide (2.89 g, 2.0 eq) was added in one portion. The reaction mixture was stirred for 3.5 h, and then poured into saturated $NaHCO_3$ solution and extracted with ethyl acetate. The organic phase was then washed with water (3×), dried ($MgSO_4$), filtered, and concentrated in vacuo. The material was then purified by column chromatography on silica gel, using 3:1 hexanes:chloroform as the eluent. The resulting yellow solid (HTAZ) was then recrystallized twice from isopropanol to yield a yellow powder. Yield (2 steps): 2.79 g (32%). Fluorescent yellow solid; mp 70° C. $^1$H NMR ($CDCl_3$, 400 MHz, δ): 7.76 (d, $^3J_{HH}$=3.6 Hz, 2H), 7.46 (s, 2H), 7.10 (d, $^3J_{HH}$=4 Hz, 2H), 4.71 (d, $^3J_{HH}$=6.4 Hz, 2H), 2.27 (m, 1H), 1.26 (m, 16H), 0.90 (t, $^3J_{HH}$=7.2 Hz, 3H), 0.86 (t, $^3J_{HH}$=6 Hz, 3H). $^{13}$C NMR ($CDCl_3$, 100 MHz, δ): 141.55, 141.24, 130.80, 126.81, 122.90, 122.01, 113.16, 59.88, 39.09, 31.82, 31.38, 31.15, 29.56, 28.45, 26.17, 22.96, 22.65, 14.09. Anal. Calcd for $C_{26}H_{31}Br_2N_3S_2$: C, 51.24; H, 5.13; N, 6.89. Found: C, 51.52; H, 4.95; N, 6.88.

Polymerization of PBnDT-HTAZ.

2,6-Bis(trimethyltin)-4,8-(3-butylnonyl)benzo[1,2-b:4,5-b']dithiophene (132 mg, 1.0 eq), HTAZ (91.4 mg, 1.0 eq), $Pd_2(dba)_3$ (2.8 mg, 0.02 eq), and tri(o-tolyl)phosphine (7.2 mg, 0.16 eq) were combined in a dry microwave vial. The vial was sealed with a septum cap, and then evacuated and refilled with argon three times. Dry, oxygen free o-xylene (0.75 mL) was added. The mixture was then reacted in a microwave reactor for 20 min, at 200° C. (at 300 W), and then cooled to room temperature. The reaction mixture was diluted with chlorobenzene (3 mL), and then the polymer solution was precipitated into methanol (100 mL) at room temperature. The resulting purple-black solid was filtered into a Soxhlet thimble, and extracted with methanol, ethyl acetate, hexanes, and chloroform until the wash from each extraction was colorless. When there was no solid remaining in the thimble, the chloroform fraction was concentrated, and chlorobenzene was added (5 mL). The polymer solution was then precipitated into methanol at room temperature, filtered, and dried under vacuum at 0.5 mmHg. Yield: 143 mg (95%). Purple metallic solid. $^1$H NMR @ 400K ($C_2D_2Cl_4$, 400 MHz, δ): 7.86, 7.23, 4.87, 3.14, 2.41, 1.87, 1.50, 1.08. GPC (1,2,4-trichlorobenzene at 135° C.): $M_n$=47.6 kg/mol, $M_w$=133.4 kg/mol, PDI=2.57.

2-(2-butyloctyl)-5,6-difluoro-2H-benzo[d][1,2,3]triazole (2).

5,6-difluoro-1H-benzo[d][1,2,3]triazole (8.04 g, 1.0 eq), potassium tert-butoxide (5.87 g, 1.01 eq), and 2-butyloctylbromide (13.04 g, 1.01 eq) were dissolved in 130 mL of methanol. The reaction was heated to reflux for 17 h. The reaction mixture was then poured into saturated $NH_4Cl$ solution, and extracted with ethyl acetate. The organic layer was washed with water (2×), dried ($Na_2SO_4$), filtered, concentrated in vacuo, and purified by column chromatography on silica gel using 10:1 hexanes:ethyl acetate as the eluent. Yield: 2.88 g (17%). Colorless oil. $^1$H NMR ($CDCl_3$, 400 MHz, δ): 7.59 (t, $^3J_{THF}$=8.4 Hz, 2H), 4.58 (d, $^3J_{HH}$=6.8 Hz, 2H), 2.22 (m, 1H), 1.28 (m, 16H), 0.86 (t, $^3J_{HF}$=5.6 Hz, 6H).

4,7-dibromo-2-(2-butyloctyl)-5,6-difluoro-2H-benzo[d][1,2,3]triazole (3).

1.6M n-BuLi in hexanes (12.5 mL, 2.25 eq) was added dropwise over 3 min to a solution of diisopropylamine (3.10 mL, 2.5 eq) and dry THF (90 mL) under argon at −78° C. The solution was stirred for 15 min, and then a solution of Compound 2 (2.88 g, 1.0 eq) and trimethylsilyl chloride (3.1 mL, 2.75 eq) in dry THF (35 mL) was added dropwise over 10 minutes at −78° C. −78° C. was maintained while the reaction was stirred for 3 h, and then the reaction was quenched with 10 mL of saturated NH$_4$Cl. The reaction was warmed to room temperature and poured into saturated NH$_4$Cl. The mixture was extracted with ethyl acetate, washed with water (3×), dried (MgSO$_4$), and concentrated in vacuo. The residue was then dissolved into CHCl$_3$ (30 mL), and bromine (3.6 mL, 8.0 eq) was added in one portion, and the reaction was stirred for 16 h at room temperature, shielded from light. The reaction was then poured into a mixture of 10% NaOH and ice, and extracted with methylene chloride. The organic layer was washed with brine, dried (MgSO$_4$), and purified by column chromatography on silica gel using 4:1 hexanes:methylene chloride as the eluent. Yield (2 steps): 2.28 g (53%). Colorless oil. $^1$H NMR (CDCl$_3$, 300 MHz, δ): 4.65 (d, $^3J_{HH}$=7.2 Hz, 2H), 2.31 (m, 1H), 1.24 (m, 16H), 0.87 (m, 6H). $^{13}$C NMR (CDCl$_3$, 100 MHz, δ): 149.07 (dd, $^1J_{CF}$=253 Hz, $^2J_{CF}$=20 Hz), 138.86 (t, $^{3,4}J_{CF}$=2.5 Hz), 96.10 (dd, $^2J_{CF}$=15 Hz, $^3J_{CF}$=9 Hz), 61.11, 38.98, 31.64, 31.08, 30.79, 29.40, 28.18, 25.93, 22.81, 22.57, 14.05, 13.92.

2-(2-butyloctyl)-5,6-difluoro-4,7-di(thiophen-2-yl)-2,1-benzo[d][1,2,3]triazole (4).

Thiophene (0.87 g, 2.25 eq) was dissolved into dry THF (20 mL), and cooled to 0° C. under argon. 1.6M n-BuLi in hexanes (6.6 mL, 2.3 eq) was added dropwise over 3 min. The reaction was allowed to stir at 0° C. for 35 min, and then a solution of anhydrous ZnCl$_2$ (1.47 g, 2.35 eq) in dry THF (20 mL) was added via syringe at 0° C. After 5 min, Pd(PPh$_3$)$_2$Cl$_2$ (193 mg, 6 mol %) was added in one portion at 0° C. Then compound 3 (2.21 g, 1.0 eq) was added via syringe as a solution in dry THF (15 mL). The reaction mixture was then heated to reflux, and stirred for 16 h. The reaction was then poured into water, and extracted with ethyl acetate. The organic layer was washed with water (3×), dried (MgSO$_4$), filtered, concentrated in vacuo, and purified by column chromatography on silica gel using 4:1 hexanes:methylene chloride as the eluent. Yield: 1.99 g (89%). Fluorescent yellow solid. $^1$H NMR (CDCl$_3$, 300 MHz, δ): 8.33 (dd, $^3J_{HH}$=3.9 Hz, $^4J_{HH}$=0.9 Hz, 2H), 7.55 (dd, $^3J_{HH}$=5.1 Hz, $^4J_{HH}$=1.2 Hz, 2H), 7.24 (m, 2H), 4.73 (d, $^3J_{HH}$=6.6 Hz, 2H), 2.86 (m, 1H), 1.26 (m, 16H), 0.89 (m, 6H).

4,7-bis(5-bromothiophen-2-yl)-2-(2-butyloctyl)-5,6-difluoro-2H-benzo[d][1,2,3]triazole (FTAZ).

Combine 4 (1.99 g, 1.0 eq), N-bromosuccinimide (1.46 g, 2.0 eq), and THF (75 mL). Stir for 20 hours at room temperature, and then pour the reaction mixture into a saturated solution of sodium bicarbonate. Extract with methylene chloride, dried (MgSO$_4$), filtered, and then silca gel was added. The slurry was concentrated in vacuo, and the resulting solid purified by column chromatography on silica gel using 10:1 hexanes:methylene chloride as the eluent. After repeating the chromatography step a second time, a fluorescent yellow solid was obtained in purity sufficient for polymerization. Yield: 1.87 g (71%). Fluorescent yellow solid; mp 76° C. $^1$H NMR (CDCl$_3$, 400 MHz, δ): 7.97 (d, $^3J_{HH}$=4 Hz, 2H), 7.13 (d, $^3J_{HH}$=4 Hz, 2H), 4.68 (d, $^3J_{HH}$=6.4 Hz, 2H), 2.23 (m, 1H), 1.40 (m, 4H), 1.27 (m, 12H), 0.91 (t, $^3J_{HH}$=7.2 Hz, 3H), 0.86 (t, $^3J_{HH}$=6.8 Hz, 3H). $^{13}$C NMR (CDCl$_3$, 100 MHz, δ): 146.89 (dd, $^1J_{CF}$=252 Hz, $^2J_{CF}$=19 Hz), 137.01 (t, $^{3,4}J_{CF}$=4.2 Hz), 133.76, 130.26 (m), 130.19, 115.92 (m), 109.29 (dd, $^3J_{CF}$=9.5 Hz, $^4J_{CF}$=4.4 Hz), 59.84, 39.10, 31.84, 31.41, 31.17, 29.57, 28.47, 26.20, 22.97, 22.66, 14.09. Anal. Calcd for C$_{26}$H$_{29}$Br$_2$F$_2$N$_3$S$_2$: C, 48.38; H, 4.53; N, 6.51. Found: C, 48.20; H, 4.55; N, 6.62.

Polymerization of PBnDT-FTAZ.

2,6-Bis(trimethyltin)-4,8-(3-butylnonyl)benzo[1,2-b:4,5-b']dithiophene (132 mg, 1.0 eq), FTAZ (97 mg, 1.0 eq), Pd$_2$(dba)$_3$ (2.8 mg, 0.02 eq), and tri(o-tolyl)phosphine (7.2 mg, 0.16 eq) were combined in a dry microwave vial. The vial was then sealed with a septum cap, and then evacuated and refilled with argon three times. Dry, oxygen free o-xylene (0.75 mL) was added. The mixture was then reacted in a microwave reactor for 20 min, at 200° C. (at 300 W), and then cooled to room temperature. The reaction mixture was then diluted with chlorobenzene (3 mL), and then the polymer solution was precipitated into methanol (100 mL) at room temperature. The resulting purple-black solid was filtered into a Soxhlet thimble, and extracted with methanol, ethyl acetate, hexanes, and chloroform until the wash from each extraction was colorless. When there was no solid remaining in the Soxhlet thimble, the chloroform fraction was then concentrated, and chlorobenzene was added (5 mL). The polymer solution was then precipitated into methanol at room temperature, filtered, and dried under vacuum at 0.5 mmHg. Yield: 153 mg (98%). Purple metallic solid. $^1$H NMR @ 400K (C$_2$D$_2$Cl$_4$, 400 MHz, δ): 8.20, 7.26, 4.84, 3.07, 2.46, 1.51, 1.14, 1.05. GPC (1,2,4-trichlorobenzene at 135° C.): M$_n$=42.2 kg/mol, M$_w$=99.9 kg/mol, PDI=2.36.

REFERENCES FOR EXAMPLE 5

(1) Chen, H.-Y. et al., *Nat. Photonics* 2009, 3, 649.
(2) Park, S. H. et al., *Nat. Photonics* 2009, 3, 297.
(3) Piliego, C. et al., *J. Am. Chem. Soc.* 2010, 132, 7595.
(4) Zhao, G. et al., *Adv. Mater.* 2010, 22, 4355.
(5) Bijleveld, J. C. et al., *J. Am. Chem. Soc.* 2009, 131, 16616.
(6) Coffin, R. C. et al., *Nat. Chem.* 2009, 1, 657.
(7) Zhang, F. et al., *Adv. Funct. Mater.* 2006, 16, 667.
(8) Brabec, C. J. et al., *Appl. Phys. Lett.* 2001, 78, 841.
(10) Beaujuge, P. M. et al., *Acc. Chem. Res.* 2010, 43, 1396.
(11) Kim, J. Y. et al., *Science* 2007, 317, 222.
(12) Dennler, G. et al., *Adv. Mater.* 2008, 20, 579.
(13) Ma, W. et al., *Adv. Fund'. Mater.* 2005, 15, 1617.
(14) Li, G. et al., *Nat. Mater.* 2005, 4, 864.
(15) Price, S. C. et al., *Macromolecules* 2010, 43, 4609.
(16) Zhou, H. et al., *Angew. Chem.*, Int. Ed. 2010, 49, 7992.
(17) Zhou, H. et al., *Macromolecules* 2010, 43, 10390.
(18) Zhou, H. et al., *Macromolecules* 2010, 43, 811.
(19) Shockley, W.; Queisser, H. J. *J. Appl. Phys.* 1961, 32, 510.
(20) Balan, A.; Gunbas, G.; Durmus, A.; Toppare, L. *Chem. Mater.* 2008, 20, 7510.
(21) Tanimoto, A.; Yamamoto, T. *Macromolecules* 2006, 39, 3546.
(22) Charushin, V. N. et al., *Mendeleev Commun.* 2005, 15, 45.
(23) Perez, M. D. et al., *J. Am. Chem. Soc.* 2009, 131, 9281.
(24) Yang, L. et al., *J. Phys. Chem. C* 2010, 114, 16793.
(25) Pagliaro, M.; Ciriminna, R. *J. Mater. Chem.* 2005, 15, 4981.
(26) Chen, D.-Y. et al., *Chem. Commun.* 2010, 46, 5256.
(27) Mihailetchi, V. D. et al., *Adv. Funct. Mater.* 2006, 16, 699.
(28) Mihailetchi, V. D. et al., *Phys. Rev. Lett.* 2005, 94, 126602.

The foregoing is illustrative of the present invention, and is not to be construed as limiting thereof. The invention is defined by the following claims, with equivalents of the claims to be included therein.

That which is claimed is:

1. A copolymer having the formula:

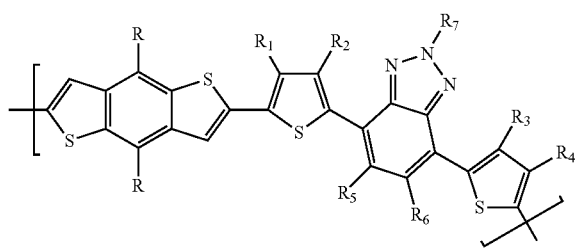

wherein each $R_1$, $R_2$, $R_3$, and $R_4$ is independently selected from the group consisting of H, C1-C20 alkyl, C1-C20 fluoroalkyl, C1-C20 alkoxy, C1-C20 fluoroalkoxy, halo, aryl, CN and $NO_2$;

$R_5$ and $R_6$ are fluoro; and each R and $R_7$ is C1-C20 alkyl.

2. The copolymer of claim 1, having a number average molecular weight for said polymer of from 500 to 1,000,000 grams per mole.

3. A copolymer having the formula:

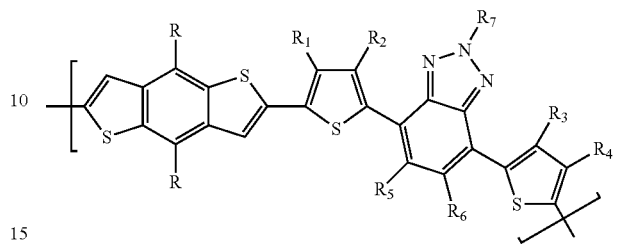

wherein:

$R_1$, $R_2$, $R_3$ and $R_4$ are each H;

$R_5$ and $R_6$ are fluoro; and

R and $R_7$ are each C1-C20 alkyl.

4. The copolymer of claim 3 having a number average molecular weight of from 500 to 1,000,000 grams per mole.

* * * * *